United States Patent
Bukhalid et al.

(10) Patent No.: US 10,072,299 B2
(45) Date of Patent: *Sep. 11, 2018

(54) ANTIBODIES AGAINST EPIDERMAL GROWTH FACTOR RECEPTOR (EGFR) AND USES THEREOF

(71) Applicant: Merrimack Pharmaceuticals, Inc., Cambridge, MA (US)

(72) Inventors: Raghida Bukhalid, Melrose, MA (US); Michael Feldhaus, Grantham, NH (US); Anne Richard, Cambridge, MA (US); Neeraj Kohli, Arlington, MA (US); Eric Krauland, Lebanon, NH (US); Jeffrey David Kearns, Arlington, MA (US); Alexey A. Lugovskoy, Belmont, MA (US); Ulrik Nielsen, Quincy, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 341 days.

This patent is subject to a terminal disclaimer.

(21) Appl. No.: 14/847,297

(22) Filed: Sep. 8, 2015

(65) Prior Publication Data

US 2015/0368347 A1 Dec. 24, 2015

Related U.S. Application Data

(63) Continuation of application No. 14/147,331, filed on Jan. 3, 2014, now Pat. No. 9,226,964, which is a continuation-in-part of application No. PCT/US2012/045235, filed on Jul. 2, 2012.

(60) Provisional application No. 61/558,945, filed on Nov. 11, 2011, provisional application No. 61/504,633, filed on Jul. 5, 2011.

(51) Int. Cl.

| C07K 16/28 | (2006.01) |
| C12Q 1/6886 | (2018.01) |
| G01N 33/574 | (2006.01) |
| G01N 33/74 | (2006.01) |
| A61K 39/395 | (2006.01) |
| C07K 16/32 | (2006.01) |
| C12Q 1/686 | (2018.01) |
| A61K 9/00 | (2006.01) |
| C07K 16/30 | (2006.01) |
| C07K 14/71 | (2006.01) |
| A61K 39/00 | (2006.01) |

(52) U.S. Cl.
CPC .......... *C12Q 1/6886* (2013.01); *A61K 9/0019* (2013.01); *A61K 39/3955* (2013.01); *A61K 39/39558* (2013.01); *C07K 16/2863* (2013.01); *C07K 16/30* (2013.01); *C07K 16/32* (2013.01); *C12Q 1/686* (2013.01); *G01N 33/57484* (2013.01); *G01N 33/57496* (2013.01); *G01N 33/74* (2013.01); *A61K 2039/505* (2013.01); *A61K 2039/507* (2013.01); *C07K 14/71* (2013.01); *C07K 2317/21* (2013.01); *C07K 2317/24* (2013.01); *C07K 2317/34* (2013.01); *C07K 2317/55* (2013.01); *C07K 2317/56* (2013.01); *C07K 2317/565* (2013.01); *C07K 2317/76* (2013.01); *C07K 2317/92* (2013.01); *C12Q 2600/106* (2013.01); *G01N 2333/485* (2013.01); *G01N 2333/495* (2013.01); *G01N 2800/52* (2013.01)

(58) Field of Classification Search
None
See application file for complete search history.

(56) References Cited

U.S. PATENT DOCUMENTS

| 7,226,592 B2 | 6/2007 | Kreysch |
| 7,498,142 B2 | 3/2009 | Yarden et al. |
| 7,771,958 B2 | 8/2010 | Bacus et al. |
| 7,887,805 B2 | 2/2011 | Pedersen et al. |
| 8,008,003 B2 | 8/2011 | Baker et al. |
| 8,147,867 B2 | 4/2012 | Hong et al. |
| 8,329,213 B2 | 12/2012 | Hong et al. |
| 8,414,896 B2 | 4/2013 | Pedersen et al. |
| 8,691,231 B2 | 4/2014 | Bukhalid et al. |
| 8,703,181 B2 | 4/2014 | Hong et al. |
| 8,830,814 B2 | 9/2014 | Manakkal et al. |
| 8,992,970 B2 | 3/2015 | Hong et al. |
| 9,044,460 B2 | 6/2015 | Bukhalid et al. |
| 9,157,108 B2 | 10/2015 | Schaffer et al. |
| 9,226,964 B2 | 1/2016 | Bukhalid et al. |
| 9,339,497 B2 | 5/2016 | Bayever et al. |
| 2004/0052785 A1 | 3/2004 | Goodman et al. |
| 2005/0003403 A1 | 1/2005 | Rossi et al. |
| 2006/0228355 A1 | 10/2006 | Laeremans et al. |

(Continued)

FOREIGN PATENT DOCUMENTS

| CN | 101675075 A | 3/2010 |
| WO | 02/055106 A2 | 7/2002 |

(Continued)

OTHER PUBLICATIONS

U.S. Appl. No. 15/137,081, filed Apr. 25, 2016, Sabrina Arena.
U.S. Appl. No. 15/156,752, filed May 17, 2016, Jeffrey David Kearns.
U.S. Appl. No. 14/724,058, dated Jun. 16, 2016.
U.S. Appl. No. 14/147,331, dated Sep. 29, 2015.

(Continued)

*Primary Examiner* — Michael Pak
(74) *Attorney, Agent, or Firm* — Nelson Mullins Riley & Scarborough LLP; Jane E. Remillard, Esq.; Jill Gorny Sloper, Esq.

(57) ABSTRACT

Anti-EGFR antibodies, therapeutic compositions comprising combinations of anti-EGFR antibodies, as well as methods for using such antibodies and compositions to treat EGFR-related disorders (e.g., cancers), are disclosed.

21 Claims, 60 Drawing Sheets

Specification includes a Sequence Listing.

(56) References Cited

U.S. PATENT DOCUMENTS

| | | |
|---|---|---|
| 2008/0206236 A1 | 8/2008 | Haurum |
| 2008/0299120 A1 | 12/2008 | Miller et al. |
| 2009/0004192 A1 | 1/2009 | Pedersen et al. |
| 2009/0155288 A1 | 6/2009 | Yarden et al. |
| 2009/0181855 A1 | 7/2009 | Vasquez et al. |
| 2009/0226447 A1 | 9/2009 | Boone et al. |
| 2009/0298701 A1 | 12/2009 | Baker et al. |
| 2010/0056383 A1 | 3/2010 | Ririe et al. |
| 2011/0287002 A1 | 11/2011 | Bukhalid et al. |
| 2012/0308576 A1 | 12/2012 | Bukhalid et al. |
| 2014/0072563 A1 | 3/2014 | Daly et al. |
| 2014/0127207 A1 | 5/2014 | Bukhalid et al. |
| 2014/0170668 A1 | 6/2014 | Bukhalid et al. |
| 2014/0234314 A1 | 8/2014 | Bukhalid et al. |
| 2015/0231238 A1 | 8/2015 | Garcia et al. |
| 2015/0368346 A1 | 12/2015 | Bukhalid et al. |
| 2015/0368347 A1 | 12/2015 | Bukhalid et al. |
| 2015/0368361 A1 | 12/2015 | Bukhalid et al. |
| 2015/0376284 A1 | 12/2015 | Bukhalid et al. |
| 2016/0002339 A1 | 1/2016 | Bukhalid et al. |
| 2016/0009822 A1 | 1/2016 | Kearns et al. |
| 2016/0074382 A1 | 3/2016 | Bayever et al. |
| 2016/0083800 A1 | 3/2016 | Bukhalid et al. |
| 2016/0251445 A1 | 9/2016 | Kearns et al. |
| 2016/0311908 A1 | 10/2016 | Arena et al. |
| 2017/0253662 A1 | 9/2017 | Kearns et al. |
| 2017/0267779 A1 | 9/2017 | Kearns et al. |
| 2017/0314079 A1 | 11/2017 | Bukhalid et al. |
| 2017/0356049 A1 | 12/2017 | Bukhalid et al. |

FOREIGN PATENT DOCUMENTS

| | | |
|---|---|---|
| WO | 04/032961 A1 | 4/2004 |
| WO | 04/094613 A2 | 11/2004 |
| WO | 2008/095504 A1 | 8/2008 |
| WO | 2008/104183 A2 | 9/2008 |
| WO | 2009/030239 A1 | 3/2009 |
| WO | 2010/019952 A2 | 2/2010 |
| WO | 2011/0132182 A1 | 10/2011 |
| WO | 2011/140151 A1 | 11/2011 |
| WO | 2011/140254 A1 | 11/2011 |
| WO | 2013/006547 A2 | 1/2013 |
| WO | 2013/138371 A1 | 9/2013 |
| WO | 2013/188586 A1 | 12/2013 |
| WO | 2015/175827 A1 | 11/2015 |

OTHER PUBLICATIONS

Dienstmann, R. et al., "Phase I trial of the first-in-class EGFR antibody mixture, Sym004, in patients with advanced solid tumors.", Journal of Clinical Oncology, vol. 29, No. supl. 1, Abstract 3089,2 pages (Jan. 2011).

International Search Report and Written Opinion for Application No. PCT/US2012/045235, 13 pages, dated Feb. 20, 2013.

International Search Report and Written Opinion, PCT/US2015/030870, dated Oct. 12, 2015, 19 pages.

Invitation to Pay Additional Fees, and, Where Applicable, Protest Fees, PCT/US2015/030870, dated Aug. 5, 2015, 9 pages.

Paz-Ares, L. G. et al., "Phase I Pharmacokinetic and Pharmacodynamic Dose-Escalation Study of RG7160 (GA201), the First Glycoengineered Monoclonal Antibody Against the Epidermal Growth Factor Receptor, in Patients With Advanced Solid Tumors," Journal of Clinical Oncology, vol. 29 (28), pp. 3783-3790 (Oct. 2011).

Tebbutt, N. et al., "Targeting the ERBB Family in Cancer: couples Therapy," Nature Cancer Reviews, vol. 13, pp. 633-673 (2013).

International Search Report for Application No. PCT/US2011/035238, dated Oct. 17, 2011, 10 pages.

Baker, J.B. et al., "Tumour gene expression predicts response to cetuximab in patients with KRAS wild-type metastatic colorectal cancer," British Journal of Cancer, vol. 104:488-495 (2011 ).

Beeram, M. et al., "A first-in-human study evaluating safety and pharmacology of MM-151, a novel oligoclonal anti-EGFR antibody combination in patients with refractory solid tumors," The European Organisation for Research and Treatment of Cancer (EORTC), 2014, Abstract No. 329, Poster Presentation, 1 page.

Bukhalid, R. et al., "Therapeutically Targeting EGFR activation by high-affinity ligands with MM-151, a super-potent mixture of three human antibody antagonists," World Conference on Lung Cancer, 2011, Abstract P2.070, Poster Presentation, 1 page.

ClinicalTrials.gov, "A Phase I Study of Cetuximab in Combination With Gefitinib in Patients With Advanced/Metastatic Non-Small Cell Lung Cancer," Study NCT00162318, Bristol-Myers Squibb, 3 pages, date received Sep. 9, 2005.

ClinicalTrials.gov, "A Study of BIBW 2992 (Afatinib) in Patients With Metastatic Colorectal Cancer," Study NCT01152437, Boehringer Ingelheim Pharmaceuticals, 4 pages, date received Jun. 28, 2010.

ClinicalTrials.gov, "A Study of R1507 in Combination With Multiple Standard Chemotherapy Treatments in Patients With Advanced Solid Tumors," Study NCT00811993, Hoffmann-La Roche, 6 pages, dated received Dec. 18, 2008.

ClinicalTrials.gov, "A Study of SCH 717454 in Combination With Different Treatment Regimens in Subjects With Advanced Solid Tumors (P04722)," Study NCT00954512, Schering-Plough, 5 pages, dated received Jul. 23, 2009.

ClinicalTrials.gov, "An Umbrella, Modular Study Based on Epidermal Growth Factor Receptors (EGFR) Mutation Status," Study NCT00903734, M.D. Anderson Cancer Center, 5 pages, dated received May 14, 2009.

ClinicalTrials.gov, "Bevacizumab and Gemcitabine Combined With Either Cetuximab or Erlotinib in Treating Patients With Advanced Pancreatic Cancer," Study NCT00091026, National Cancer Institute (NCI), 6 pages, dated received Sep. 7, 2004.

ClinicalTrials.gov, "Bevacizumab in Multiple Phase I Combinations," Study NCT00543504, M.D. Anderson Cancer Center, 7 pages, dated received Oct. 11, 2007.

ClinicalTrials.gov, "BIBW 2992 (Afatinib) in Head & Neck Cancer," Study NCT00514943, Boehringer Ingelheim Pharmaceuticals, 5 pages, dated received Aug. 9, 2007.

ClinicalTrials.gov, "Carboplatin, Paclitaxel, Cetuximab, and Erlotinib Hydrochloride in Treating Patients With Metastatic or Recurrent Head and Neck Squamous Cell Cancer," Study NCT01316757, Fox Chase Cancer Center, 7 pages, dated received Mar. 8, 2011.

ClinicalTrials.gov, "Cetuximab in Patients With Lung Adenocarcinoma Receiving Erlotinib That Have Developed 'Acquired Resistance' to Erlotinib," Study NCT00716456, Memorial Sloan-Kettering Cancer Center, 1 page, dated received Jul. 15, 2008.

ClinicalTrials.gov, "Clinical and Pathologic Studies of Patients Undergoing Treatment With EGFR Inhibitors," Study NCT01137162, Stanford University, 1 page, dated received Jun. 1, 2010.

ClinicalTrials.gov, "Combination Study of BMS-754807 and Erbitux in Subjects With Advanced or Metastatic Solid Tumors," Study NCT00908024, Bristol-Myers Squibb, 4 pages, dated received May 22, 2009.

ClinicalTrials.gov, "Dual Epidermal Growth Factor Receptor Inhibition With Erlotinib and Panitumumab With or Without Chemotherapy for Advanced Colorectal Cancer," Study NCT00940316, Northwestern University, 1 page, dated received Jul. 15, 2011.

ClinicalTrials.gov, "Dual Inhibition of EGFR Signalling Using the Combination of Cetuximab and Erlotinib (Dux)," Study NCT00784667, Austin Health, 1 page, dated received Nov. 3, 2008.

ClinicalTrials.gov, "Erlotinib and Cetuximab in Treating Patients With Advanced Gastrointestinal Cancer, Head and Neck Cancer, Non-Small Cell Lung Cancer, or Colorectal Cancer," Study NCT00397384, Vanderbilt-Ingram Cancer Center, 1 page, dated received Nov. 8, 2006.

ClinicalTrials.gov, "Erlotinib and Cetuximab in Treating Patients With Advanced Solid Tumors With Emphasis on Non-Small Cell Lung Cancer," Study NCT00408499, University of California, Davis, 1 page, dated received Dec. 6, 2006.

ClinicalTrials.gov, "Erlotinib and Cetuximab With or Without Bevacizumab in Treating Patients With Metastatic or Unresectable Kidney, Colorectal, Head and Neck, Pancreatic, or Non-Small Cell Lung Cancer," Study NCT00101348, National Cancer Institute (NCI), 6 pages, dated received Jan. 7, 2005.

(56) References Cited

OTHER PUBLICATIONS

ClinicalTrials.gov, "Erlotinib and Gemcitabine With or Without Panitumumab in Treating Patients With Metastatic Pancreatic Cancer," Study NCT00550836, National Cancer Institute (NCI), 6 pages, dated received Oct. 26, 2007.
ClinicalTrials.gov, "Erlotinib in Combination With Cetuximab," Study NCT00895362, M.D. Anderson Cancer Center, 5 pages, dated received May 6, 2009.
ClinicalTrials.gov, "Evaluating Preventive Therapy With Oint Threolone, Synthomycine or Aqua Cream Lotion, for EGFR'I Induced Acneiform Rash," Study NCT01256437, Rabin Medical Center, 4 pages, dated received Dec. 7, 2010.
ClinicalTrials.gov, "Histological Characterization and Differentiation of Rash From Other Epidermal Growth Factor Receptor (EGFR) Inhibitors," Study NCT00709878, Northwestern University, 1 page, dated received Jul. 1, 2008.
ClinicalTrials.gov, "Individualized Drug Treatment Selection Process for Treating Patients with Pancreatic Cancer That Can Be Removed by Surgery," Study NCT00276744, Sidney Kimmel Comprehensive Cancer Center, 5 pages, dated received Jan. 12, 2006.
ClinicalTrials.gov, "Lapatinib and Cetuximab in Patients With Solid Tumors (TYKERB-ITUX 1)," Study NCT01184482, Georgetown University, 4 pages, dated received Aug. 17, 2010.
ClinicalTrials.gov, "Menadione Topical Lotion in Treating Skin Discomfort and Psychological Distress in Patients With Cancer Receiving Panitumumab, Erlotinib Hydrochloride, or Cetuximab," Study NCT01393821, Mayo Clinic, 5 pages, dated received Jun. 27, 2011.
ClinicalTrials.gov, "Pharmacodynamic Separation of Pemetrexed and Erlotinib as Second-line Therapy in Patients With Advanced Non-small Cell Lung Cancer (NSCLC)," Study NCT00950365, Montefiore Medical Center, 1 page, dated received Jul. 30, 2009.
ClinicalTrials.gov, "Pharmocokinetic/Pharmacodynamic (PK/PD) Study of the Combination Cetuximab/Gefitinib," Study NCT00820417, Harrison Clinical Research, 1 page, dated received Jan. 9, 2009.
ClinicalTrials.gov, "Phase 1 Trial With SIR-Spheres and Cetuximab +/− Erlotinib," Study NCT01432119, M.D. Anderson Cancer Center, 6 pages, dated received Sep. 8, 2011.
ClinicalTrials.gov, "Safety and Efficacy of Radiation/Cetuximab Plus EGFR Antisense DNA for Head and Neck Squamous Cell Carcinoma," Study NCT00903461, University of Pittsburgh, 5 pages, dated received May 14, 2009.
ClinicalTrials.gov, "Study About Preventive Treatment of Folliculitis Induced by Epidermal Growth Factor Receptor (EGF-R) Inhibitors (DIPROCOL)," Study NCT00910676, Centre Oscar Lambret, 4 pages, dated received May 29, 2009.
ClinicalTrials.gov, "Study of AMG 479 With Biologics or Chemotherapy for Subjects With Advanced Solid Tumors," Study NCT00974896, Amgen, 5 pages, dated received Sep. 10, 2009.
ClinicalTrials.gov, "Study of Cetuximab in Combination With Tarceva in Patients With Solid Tumors," Study NCT00207077, Bristol-Myers Squibb, 3 pages, dated received Sep. 12, 2005.
ClinicalTrials.gov, "Sym004 in Patients With Advanced Solid Tumors," Study NCT01117428, Symphogen A/S, 1 page, dated received Apr. 23, 2010.
ClinicalTrials.gov, "Sym004 in SCCHN Patients Failing Anti-EGFR Based Therapy," Study NCT01417936, Symphogen A/S, 1 page, dated received Jul. 15, 2011.
ClinicalTrials.gov, "Temsirolimus (Torisel) and Erlotinib (Tarceva) in Platinum-Refractory/Ineligible, Advanced, Squamous Cell Carcinoma," Study NCT01009203, New Mexico Cancer Care Alliance, 4 pages, dated received Nov. 5, 2009.
ClinicalTrials.gov, "Tetracycline in Preventing Skin Rash in Patients Who Are Receiving Drugs Such as Gefitinib and Cetuximab for Cancer," Study NCT00091247, National Cancer Institute (NCI), 1 page, dated received Sep. 7, 2004.
ClinicalTrials.gov, "Topical Sunscreen in Preventing Skin Rash in Patients Receiving Drugs Such as Erlotinib or Cetuximab for Cancer," Study NCT00362986, National Cancer Institute (NCI), 4 pages, dated received Aug. 10, 2006.
ClinicalTrials.gov, "Trial of BIBW 2992 (Afatinib) + Cetuximab in Non-Small Cell Lung Cancer," Study NCT01090011, Boehringer Ingelheim Pharmaceuticals, 1 page, dated received Mar. 10, 2010.
ClinicalTrials.gov, "Validation of Cancer Questionnaire for Skin Toxicities in Patients With Colorectal Cancer or Lung Cancer Receiving Cetuximab, Panitumumab, or Erlotinib Hydrochloride," Study NCT01416688, National Cancer Institute (NCI), 5 pages, dated received Aug. 12, 2011.
ClinicalTrials.gov, "ZD6474, Cetuximab, and Irinotecan in Patients With Metastatic Colorectal Cancer," Study NCT00436072, Dana-Farber Cancer Institute, 5 pages, dated received Feb. 15, 2007.
Cochran, Jennifer R. et al., "Domain-level antibody epitope mapping through yeast surface display of epidermal growth factor receptor fragments," Journal of Immunological Methods, vol. 287:147-158 (2004).
European Search Report for Application No. 12275088.8, 12 pages, dated Oct. 11, 2012.
Fogler, William E. et al., "Enhanced Cytotoxicity against Colon Carcinoma by Combinations of Noncompeting Monoclonal Antibodies to the 17-1A Antigen," Cancer Research, vol. 48:6303-6308 (1998).
Friedman, Lilach M. et al., "Synergistic down-regulation of receptor tyrosine kinases by combinations of mAbs: Implications for cancer innumotherapy," PNAS, vol. 102(6):1915-1920 (2005).
Gerami-Moayed, N. et al., "Preclinical Characterization of MM-151, an Oligoclonal Antibody Therapeutic That Targets EGFR by Three Distinct Mechanisms of Action," The European Organisation for Research and Treatment of Cancer (EORTC), 2014, Abstract No. 152, Poster Presentation, 1 page.
Grandis, Jennifer Rubin et al., "Levels of TGF-alpha and EGFR Protein in Head and Neck Squamous Cell Carcinoma and Patient Survival," Journal of the National Cancer Institute, vol. 90(11):824-832 (1998).
Harb, W. et al. "A First-in-Human Study Evaluating Safety and Pharmacology of MM-151, a Novel Oligoclonal anti-EGFR antibody combination in patients with refractory solid tumors," European Society for Medical Oncology, 2014, Poster Presentation, 1 page.
Hatakeyama, Hiromitsu et al., "Regulation of Heparin-Binding EGF-Like Growth Factor by MiR-212 and Acquired Cetuximab-Resistance in Head and Neck Squamous Cell Carcinoma," PLoS ONE, vol. 5(9):e12702, 1-13 (2010).
U.S. Appl. No. 14/181,307, dated Jul. 20, 2015.
U.S. Appl. No. 14/867,554, dated Sep. 28, 2015.
U.S. Appl. No. 13/100,920, filed Apr. 5, 2011, Raghida Bukhalid.
U.S. Appl. No. 14/724,058, filed May 28, 2015, Raghida Bukhalid.
U.S. Appl. No. 14/847,351, filed Sep. 8, 2015, Raghida Bukhalid.
U.S. Appl. No. 13/488,270, filed Jun. 4, 2012, Raghida Bukhalid.
U.S. Appl. No. 14/181,307, filed Feb. 14, 2014, Raghida Bukhalid.
U.S. Appl. No. 14/147,331, filed Jan. 3, 2014, Raghida Bukhalid.
U.S. Appl. No. 14/266,387, filed Apr. 30, 2014, Raghida Bukhalid.
U.S. Appl. No. 14/847,291, filed Sep. 8, 2015, Raghida Bukhalid.
U.S. Appl. No. 14/847,304, filed Sep. 8, 2015, Raghida Bukhalid.
U.S. Appl. No. 13/100,920, dated Jan. 27, 2015.
U.S. Appl. No. 13/100,920, dated Jul. 9, 2014.
U.S. Appl. No. 13/100,920, dated Jan. 7, 2014.
U.S. Appl. No. 13/100,920, dated Aug. 28, 2013.
U.S. Appl. No. 13/488,270, dated Nov. 15, 2013.
U.S. Appl. No. 13/488,270, dated Jul. 8, 2013.
U.S. Appl. No. 13/488,270, dated Jan. 16, 2013.
U.S. Appl. No. 13/488,270, dated Oct. 23, 2012.
U.S. Appl. No. 14/181,307, dated Apr. 2, 2015.
U.S. Appl. No. 14/181,307, dated Dec. 18, 2014.
U.S. Appl. No. 14/181,307, dated Aug. 23, 2013.
U.S. Appl. No. 14/147,331, dated Jun. 18, 2015.
U.S. Appl. No. 14/147,331, dated Dec. 22, 2014.
U.S. Appl. No. 14/266,387, dated Jul. 20, 2015.
European Search Report, EP Application No. 16173573.3, dated Jul. 27, 2016, 5 pages.
Montagut, C. et al., "Identification of a mutation in the extracellular domain of the Epidermal Growth Factor Receptor conferring cetuximab resistance in colorectal cancer," Nature Medicine, vol. 18(2):221-223 (2012).

(56) References Cited

OTHER PUBLICATIONS

Voigt, M. et al. "Functional Dissection of the Epidermal Growth Factor Receptor Epitopes Targeted by Panitumumab and Cetuximab," Neoplasia, vol. 14: 1023-1031 (2012).
International Preliminary Report on Patentability and Written Opinion for Application No. PCT/US2012/045235, 7 pages, dated Jan. 7, 2014.
International Preliminary Report on Patentability for Application No. PCT/US2011/035238, 7 pages, dated Nov. 6, 2012.
International Search Report for Application No. PCT/US2012/045235, 5 pages, dated Feb. 20, 2013.
Kamat, Vishal et al., "Enhanced EGFR inhibition and distinct epitope recognition by EGFR antagonistic mAbs C225 and 425," Cancer Biology & Therapy, vol. 7(5):726-733 (2008).
Lieu, C. et al., "Phase 1 Trial of MM-151, a novel oligoclonal anti-EGFR antibody combination in patients with refractory solid tumors," American Society of Clinical Oncology, 2014, Poster Presentation, 1 page.
Lieu, C. et al., "Safety, pharmacology, and preliminary activity of MM-151: an oligoclonal anti-EGFR Therapeutic in patients with cetuximab-resistant CRC and other refractory solid tumors," American Society of Clinical Oncology, 2015, Abstract No. 647, Poster Presentation, 1 page.
Modjtahedi, H. et al., "Antitumor Activity of Combinations of Antibodies Directed Against Different Epitopes on the Extracellular Domain of the Human EGF Receptor," Cell Biophysics, vol. 22(1-3):129-146 (1993).
Nahta, Rita et al., "The HER-2-Targeting Antibodies Trastuzumab and Pertuzumab Synergistically Inhibit the Survival of Breast Cancer Cells," Cancer Research, vol. 64:2343-2346 (2004).
Nowakowski, A. et al., "Potent neutralization of botulinum neurotoxin by recombinant oligoclonal antibody," PNAS, vol. 99(17):11346-11350 (2002).
Pedersen, Mikkel Wandahl et al., "Sym004: A Novel Synergistic Anti-Epidermal Growth Factor Receptor Antibody Mixture with Superior Anticancer Efficacy," Cancer Research, vol. 70(2):588-597 (2010).
Perera, Rushika M. et al., "Treatment of Human Tumor Xenografts with Monoclonal Antibody 806 in Combination with a Prototypical Epidermal Growth Factor Receptor-Specific Antibody Generates Enhanced Antitumor Activity," Clinical Cancer Research, vol. 11(17):6390-6399 (2005).
Regales, Lucia et al., "Dual targeting of EGFR can overcome a major drug resistance mutation in mouse models of EGFR mutant lung cancer," The Journal of Clinical Investigation, vol. 119(10):3000-3010 (2009).
Saridaki, Zacharenia et al., "Impact of KRAS, BRAF, PIK3CA Mutations, PTEN, AREG, EREG Expression and Skin Rash in 2nd Line Cetuximab-Based Therapy of Colotectal Cancer Patients," PLoS ONE, vol. 6(1):e15980, 1-13 (2011).
Schoeberl, Birgit et al., "Therapeutically Targeting ErbB3: A Key Node in Ligand-Induced Activation of the ErbB Receptor-PI3K Axis," Science Signaling, vol. 2(77):ra31, 1-14 (2009).
Siena, Salvatore et al., "Biomarkers Predicting Clinical Outcome of Epidermal Growth Factor Receptor-Targeted Therapy in Metastatic Colorectal Cancer," J. Natl. Cancer, vol. 101:1-17 (2009).
Skartved, Niels Jorgen Ostergaard et al., "Preclinical Pharmacokinetics and Safety of Sym004: A Synergistic Antibody Mixture Directed against Epidermal Growth Factor Receptor," Clinical Cancer Research, vol. 17 (18):5962-5972 (2011).
Spangler, Jamie B. et al., "Combination antibody treatment downregulates epidermal growth factor receptor by inhibiting endosomal recycling," PNAS, vol. 107(30):13252-13257 (2010).
Spiridon, Camelia I. et al., "Targeting Multiple HER-2 Epitopes with Monoclonal Antibodies Results in Improved Antigrowth Activity of a Human Breast Cancer Cell Line in Vitro and In Vivo," Clinical Cancer Research, vol. 8:1720-1730 (2002).

Tabernero, Josep et al., "Pharmacogenomic and Pharmacoproteomic Studies of Cetuximab in Metastatic Colorectal Cancer: Biomarker Analysis of a Phase I Dose-Escalation Study," J. Clin. Oncol., vol. 28:1181-1189 (2010).
Tan, G. et al., "Mechanism of action of MM-151, a mixture of three human antibody antagonists targeting EGFR," American Association for Cancer Research (AACR), 2011, Abstract A210, Poster Presentation, 1 page.
Tomax, T., "Immunology," Laboratory of Immunology, National Institute of Allergy and Infectious Diseases, National; Institutes of Health, Edited by Paul W., MIR, Moscow "World", vol. 3 (1989), pp. 1-6.
Werner, S. et al., "Therapeutically Targeting High-Affinity Ligand Activation of EGFR with MM-151, an oligoclonal therapeutic," American Association for Cancer Research (AACR), 2011, Abstract P.A144, Poster Presentation, 1 page.
Wikipedia, "Competitive inhibition," retrieved online at: http://en.wikipedia.org/w/index.php?title=Competitive_inhibition, 5 pages (2011).
Yonesaka, Kimio et al., "Autocrine Production of Amphiregulin Predicts Sensitivity to Both Gefitinib and Cetuximab and EGFR Wild-type Cancers," Clin. Cancer Res., vol. 14(21):6963-6973 (2008).
U.S. Appl. No. 15/387,095, filed Dec. 21, 2016, Jeffrey David Kearns.
U.S. Appl. No. 14/833,834, filed Aug. 24, 2015, Raghida Bukhalid.
U.S. Appl. No. 15/234,402, filed Aug. 11, 2016, Raghida Bukhalid.
U.S. Appl. No. 15/462,738, filed Mar. 17, 2017, Raghida Bukhalid.
U.S. Appl. No. 15/630,773, filed Jun. 22, 2017, Raghida Bukhalid.
U.S. Appl. No. 14/867,554, filed Sep. 28, 2015, Jeffrey David Kearns.
U.S. Appl. No. 15/598,116, filed May 17, 2017, Jeffrey David Kearns.
U.S. Appl. No. 15/387,095, dated Nov. 2, 2017.
U.S. Appl. No. 15/387,095, dated Jun. 27, 2017.
U.S. Appl. No. 14/847,351, dated Nov. 30, 2017.
U.S. Appl. No. 14/847,351, dated May 19, 2017.
U.S. Appl. No. 14/833,834, dated May 12, 2016.
U.S. Appl. No. 14/847,291, dated Oct. 18, 2017.
U.S. Appl. No. 14/847,291, dated Mar. 10, 2017.
U.S. Appl. No. 14/847,304, dated Sep. 26, 2017.
U.S. Appl. No. 14/847,304, dated Mar. 9, 2017.
U.S. Appl. No. 14/867,554, dated Jan. 13, 2017.
U.S. Appl. No. 14/867,554, dated Sep. 6, 2016.
U.S. Appl. No. 14/867,554, dated Jan. 14, 2016.
U.S. Appl. No. 14/867,554, dated Nov. 23, 2015.
Cutsem E.V., et al. "Cetuximab and chemotherapy as initial treatment for metastatic colorectal cancer," The N.Eng.J. Med, vol. 360 (14): 1408-1417 (2009).
Braig, F. et al., "Epidermal growth factor receptor mutation mediates cross-resistance to panitumumab and cetuximab in gastrointestinal cancer," Oncotarget, vol. 6(14):12035-12047 (2015).
International Preliminary Reporton Patentability, PCT/2016/028987, dated Oct. 24, 2017, 8 pages.
International Search Report and Written Opinion, PCT/US2016/028987, dated Jul. 20, 2016, 15 pages.
RT2 ProfilerTM PCR Array system manual—from SA Biociences, Version 5.01, Sep. 16, 2010.
Bazdar-Vinovrski, B. et al., "A Phase 1 biomarker-directed multi-arm study evaluating the co-administration of MM-151 with seribantumab (MM-121), istiratumab (MM-141), or trametinib in EGFR-driven cancers," American Society of Clinical Oncology Annual Meeting, Abstract No. TPS11619, 1 page (2016).
Chan, E. et al., "A Phase 1/2 Study Combining MM-151+nal-IRI+ 5-FU +Leucovorin in RAS/RAF Wild-Type Metastatic Colorectal Cancer," American Society of Clinical Oncology Annual Meeting, Abstract No. 168108, 1 page (2016).
Wang, H. et al., "MM-151 elicits broad and unique inhibition of cells harboring EGFR extracellular domain mutations—results of multi-scale experiments with genome-edited cell lines," American Association for Cancer Research (AACR) Annual meeting, Abstract No. 2148, 1 page (2016).
Qiagen product guide 2004.

(56) References Cited

OTHER PUBLICATIONS

Masson, K. et al., "A network biology screen reveals ligand-receptor pathway connections and resistance mechanisms to RTK-directed therapies in cancer cells," American Association for Cancer Research (AACR) Annual meeting, Abstract No. 1199, 1 page (2016).

[P1X+P2X+P3X] + MM-121 in cell line 'A549' on Day #5

Percent Inhibition Relative to Control

| | | [P1X+P2X+P3X] (nM) | | | | | | | |
|---|---|---|---|---|---|---|---|---|---|
| | | 0.0 | 2000 | 666.7 | 222.2 | 74.1 | 24.7 | 8.2 | 2.7 | 0.9 | 0.3 |
| MM-121 (nM) | 0.0 | 0.0 | 24.5 | 18.8 | 22.1 | 19.0 | 21.3 | 21.4 | 15.0 | 11.7 | 7.5 |
| | 2000 | 28.6 | 68.9 | 68.4 | 66.8 | 67.1 | 66.2 | 64.0 | 58.4 | 50.5 | 44.9 |
| | 666.7 | 36.4 | 70.1 | 71.2 | 70.1 | 69.2 | 67.8 | 64.6 | 60.7 | 53.0 | 48.2 |
| | 222.2 | 33.3 | 67.4 | 66.5 | 66.5 | 65.8 | 65.0 | 62.1 | 59.0 | 50.6 | 42.1 |
| | 74.1 | 32.4 | 61.1 | 61.1 | 59.7 | 58.7 | 58.9 | 57.4 | 52.3 | 47.2 | 41.5 |
| | 24.7 | 28.1 | 53.8 | 54.3 | 53.4 | 54.3 | 54.2 | 51.7 | 48.2 | 40.7 | 34.2 |
| | 8.2 | 26.5 | 47.3 | 45.4 | 46.4 | 47.6 | 46.2 | 44.5 | 41.1 | 36.2 | 33.2 |
| | 2.7 | 14.9 | 33.9 | 33.1 | 34.2 | 34.8 | 33.1 | 34.2 | 31.2 | 28.3 | 24.0 |

Bliss Independence Score

| | | [P1X+P2X+P3X] (nM) | | | | | | | |
|---|---|---|---|---|---|---|---|---|---|
| | | 0.0 | 2000 | 666.7 | 222.2 | 74.1 | 24.7 | 8.2 | 2.7 | 0.9 | 0.3 |
| MM-121 (nM) | 0.0 | | | | | | | | | | |
| | 2000 | | -22.8 | -26.4 | -22.4 | -25.0 | -22.4 | -20.2 | -19.1 | -13.5 | -10.9 |
| | 666.7 | | -18.2 | -22.8 | -19.7 | -20.7 | -17.8 | -14.6 | -14.7 | -9.2 | -7.0 |
| | 222.2 | | -17.7 | -20.6 | -18.4 | -19.8 | -17.5 | -14.4 | -15.7 | -9.4 | -3.8 |
| | 74.1 | | -12.2 | -16.0 | -12.4 | -13.5 | -12.1 | -10.6 | -9.7 | -6.8 | -4.0 |
| | 24.7 | | -8.1 | -12.7 | -9.4 | -12.5 | -10.7 | -8.2 | -9.2 | -4.2 | -0.7 |
| | 8.2 | | -2.8 | -5.1 | -3.7 | -7.2 | -4.1 | -2.3 | -3.5 | -1.1 | -1.3 |
| | 2.7 | | 1.8 | -2.2 | -0.5 | -3.7 | -0.1 | -1.1 | -3.5 | -3.4 | -2.8 |

Fig 16A

Percent Inhibition Relative to Control

[P1X+P2X+P3X] + MM-121 in cell line 'BxPC-3' on Day #3

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 39.5 | 34.1 | 28.2 | 19.7 | 9.8 | 4.4 | 4.5 | 7.9 | 0.3 |
| 2000 | 51.4 | 70.6 | 68.8 | 65.4 | 61.5 | 56.3 | 54.7 | 55.3 | 54.6 | 52.3 |
| 666.7 | 50.4 | 68.2 | 65.9 | 61.7 | 60.2 | 56.1 | 53.6 | 52.1 | 53.3 | 52.8 |
| 222.2 | 45.2 | 63.8 | 62.0 | 59.2 | 56.8 | 51.1 | 47.2 | 50.3 | 51.2 | 40.4 |
| 74.1 | 34.6 | 61.1 | 58.7 | 55.2 | 48.8 | 47.7 | 38.8 | 40.4 | 38.9 | 41.2 |
| 24.7 | 24.6 | 57.0 | 52.4 | 49.1 | 42.2 | 35.2 | 27.2 | 27.6 | 26.0 | 27.1 |
| 8.2 | 15.0 | 54.1 | 47.8 | 40.3 | 34.6 | 32.3 | 20.7 | 18.5 | 19.8 | 19.9 |
| 2.7 | -1.3 | 40.7 | 38.9 | 13.9 | 4.9 | 12.1 | 9.0 | 8.4 | 6.3 | 9.3 |

Bliss Independence Score

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 2000 | | 0.0 | -0.8 | -0.3 | -0.6 | -0.1 | -1.2 | -1.8 | 0.6 | 3.7 |
| 666.7 | | 1.8 | 1.4 | 2.7 | 0.0 | -0.8 | -1.0 | 0.5 | 1.0 | 2.4 |
| 222.2 | | 3.0 | 1.8 | 1.4 | -0.8 | -0.5 | 0.4 | -2.6 | -1.7 | 10.1 |
| 74.1 | | -0.7 | -1.7 | -2.1 | -1.3 | -6.7 | -1.3 | -2.9 | 0.9 | -0.2 |
| 24.7 | | -2.6 | -2.1 | -3.2 | -2.7 | -3.2 | 0.7 | 0.4 | 4.6 | 4.8 |
| 8.2 | | -5.5 | -3.8 | -1.3 | -2.8 | -9.0 | -1.9 | 0.4 | 2.0 | 3.4 |
| 2.7 | | -2.0 | -5.6 | 13.3 | 13.8 | -3.5 | -5.8 | -5.2 | 0.3 | -0.8 |

Fig 16B

Percent Inhibition Relative to Control

[P1X+P2X+P3X] + MM-121 in cell line 'DU 145' on Day #3

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 41.7 | 37.6 | 31.0 | 23.6 | 9.8 | 3.8 | 3.3 | 5.7 | 10.0 |
| 2000 | 14.6 | 67.8 | 65.3 | 62.5 | 53.3 | 32.0 | 25.7 | 20.8 | 20.9 | 21.9 |
| 666.7 | 13.7 | 64.9 | 64.1 | 59.1 | 47.1 | 29.9 | 22.9 | 21.3 | 19.8 | 21.8 |
| 222.2 | 10.8 | 58.5 | 56.3 | 49.9 | 43.7 | 24.2 | 19.4 | 17.8 | 18.7 | 20.6 |
| 74.1 | 7.1 | 49.0 | 47.1 | 42.1 | 32.3 | 14.9 | 11.0 | 12.0 | 11.5 | 15.3 |
| 24.7 | 1.0 | 42.8 | 37.7 | 35.5 | 24.6 | 12.1 | 6.2 | 8.8 | 7.2 | 8.2 |
| 8.2 | -7.0 | 33.7 | 31.8 | 29.1 | 17.3 | 6.1 | 2.7 | 2.7 | 3.2 | 2.8 |
| 2.7 | -7.6 | 28.7 | 26.0 | 21.1 | 15.8 | 2.2 | 1.2 | 1.0 | -0.6 | 0.3 |

Bliss Independence Score

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 2000 | | -17.5 | -18.5 | -21.4 | -18.5 | -9.0 | -7.8 | -3.3 | -1.3 | 1.3 |
| 666.7 | | -15.2 | -18.0 | -18.6 | -13.0 | -7.7 | -6.0 | -4.7 | -1.2 | 0.6 |
| 222.2 | | -10.5 | -11.9 | -11.5 | -11.9 | -4.7 | -5.2 | -4.0 | -2.8 | -0.9 |
| 74.1 | | -3.2 | -5.0 | -6.2 | -3.3 | 1.4 | -0.3 | -1.8 | 0.9 | 1.1 |
| 24.7 | | -0.6 | 0.6 | -3.9 | -0.3 | -1.4 | -1.5 | -4.5 | -0.5 | 2.7 |
| 8.2 | | 4.0 | 1.5 | -2.9 | 1.0 | -2.6 | -5.6 | -6.1 | -4.0 | 1.0 |
| 2.7 | | 8.6 | 6.9 | 4.7 | 2.0 | 0.7 | -4.7 | -5.0 | -0.9 | 2.9 |

Fig 16C

Percent Inhibition Relative to Control

[P1X+P2X+P3X] + MM-121 in cell line 'NCI-H1355' on Day #5

| MM-121 (nM) \ [P1X+P2X+P3X] (nM) | 0.0 | 2000 | 666.7 | 222.2 | 74.1 | 24.7 | 8.2 | 2.7 | 0.9 | 0.3 |
|---|---|---|---|---|---|---|---|---|---|---|
| 0.0 | 0.0 | 7.9 | 10.0 | 8.3 | 7.3 | 3.4 | 0.0 | -2.0 | -9.6 | -5.4 |
| 2000 | 14.6 | 38.2 | 40.7 | 38.7 | 36.1 | 32.5 | 30.9 | 27.3 | 25.0 | 19.9 |
| 666.7 | 12.8 | 36.6 | 37.1 | 33.6 | 32.2 | 30.6 | 27.5 | 29.0 | 22.7 | 20.8 |
| 222.2 | 12.4 | 33.8 | 33.5 | 31.8 | 30.2 | 29.0 | 25.8 | 23.6 | 20.1 | 21.7 |
| 74.1 | 11.3 | 30.7 | 31.6 | 26.6 | 27.6 | 25.8 | 21.4 | 19.7 | 17.8 | 17.8 |
| 24.7 | 9.8 | 28.8 | 26.5 | 23.4 | 25.1 | 18.2 | 18.8 | 16.3 | 15.9 | 16.6 |
| 8.2 | 8.1 | 25.5 | 23.4 | 19.3 | 19.6 | 17.4 | 16.2 | 14.8 | 12.0 | 15.1 |
| 2.7 | 2.8 | 22.7 | 19.9 | 20.7 | 19.2 | 16.3 | 12.3 | 10.8 | 10.3 | 10.5 |

Bliss Independence Score

| MM-121 (nM) \ [P1X+P2X+P3X] (nM) | 0.0 | 2000 | 666.7 | 222.2 | 74.1 | 24.7 | 8.2 | 2.7 | 0.9 | 0.3 |
|---|---|---|---|---|---|---|---|---|---|---|
| 0.0 | | | | | | | | | | |
| 2000 | | -16.9 | -17.6 | -17.0 | -15.3 | -15.0 | -16.3 | -14.4 | -18.6 | -9.9 |
| 666.7 | | -16.9 | -15.6 | -13.6 | -13.0 | -14.8 | -14.7 | -17.9 | -18.3 | -12.7 |
| 222.2 | | -14.5 | -12.3 | -12.1 | -11.4 | -13.6 | -13.4 | -13.0 | -16.1 | -14.0 |
| 74.1 | | -12.4 | -11.4 | -7.9 | -9.8 | -11.5 | -10.1 | -10.2 | -15.0 | -11.3 |
| 24.7 | | -11.9 | -7.7 | -6.1 | -8.7 | -5.3 | -9.0 | -8.3 | -14.8 | -11.7 |
| 8.2 | | -10.1 | -6.1 | -3.6 | -4.8 | -6.2 | -8.1 | -8.5 | -12.7 | -12.0 |
| 2.7 | | -12.2 | -7.4 | -9.8 | -9.3 | -10.2 | -9.5 | -9.9 | -16.8 | -12.9 |

[P1X+P2X+P3X] + MM-121 in cell line 'NCI-H226' on Day #5

Percent Inhibition Relative to Control

| | | \[P1X+P2X+P3X\] (nM) | | | | | | | |
|---|---|---|---|---|---|---|---|---|---|
| | | 0.0 | 2000 | 666.7 | 222.2 | 74.1 | 24.7 | 8.2 | 2.7 | 0.9 | 0.3 |
| MM-121 (nM) | 0.0 | 0.0 | 31.5 | 31.1 | 34.8 | 35.4 | 31.9 | 23.0 | 15.2 | 11.2 | -10.5 |
| | 2000 | -2.1 | 35.7 | 35.4 | 35.1 | 37.1 | 28.4 | 20.5 | 20.1 | 9.0 | 8.5 |
| | 666.7 | -14.8 | 29.5 | 34.1 | 35.0 | 31.5 | 34.4 | 19.3 | 1.3 | 8.6 | 3.9 |
| | 222.2 | -15.4 | 35.5 | 35.9 | 30.5 | 36.0 | 33.6 | 24.6 | 15.2 | 5.3 | 3.0 |
| | 74.1 | -10.1 | 28.6 | 31.1 | 31.0 | 33.2 | 21.4 | 14.2 | 8.2 | 3.4 | 0.2 |
| | 24.7 | -10.9 | 34.6 | 30.0 | 34.4 | 32.2 | 27.9 | 19.7 | 9.5 | -0.8 | 4.8 |
| | 8.2 | -10.6 | 30.6 | 32.9 | 37.4 | 33.9 | 29.5 | 21.5 | 18.8 | 4.0 | 8.9 |
| | 2.7 | -10.1 | 27.1 | 20.9 | 29.4 | 33.6 | 41.5 | 21.6 | 13.8 | 9.7 | -0.1 |

Bliss Independence Score

| | | \[P1X+P2X+P3X\] (nM) | | | | | | | |
|---|---|---|---|---|---|---|---|---|---|
| | | 0.0 | 2000 | 666.7 | 222.2 | 74.1 | 24.7 | 8.2 | 2.7 | 0.9 | 0.3 |
| MM-121 (nM) | 0.0 | | | | | | | | | | |
| | 2000 | | -5.6 | -5.7 | -1.7 | -3.1 | _2.1_ | _0.9_ | -6.7 | _0.3_ | -21.3 |
| | 666.7 | | -8.1 | -13.2 | -9.8 | -5.7 | -12.6 | -7.7 | _1.3_ | -10.5 | -30.8 |
| | 222.2 | | -14.5 | -15.4 | -5.7 | -10.5 | -12.2 | -13.5 | -13.1 | -7.8 | -30.5 |
| | 74.1 | | -4.0 | -7.0 | -2.8 | -4.3 | _3.6_ | _1.0_ | -1.6 | -1.2 | -21.9 |
| | 24.7 | | -10.6 | -6.4 | -6.7 | -3.8 | -3.4 | -5.1 | -3.5 | _2.3_ | -27.3 |
| | 8.2 | | -6.4 | -9.1 | -9.5 | -5.3 | -4.8 | -6.7 | -12.6 | -2.2 | -31.1 |
| | 2.7 | | -2.5 | 3.2 | -1.2 | -4.7 | -16.5 | -6.4 | -7.2 | -7.5 | -21.6 |

Percent Inhibition Relative to Control

[P1X+P2X+P3X] + MM-121 in cell line 'NCI-H322M' on Day #3

| MM-121 (nM) \ [P1X+P2X+P3X] (nM) | 0.0 | 2000 | 666.7 | 222.2 | 74.1 | 24.7 | 8.2 | 2.7 | 0.9 | 0.3 |
|---|---|---|---|---|---|---|---|---|---|---|
| 0.0 | 0.0 | 18.8 | 15.9 | 15.3 | 9.1 | 6.0 | 0.3 | -1.8 | -2.6 | 3.7 |
| 2000 | 38.5 | 76.8 | 75.7 | 69.8 | 59.1 | 49.6 | 46.1 | 43.8 | 45.5 | 41.7 |
| 666.7 | 36.5 | 70.3 | 66.3 | 61.6 | 53.3 | 47.9 | 43.7 | 41.6 | 42.8 | 41.4 |
| 222.2 | 33.6 | 57.6 | 54.5 | 50.2 | 44.1 | 41.6 | 37.6 | 37.1 | 37.0 | 36.1 |
| 74.1 | 27.8 | 49.1 | 43.6 | 42.3 | 38.7 | 37.4 | 33.6 | 32.3 | 34.7 | 32.8 |
| 24.7 | 20.7 | 38.2 | 35.2 | 32.6 | 30.3 | 27.0 | 26.1 | 25.3 | 25.4 | 25.2 |
| 8.2 | 9.7 | 27.3 | 27.0 | 25.2 | 21.5 | 17.7 | 14.2 | 14.3 | 16.1 | 12.7 |
| 2.7 | 0.8 | 24.3 | 22.4 | 19.4 | 18.7 | 11.8 | 8.6 | 8.9 | 8.2 | 8.4 |

Bliss Independence Score

| MM-121 (nM) \ [P1X+P2X+P3X] (nM) | 0.0 | 2000 | 666.7 | 222.2 | 74.1 | 24.7 | 8.2 | 2.7 | 0.9 | 0.3 |
|---|---|---|---|---|---|---|---|---|---|---|
| 0.0 | | | | | | | | | | |
| 2000 | | -26.8 | -27.4 | -21.9 | -14.9 | -7.4 | -7.3 | -6.4 | -8.6 | -0.9 |
| 666.7 | | -21.9 | -19.7 | -15.3 | -11.0 | -7.5 | -6.9 | -6.2 | -7.9 | -2.5 |
| 222.2 | | -11.5 | -10.4 | -6.5 | -4.4 | -4.0 | -3.8 | -4.7 | -5.2 | -0.1 |
| 74.1 | | -7.8 | -4.4 | -3.5 | -4.3 | -5.2 | -5.6 | -5.9 | -8.8 | -2.4 |
| 24.7 | | -2.6 | -2.0 | 0.2 | -2.4 | -1.5 | -5.2 | -6.0 | -6.9 | -1.6 |
| 8.2 | | -0.6 | -3.0 | -1.7 | -3.6 | -2.6 | -4.2 | -6.3 | -8.8 | 0.2 |
| 2.7 | | -4.9 | -5.9 | -3.4 | -8.8 | -5.0 | -7.5 | -9.9 | -10.0 | -4.0 |

Fig 16F

Percent Inhibition Relative to Control

[P1X+P2X+P3X] + MM-121 in cell line 'NCI-H358' on Day #5

| MM-121 (nM) \ [P1X+P2X+P3X] (nM) | 0.0 | 2000 | 666.7 | 222.2 | 74.1 | 24.7 | 8.2 | 2.7 | 0.9 | 0.3 |
|---|---|---|---|---|---|---|---|---|---|---|
| 0.0 | 0.0 | 11.7 | 11.1 | 7.5 | 5.2 | 9.1 | -0.9 | -3.2 | -6.3 | -1.9 |
| 2000 | 36.3 | 63.2 | 63.9 | 62.4 | 62.3 | 56.4 | 45.4 | 44.0 | 35.0 | 36.0 |
| 666.7 | 27.8 | 56.2 | 53.3 | 54.0 | 52.8 | 45.6 | 46.4 | 30.3 | 31.5 | 31.8 |
| 222.2 | 23.5 | 45.4 | 42.4 | 47.0 | 42.1 | 40.0 | 40.2 | 29.0 | 24.2 | 32.9 |
| 74.1 | 16.3 | 40.7 | 38.5 | 36.7 | 38.4 | 34.3 | 29.1 | 29.7 | 26.6 | 22.7 |
| 24.7 | 5.4 | 28.7 | 28.3 | 30.8 | 23.1 | 19.6 | 14.2 | 22.6 | 12.8 | 15.2 |
| 8.2 | 10.0 | 29.1 | 27.7 | 24.3 | 26.9 | 22.4 | 23.5 | 18.6 | 16.2 | 21.5 |
| 2.7 | 3.4 | 18.4 | 24.0 | 18.6 | 11.7 | 5.4 | 17.6 | -2.3 | 0.7 | 1.2 |

Bliss Independence Score

| MM-121 (nM) \ [P1X+P2X+P3X] (nM) | 0.0 | 2000 | 666.7 | 222.2 | 74.1 | 24.7 | 8.2 | 2.7 | 0.9 | 0.3 |
|---|---|---|---|---|---|---|---|---|---|---|
| 0.0 | | | | | | | | | | |
| 2000 | | -19.4 | -20.5 | -21.3 | -22.7 | -14.3 | -9.7 | -9.7 | -2.7 | -0.9 |
| 666.7 | | -20.0 | -17.5 | -20.8 | -21.2 | -11.2 | -19.2 | -4.8 | -8.2 | -5.4 |
| 222.2 | | -12.9 | -10.4 | -17.8 | -14.6 | -9.5 | -17.4 | -7.9 | -5.5 | -10.9 |
| 74.1 | | -14.6 | -12.9 | -14.1 | -17.7 | -10.4 | -13.6 | -16.1 | -15.6 | -8.0 |
| 24.7 | | -12.2 | -12.4 | -18.3 | -12.8 | -5.6 | -9.7 | -20.2 | -13.4 | -11.6 |
| 8.2 | | -8.6 | -7.7 | -7.6 | -12.2 | -4.2 | -14.3 | -11.5 | -11.9 | -13.2 |
| 2.7 | | -3.7 | -9.9 | -8.0 | -3.3 | 6.8 | -15.1 | 2.6 | -3.4 | 0.4 |

Percent Inhibition Relative to Control

[P1X+P2X+P3X] + MM-121 in cell line 'NCI-H520' on Day #5

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | -9.6 | -10.1 | -10.2 | -8.1 | -7.5 | -14.5 | -14.0 | -14.3 | -4.0 |
| 2000 | 0.6 | 1.7 | 0.1 | 0.9 | 0.7 | 3.6 | 1.7 | 3.9 | 2.1 | 7.4 |
| 666.7 | 1.6 | 0.9 | -1.3 | 0.6 | 1.0 | 1.4 | -1.1 | 3.6 | 1.0 | 6.2 |
| 222.2 | 0.2 | 1.3 | 0.9 | 3.3 | 2.9 | 3.5 | 4.2 | 4.7 | 4.4 | 8.5 |
| 74.1 | -4.2 | -2.3 | -3.3 | -3.4 | -2.9 | -3.2 | 0.9 | -2.1 | -2.2 | 4.2 |
| 24.7 | -4.4 | -2.8 | -1.7 | -2.6 | -3.3 | -4.5 | -1.7 | 0.2 | -0.1 | 2.7 |
| 8.2 | -0.9 | 0.0 | -1.5 | -0.8 | 0.0 | -2.1 | -3.4 | 3.6 | 0.2 | -1.5 |
| 2.7 | -9.9 | -10.8 | -6.9 | -6.4 | -5.5 | -8.7 | -13.1 | -0.5 | -1.4 | 1.2 |

Bliss Independence Score

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 2000 | | -10.6 | -9.5 | -10.4 | -8.2 | -10.5 | -15.5 | -17.2 | -15.7 | -10.8 |
| 666.7 | | -8.7 | -7.0 | -9.0 | -7.4 | -7.2 | -11.6 | -15.8 | -13.5 | -8.5 |
| 222.2 | | -10.7 | -10.8 | -13.3 | -10.8 | -10.8 | -18.5 | -18.5 | -18.5 | -12.3 |
| 74.1 | | -11.9 | -11.4 | -11.4 | -9.7 | -8.8 | -20.2 | -16.7 | -16.9 | -12.6 |
| 24.7 | | -11.6 | -13.2 | -12.4 | -9.6 | -7.7 | -17.8 | -19.2 | -19.2 | -11.3 |
| 8.2 | | -10.6 | -9.6 | -10.4 | -9.1 | -6.4 | -12.1 | -18.6 | -15.5 | -3.4 |
| 2.7 | | -9.7 | -14.1 | -14.7 | -13.3 | -9.4 | -12.7 | -24.8 | -24.2 | -15.5 |

Fig 16I

Percent Inhibition Relative to Control

[P1X+P2X+P3X] + MM-121 in cell line 'HCC827' on Day #3

| | | | | [P1X+P2X+P3X] (nM) | | | | | |
|---|---|---|---|---|---|---|---|---|---|
| | | 0.0 | 2000 | 666.7 | 222.2 | 74.1 | 24.7 | 8.2 | 2.7 | 0.9 | 0.3 |
| MM-121 (nM) | 0.0 | 0.0 | 35.1 | 27.4 | 13.0 | 17.0 | 11.5 | 4.0 | -6.2 | 1.7 | -20.6 |
| | 2000 | 34.8 | 81.4 | 66.9 | 42.4 | 30.1 | 8.2 | 1.7 | 13.5 | -1.0 | 6.7 |
| | 666.7 | 20.0 | 78.2 | 64.8 | 45.9 | 16.5 | 13.9 | 9.9 | 13.7 | 5.8 | 6.1 |
| | 222.2 | 4.7 | 74.9 | 64.0 | 36.3 | 19.3 | 20.7 | 1.6 | 16.9 | -8.0 | -5.1 |
| | 74.1 | 1.3 | 68.8 | 58.2 | 38.4 | 19.0 | 6.8 | 4.2 | -0.5 | -8.1 | 3.5 |
| | 24.7 | 12.0 | 55.9 | 41.5 | 32.8 | 11.1 | 2.9 | 9.2 | 1.8 | 2.8 | 3.1 |
| | 8.2 | 8.6 | 44.8 | 32.2 | 20.8 | 16.6 | 0.3 | 3.7 | -2.3 | -1.0 | -11.7 |
| | 2.7 | 4.7 | 35.4 | 28.1 | 11.2 | 9.1 | 5.6 | 6.5 | -0.3 | 1.0 | -7.3 |

Bliss Independence Score

| | | | | [P1X+P2X+P3X] (nM) | | | | | |
|---|---|---|---|---|---|---|---|---|---|
| | | 0.0 | 2000 | 666.7 | 222.2 | 74.1 | 24.7 | 8.2 | 2.7 | 0.9 | 0.3 |
| MM-121 (nM) | 0.0 | | | | | | | | | | |
| | 2000 | | -23.8 | -14.3 | 0.8 | 15.7 | 34.1 | 35.7 | 17.2 | 36.9 | 14.6 |
| | 666.7 | | -30.2 | -23.0 | -15.5 | 17.0 | 15.3 | 13.2 | 1.3 | 15.6 | -2.6 |
| | 222.2 | | -36.8 | -33.2 | -19.2 | 1.6 | -5.1 | 6.8 | -18.1 | 14.3 | -9.9 |
| | 74.1 | | -32.9 | -29.9 | -24.3 | -0.9 | 5.9 | 1.0 | -4.3 | 11.1 | -22.6 |
| | 24.7 | | -13.0 | -5.4 | -9.3 | 15.9 | 19.3 | 6.3 | 4.8 | 10.8 | -9.2 |
| | 8.2 | | -4.2 | 1.4 | -0.3 | 7.6 | 18.9 | 8.5 | 5.3 | 11.2 | 1.4 |
| | 2.7 | | 2.7 | 2.7 | 5.9 | 11.8 | 10.2 | 2.0 | -0.9 | 5.4 | -7.7 |

Percent Inhibition Relative to Control

[P1X+P2X+P3X] + MM-121 in cell line 'HT-1197' on Day #5

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 20.6 | 15.6 | 17.6 | 13.8 | 16.3 | 11.0 | 13.1 | 7.3 | 6.2 |
| 2000 | 45.3 | 67.8 | 63.5 | 66.6 | 65.3 | 64.3 | 61.7 | 51.8 | 53.2 | 44.0 |
| 666.7 | 42.5 | 59.6 | 56.2 | 57.5 | 54.0 | 56.3 | 49.1 | 44.5 | 47.0 | 43.8 |
| 222.2 | 29.3 | 44.7 | 39.9 | 42.1 | 40.6 | 41.4 | 35.8 | 34.3 | 30.2 | 30.7 |
| 74.1 | 11.4 | 33.0 | 36.1 | 28.8 | 34.1 | 29.7 | 29.9 | 26.1 | 19.8 | 23.7 |
| 24.7 | 7.5 | 36.1 | 37.5 | 32.3 | 31.0 | 30.2 | 29.7 | 25.0 | 16.7 | 19.3 |
| 8.2 | 0.0 | 37.8 | 36.6 | 33.0 | 37.5 | 34.6 | 29.0 | 25.9 | 20.3 | 16.2 |
| 2.7 | -2.0 | 4.9 | -0.9 | -8.7 | -2.3 | -8.4 | -16.3 | -30.6 | -34.0 | -46.2 |

Bliss Independence Score

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 2000 | | -11.3 | -9.6 | -11.6 | -12.5 | -10.1 | -10.4 | 0.7 | -3.9 | 4.8 |
| 666.7 | | -5.2 | -4.7 | -4.9 | -3.6 | -4.4 | -0.3 | 5.5 | -0.3 | 2.3 |
| 222.2 | | -0.9 | 0.4 | -0.4 | -1.6 | -0.6 | 1.2 | 4.2 | 4.3 | 3.0 |
| 74.1 | | -3.3 | -11.0 | -1.8 | -10.6 | -3.9 | -8.9 | -3.2 | -1.9 | -6.8 |
| 24.7 | | -9.6 | -15.6 | -8.5 | -10.8 | -7.6 | -12.1 | -5.4 | -2.4 | -6.0 |
| 8.2 | | -17.3 | -21.1 | -15.4 | -23.7 | -18.3 | -18.1 | -12.9 | -13.0 | -10.0 |
| 2.7 | | 14.1 | 14.8 | 24.7 | 14.4 | 23.1 | 25.5 | 41.9 | 39.5 | 50.6 |

Fig 16J

Percent Inhibition Relative to Control

[P1X+P2X+P3X] + MM-121 in cell line 'RT-112' on Day #5

| MM-121 (nM) | [P1X+P2X+P3X] (nM) | | | | | | | | | |
|---|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 2.5 | 3.9 | 1.9 | 5.8 | 6.8 | 4.7 | 7.6 | -1.5 | 2.0 |
| 2000 | 51.8 | 72.2 | 73.1 | 75.5 | 75.5 | 72.8 | 72.0 | 67.3 | 57.3 | 53.0 |
| 666.7 | 44.9 | 69.1 | 69.3 | 69.0 | 68.4 | 67.5 | 65.3 | 60.3 | 56.2 | 48.1 |
| 222.2 | 40.9 | 61.0 | 60.3 | 59.3 | 59.4 | 56.7 | 56.7 | 50.0 | 44.3 | 41.0 |
| 74.1 | 36.7 | 53.2 | 49.9 | 49.3 | 48.7 | 48.0 | 46.8 | 44.0 | 38.1 | 29.5 |
| 24.7 | 36.9 | 42.6 | 38.5 | 39.1 | 40.2 | 43.3 | 38.6 | 36.1 | 30.7 | 28.0 |
| 8.2 | 25.9 | 30.5 | 29.5 | 31.4 | 31.8 | 31.4 | 29.0 | 23.4 | 23.6 | 22.2 |
| 2.7 | 19.1 | 23.2 | 21.7 | 19.0 | 26.7 | 21.7 | 21.0 | 18.5 | 13.2 | 8.7 |

Bliss Independence Score

| MM-121 (nM) | [P1X+P2X+P3X] (nM) | | | | | | | | | |
|---|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 2000 | | -19.3 | -19.4 | -22.8 | -20.9 | -17.7 | -18.0 | -11.8 | -6.3 | -0.3 |
| 666.7 | | -22.8 | -22.2 | -23.0 | -20.2 | -18.8 | -17.8 | -11.2 | -12.1 | -2.1 |
| 222.2 | | -18.7 | -17.1 | -17.3 | -15.0 | -11.8 | -13.1 | -4.6 | -4.3 | 1.1 |
| 74.1 | | -15.0 | -10.8 | -11.4 | -8.4 | -7.0 | -7.2 | -2.5 | -2.4 | 8.5 |
| 24.7 | | -4.1 | 0.9 | -1.0 | 0.4 | -2.2 | 1.2 | 5.6 | 5.2 | 10.1 |
| 8.2 | | -2.7 | -0.7 | -4.1 | -1.6 | -0.6 | 0.3 | 8.2 | 1.2 | 5.2 |
| 2.7 | | -2.0 | 0.6 | 1.6 | -2.9 | 2.8 | 1.9 | 6.8 | 4.7 | 12.1 |

Percent Inhibition Relative to Control

[P1X+P2X+P3X] + MM-121 in cell line 'SCaBER' on Day #5

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 71.8 | 71.5 | 73.7 | 73.9 | 73.8 | 65.2 | 53.2 | 39.4 | 27.5 |
| 2000 | 6.5 | 82.8 | 84.0 | 82.9 | 84.3 | 80.3 | 63.3 | 57.7 | 34.2 | 27.7 |
| 666.7 | 16.7 | 85.4 | 83.7 | 83.0 | 80.6 | 76.8 | 68.5 | 54.1 | 41.7 | 24.9 |
| 222.2 | -13.4 | 83.7 | 83.7 | 80.4 | 81.1 | 76.2 | 64.5 | 49.9 | 27.7 | 15.6 |
| 74.1 | 15.1 | 84.7 | 81.5 | 80.5 | 79.7 | 78.2 | 66.2 | 57.5 | 40.8 | 29.7 |
| 24.7 | 16.4 | 79.9 | 81.9 | 79.3 | 35.7 | 72.0 | 72.4 | 51.0 | 40.1 | 27.2 |
| 8.2 | 24.2 | 79.3 | 79.5 | 77.3 | 75.2 | 71.9 | 67.0 | 52.9 | 39.2 | 29.5 |
| 2.7 | 16.9 | 79.2 | 77.8 | 77.3 | 77.0 | 74.6 | 65.0 | 54.5 | 34.7 | 20.4 |

Bliss Independence Score

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 2000 | | -9.2 | -10.6 | -7.5 | -8.8 | -4.7 | 4.1 | -1.5 | 9.1 | 4.5 |
| 666.7 | | -8.9 | -7.4 | -4.9 | -2.3 | 1.4 | 2.5 | 6.9 | 7.9 | 14.7 |
| 222.2 | | -15.6 | -16.0 | -10.2 | -10.7 | -5.9 | -4.0 | -3.0 | 3.6 | 2.2 |
| 74.1 | | -8.6 | -5.7 | -2.8 | -1.9 | -0.4 | 4.3 | 2.7 | 7.8 | 8.7 |
| 24.7 | | -3.5 | -5.7 | -1.3 | 42.4 | 6.1 | -1.4 | 9.8 | 9.3 | 12.2 |
| 8.2 | | -0.6 | -1.1 | 2.8 | 5.0 | 8.3 | 6.7 | 11.6 | 14.9 | 15.6 |
| 2.7 | | -2.6 | -1.5 | 0.8 | 1.3 | 3.7 | 6.1 | 6.6 | 15.0 | 19.3 |

[P1X+P2X+P3X] + MM-121 in cell line 'SK-MES-1' on Day #5

Percent Inhibition Relative to Control

|  | | [P1X+P2X+P3X] (nM) | | | | | | | |
|---|---|---|---|---|---|---|---|---|---|
|  |  | 0.0 | 2000 | 666.7 | 222.2 | 74.1 | 24.7 | 8.2 | 2.7 | 0.9 | 0.3 |
| MM-121 (nM) | 0.0 | 0.0 | 77.5 | 77.1 | 74.8 | 75.0 | 67.0 | 55.9 | 32.4 | 17.4 | 7.6 |
|  | 2000 | -7.2 | 79.8 | 76.6 | 76.7 | 76.4 | 70.6 | 60.2 | 29.1 | 20.0 | 22.2 |
|  | 666.7 | -9.5 | 77.1 | 79.7 | 79.2 | 79.5 | 73.2 | 60.6 | 40.8 | 22.7 | 12.6 |
|  | 222.2 | 12.0 | 78.7 | 79.2 | 79.8 | 77.0 | 73.6 | 61.4 | 39.9 | 26.9 | 18.5 |
|  | 74.1 | 9.3 | 80.5 | 79.0 | 78.8 | 76.3 | 68.6 | 63.0 | 43.3 | 21.4 | 22.9 |
|  | 24.7 | 11.8 | 79.7 | 78.7 | 78.5 | 75.1 | 74.9 | 60.9 | 39.9 | 18.3 | 13.0 |
|  | 8.2 | 9.5 | 78.7 | 79.2 | 81.3 | 72.9 | 68.6 | 58.1 | 37.8 | 21.4 | 18.4 |
|  | 2.7 | 11.0 | 77.5 | 80.3 | 79.4 | 75.1 | 74.3 | 56.7 | 43.5 | 22.7 | 16.0 |

Bliss Independence Score

|  | | [P1X+P2X+P3X] (nM) | | | | | | | |
|---|---|---|---|---|---|---|---|---|---|
|  |  | 0.0 | 2000 | 666.7 | 222.2 | 74.1 | 24.7 | 8.2 | 2.7 | 0.9 | 0.3 |
| MM-121 (nM) | 0.0 |  |  |  |  |  |  |  |  |  |  |
|  | 2000 |  | -3.9 | -1.1 | -3.7 | -3.2 | -6.0 | -7.5 | -1.6 | -8.5 | -21.3 |
|  | 666.7 |  | -1.7 | -4.8 | -6.8 | -6.9 | -9.3 | -8.9 | -14.8 | -13.1 | -13.8 |
|  | 222.2 |  | 1.5 | 0.6 | -2.0 | 1.0 | -2.6 | -0.2 | 0.6 | 0.4 | 0.2 |
|  | 74.1 |  | -0.9 | 0.2 | -1.7 | 1.0 | 1.5 | -3.0 | -4.6 | 3.7 | -6.7 |
|  | 24.7 |  | 0.5 | 1.1 | -0.7 | 2.9 | -4.0 | 0.2 | 0.5 | 8.8 | 5.5 |
|  | 8.2 |  | 0.9 | 0.1 | -4.1 | 4.5 | 1.5 | 2.0 | 1.0 | 3.8 | -2.0 |
|  | 2.7 |  | 2.5 | -0.7 | -1.8 | 2.7 | -3.7 | 4.1 | -3.7 | 3.8 | 1.8 |

Fig 16M

Percent Inhibition Relative to Control

[P1X+P2X+P3X] + MM-121 in cell line 'SW 900' on Day #5

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 35.5 | 29.0 | 31.9 | 33.7 | 30.6 | 25.4 | 18.6 | 4.4 | -3.3 |
| 2000 | 8.8 | 57.9 | 55.5 | 55.0 | 55.2 | 55.7 | 50.5 | 41.1 | 18.3 | 8.6 |
| 666.7 | -2.0 | 55.8 | 56.5 | 55.2 | 51.5 | 50.7 | 53.2 | 37.2 | 25.7 | 14.8 |
| 222.2 | 0.9 | 47.6 | 52.0 | 52.1 | 53.4 | 48.0 | 54.1 | 39.3 | 22.3 | 15.1 |
| 74.1 | -3.7 | 44.1 | 47.5 | 42.4 | 48.0 | 40.7 | 42.7 | 31.0 | 6.5 | 4.6 |
| 24.7 | -4.8 | 42.4 | 41.2 | 42.3 | 42.1 | 42.7 | 40.0 | 25.4 | 15.8 | 4.6 |
| 8.2 | -9.8 | 41.9 | 44.2 | 41.1 | 42.6 | 39.2 | 34.9 | 28.7 | 8.9 | 1.7 |
| 2.7 | -9.2 | 37.4 | 38.2 | 37.2 | 43.6 | 37.6 | 36.5 | 26.7 | 12.0 | 0.4 |

Bliss Independence Score

| MM-121 (nM) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 2000 | | -16.7 | -20.3 | -17.1 | -15.7 | -19.0 | -18.5 | -15.3 | -5.5 | -2.8 |
| 666.7 | | -21.6 | -28.9 | -24.7 | -19.1 | -21.5 | -29.3 | -20.2 | -23.2 | -20.2 |
| 222.2 | | -11.5 | -22.4 | -19.6 | -19.1 | -16.8 | -28.0 | -20.0 | -17.0 | -17.5 |
| 74.1 | | -11.0 | -21.1 | -13.0 | -16.8 | -12.7 | -20.1 | -15.4 | -5.6 | -11.7 |
| 24.7 | | -10.0 | -15.6 | -13.7 | -11.6 | -15.4 | -18.2 | -10.7 | -16.0 | -12.9 |
| 8.2 | | -12.7 | -22.2 | -15.9 | -15.4 | -15.4 | -16.8 | -18.1 | -13.9 | -15.1 |
| 2.7 | | -7.8 | -15.7 | -11.6 | -16.0 | -13.4 | -18.0 | -15.6 | -16.4 | -13.2 |

Fig 16N

[P1X+P2X+P3X] + Docetaxel in cell line 'A549' on Day #5

Percent Inhibition Relative to Control

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 39.7 | 42.9 | 42.5 | 39.2 | 30.1 | 25.0 | 22.3 | 4.2 | 2.9 |
| 1000 | 76.3 | 82.7 | 83.1 | 82.2 | 83.8 | 82.9 | 82.0 | 81.4 | 79.4 | 78.7 |
| 333.3 | 77.4 | 85.5 | 86.4 | 85.7 | 85.5 | 84.6 | 85.7 | 84.5 | 81.9 | 80.4 |
| 111.1 | 62.1 | 75.5 | 74.9 | 74.5 | 73.3 | 73.8 | 72.7 | 71.6 | 68.8 | 65.7 |
| 37.0 | 44.8 | 65.5 | 67.0 | 67.3 | 64.9 | 65.7 | 61.7 | 61.3 | 53.1 | 48.7 |
| 12.3 | 42.1 | 63.5 | 63.2 | 63.9 | 63.1 | 58.8 | 60.9 | 54.6 | 56.2 | 51.3 |
| 4.1 | 7.3 | 50.5 | 51.5 | 46.9 | 49.2 | 46.2 | 37.9 | 32.9 | 25.1 | 17.2 |
| 1.4 | -4.0 | 44.0 | 43.5 | 42.7 | 41.6 | 39.2 | 25.7 | 9.5 | 8.7 | 7.1 |

Bliss Independence Score

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 1000 | | 3.0 | 3.4 | 4.2 | 1.8 | 0.5 | 0.2 | 0.2 | -2.1 | -1.7 |
| 333.3 | | 0.9 | 0.7 | 1.3 | 0.8 | -0.4 | -2.7 | -2.1 | -3.6 | -2.3 |
| 111.1 | | 1.6 | 3.5 | 3.7 | 3.7 | -0.3 | -1.1 | -1.0 | -5.1 | -2.5 |
| 37.0 | | 1.2 | 1.5 | 1.0 | 1.5 | -4.3 | -3.1 | -4.2 | -6.0 | -2.3 |
| 12.3 | | 1.6 | 3.7 | 2.8 | 1.7 | 0.7 | -4.3 | 0.4 | -11.7 | -7.5 |
| 4.1 | | -6.4 | -4.4 | -0.2 | -5.6 | -11.0 | -7.4 | -4.9 | -13.9 | -7.2 |
| 1.4 | | -6.7 | -2.9 | -2.5 | -4.8 | -11.9 | -3.7 | 9.7 | -8.3 | -8.1 |

Fig 17A

[P1X+P2X+P3X] + Docetaxel in cell line 'NCI-H1975' on Day #5

Percent Inhibition Relative to Control

| Docetaxel (ng/mL) | [P1X+P2X+P3X] (nM) | | | | | | | | | |
|---|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 63.4 | 63.0 | 66.8 | 59.6 | 41.5 | 22.8 | 7.3 | -1.1 | 0.2 |
| 1000 | 28.6 | 70.0 | 71.2 | 66.5 | 61.4 | 49.9 | 42.4 | 38.2 | 33.7 | 32.5 |
| 333.3 | 33.0 | 73.3 | 70.9 | 68.2 | 64.3 | 54.6 | 46.5 | 33.7 | 36.1 | 35.0 |
| 111.1 | 33.8 | 73.7 | 75.5 | 72.6 | 65.7 | 53.3 | 43.6 | 35.6 | 35.7 | 37.9 |
| 37.0 | 22.2 | 72.1 | 71.4 | 67.7 | 61.1 | 48.7 | 39.8 | 26.5 | 33.4 | 29.8 |
| 12.3 | 11.3 | 70.8 | 69.4 | 65.4 | 55.8 | 41.3 | 30.2 | 26.5 | 21.5 | 16.2 |
| 4.1 | -1.1 | 69.4 | 70.0 | 66.0 | 62.5 | 44.4 | 28.0 | 18.5 | 8.7 | 5.9 |
| 1.4 | -12.6 | 68.7 | 66.6 | 65.0 | 62.4 | 43.8 | 25.7 | 7.7 | -0.8 | 4.0 |

Bliss Independence Score

| Docetaxel (ng/mL) | [P1X+P2X+P3X] (nM) | | | | | | | | | |
|---|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 1000 | | 3.9 | 2.4 | 9.7 | 9.7 | 8.3 | 2.4 | -4.4 | -5.9 | -3.8 |
| 333.3 | | 2.2 | 4.3 | 9.6 | 8.5 | 6.2 | 1.7 | 4.2 | -3.8 | -1.9 |
| 111.1 | | 2.1 | 0.0 | 5.5 | 7.6 | 8.0 | 5.3 | 3.1 | -2.6 | -3.9 |
| 37.0 | | -0.6 | -0.2 | 6.4 | 7.4 | 5.8 | 0.1 | 1.4 | -12.1 | -7.4 |
| 12.3 | | -3.3 | -2.3 | 5.1 | 8.3 | 6.8 | 1.3 | -8.7 | -11.2 | -4.8 |
| 4.1 | | -6.4 | -7.4 | 0.5 | -3.4 | -3.5 | -6.0 | -12.1 | -10.9 | -6.7 |
| 1.4 | | -9.9 | -8.3 | -2.4 | -7.9 | -9.7 | -12.6 | -12.0 | -13.1 | -16.4 |

Percent Inhibition Relative to Control

[P1X+P2X+P3X] + Docetaxel in cell line 'NCI-H226' on Day #5

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 17.1 | 14.4 | 11.3 | 4.9 | 8.2 | 8.5 | 0.0 | 4.3 | 3.9 |
| 1000 | -48.5 | -22.1 | 11.1 | -21.0 | -18.4 | -4.1 | -27.3 | -23.8 | -18.9 | -47.8 |
| 333.3 | -35.4 | -22.0 | -24.2 | -12.8 | -12.5 | 3.9 | -13.4 | -26.4 | -18.0 | -10.8 |
| 111.1 | -19.8 | 11.7 | -11.2 | 16.1 | -23.8 | -20.3 | -29.1 | -41.4 | -16.1 | -36.9 |
| 37.0 | -27.0 | -17.6 | -10.8 | -23.5 | -10.2 | -2.5 | -12.5 | -33.2 | -8.6 | -18.8 |
| 12.3 | 3.2 | -11.2 | 18.4 | 3.6 | 7.2 | 0.3 | 14.3 | -28.4 | -20.3 | -23.2 |
| 4.1 | -32.9 | 12.0 | -2.6 | -3.4 | -15.6 | -33.2 | -6.3 | -15.2 | -16.3 | -11.4 |
| 1.4 | -22.7 | 11.9 | 19.3 | 26.9 | 19.3 | 27.5 | 21.0 | -2.0 | 10.0 | -7.2 |

Bliss Independence Score

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 1000 | | -0.9 | -38.2 | -10.7 | -22.9 | -32.3 | -8.6 | -24.7 | -23.2 | 5.1 |
| 333.3 | | 9.8 | 8.3 | -7.3 | -16.4 | -28.3 | -10.6 | -9.0 | -11.6 | -19.4 |
| 111.1 | | -11.0 | 8.7 | -22.4 | 9.8 | 10.3 | 19.4 | 21.6 | 1.4 | 21.8 |
| 37.0 | | 12.3 | 2.0 | 10.8 | -10.7 | -14.1 | -3.7 | 6.1 | -12.9 | -3.3 |
| 12.3 | | 31.0 | -1.3 | 10.4 | 0.7 | 10.8 | -2.9 | 31.5 | 27.7 | 30.2 |
| 4.1 | | -22.1 | -11.1 | -14.5 | -10.8 | 11.2 | -15.3 | -17.7 | -10.9 | -16.3 |
| 1.4 | | -13.5 | -24.3 | -35.7 | -36.0 | -40.2 | -33.3 | -20.7 | -27.4 | -10.7 |

[P1X+P2X+P3X] + Docetaxel in cell line 'NCI-H322M' on Day #5

Percent Inhibition Relative to Control

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 75.6 | 75.4 | 72.2 | 59.2 | 41.0 | 27.4 | 25.4 | 25.1 | 25.3 |
| 1000 | 38.3 | 79.8 | 80.5 | 78.1 | 73.5 | 64.8 | 57.3 | 51.6 | 51.8 | 50.6 |
| 333.3 | 38.4 | 80.9 | 79.3 | 84.3 | 72.2 | 64.0 | 58.0 | 52.4 | 57.2 | 54.2 |
| 111.1 | 31.4 | 80.0 | 79.5 | 75.6 | 70.0 | 59.3 | 54.1 | 53.6 | 50.1 | 49.9 |
| 37.0 | 8.9 | 77.6 | 76.4 | 74.7 | 64.6 | 44.1 | 34.7 | 30.2 | 34.3 | 28.6 |
| 12.3 | 4.6 | 76.7 | 74.9 | 71.5 | 62.2 | 44.8 | 34.4 | 31.2 | 28.0 | 32.7 |
| 4.1 | -3.8 | 75.6 | 75.2 | 72.9 | 62.8 | 47.8 | 35.4 | 24.3 | 26.9 | 27.5 |
| 1.4 | -2.0 | 75.8 | 75.3 | 74.9 | 64.8 | 47.4 | 35.3 | 28.1 | 26.2 | 29.4 |

Bliss Independence Score

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 1000 | | 5.1 | 4.3 | 4.7 | 1.3 | -1.2 | -2.1 | 2.4 | 2.0 | 3.3 |
| 333.3 | | 4.1 | 5.5 | -1.4 | 2.7 | -0.3 | -2.7 | 1.6 | -3.3 | -0.2 |
| 111.1 | | 3.3 | 3.6 | 5.3 | 2.0 | 0.2 | -3.9 | -4.8 | -1.5 | -1.1 |
| 37.0 | | 0.2 | 1.2 | 0.0 | -1.8 | 2.2 | -0.8 | 1.8 | -2.5 | 3.3 |
| 12.3 | | 0.0 | 1.6 | 2.0 | -1.1 | -1.1 | -3.7 | -2.4 | 0.5 | -4.0 |
| 4.1 | | -0.9 | -0.7 | -1.8 | -5.2 | -9.0 | -10.8 | -1.7 | -4.6 | -5.0 |
| 1.4 | | -0.7 | -0.4 | -3.3 | -6.4 | -7.6 | -9.4 | -4.2 | -2.6 | -5.6 |

[P1X+P2X+P3X] + Docetaxel in cell line 'HCC827' on Day #5

Percent Inhibition Relative to Control

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 74.0 | 75.9 | 67.4 | 48.6 | 22.5 | 12.8 | -1.2 | -1.2 | -0.4 |
| 1000 | 79.4 | 89.6 | 90.2 | 89.0 | 83.6 | 82.3 | 82.3 | 84.2 | 81.7 | 84.1 |
| 333.3 | 81.5 | 90.1 | 89.7 | 88.9 | 84.7 | 84.7 | 88.5 | 83.4 | 83.8 | 82.6 |
| 111.1 | 82.7 | 90.4 | 89.7 | 88.6 | 83.8 | 82.0 | 83.2 | 83.8 | 86.4 | 81.9 |
| 37.0 | 72.6 | 84.9 | 85.8 | 81.0 | 70.4 | 64.1 | 63.9 | 64.5 | 63.4 | 64.1 |
| 12.3 | 18.3 | 77.4 | 79.3 | 72.0 | 56.7 | 42.1 | 26.4 | 25.8 | 21.9 | 23.5 |
| 4.1 | 2.8 | 74.0 | 76.0 | 72.0 | 52.1 | 30.3 | 17.6 | 9.3 | 8.1 | 3.3 |
| 1.4 | -7.8 | 76.0 | 74.3 | 71.2 | 49.4 | 29.3 | 14.7 | 4.5 | -3.9 | -3.2 |

Bliss Independence Score

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 1000 | | 5.0 | 4.8 | 4.3 | 5.8 | 1.7 | -0.3 | -5.0 | -2.5 | -4.8 |
| 333.3 | | 5.1 | 5.8 | 5.1 | 5.8 | 1.0 | -4.6 | -2.1 | -2.5 | -1.2 |
| 111.1 | | 5.1 | 6.1 | 5.8 | 7.3 | 4.6 | 1.7 | -1.3 | -3.9 | 0.7 |
| 37.0 | | 8.0 | 7.6 | 10.1 | 15.5 | 14.7 | 12.2 | 7.8 | 8.9 | 8.4 |
| 12.3 | | 1.4 | 1.0 | 1.4 | 1.3 | -5.4 | 2.4 | -8.5 | -4.6 | -5.5 |
| 4.1 | | 0.7 | 0.6 | -3.7 | -2.1 | -5.6 | -2.4 | -7.7 | -6.5 | -0.9 |
| 1.4 | | -4.0 | -0.3 | -6.3 | -4.8 | -12.8 | -8.7 | -13.6 | -5.2 | -5.0 |

[P1X+P2X+P3X] + Docetaxel in cell line 'HOP-62' on Day #5

Percent Inhibition Relative to Control

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 41.1 | 36.0 | 39.1 | 35.7 | 30.3 | 21.9 | 18.2 | 16.0 | 15.4 |
| 1000 | 36.9 | 56.1 | 53.0 | 53.3 | 53.1 | 53.7 | 50.4 | 46.2 | 43.9 | 42.8 |
| 333.3 | 40.4 | 55.7 | 54.7 | 53.9 | 55.8 | 56.9 | 50.7 | 50.3 | 47.1 | 45.6 |
| 111.1 | 34.2 | 53.3 | 50.4 | 48.0 | 47.4 | 48.4 | 43.6 | 44.1 | 42.1 | 40.1 |
| 37.0 | 22.4 | 53.3 | 45.8 | 46.0 | 48.1 | 45.8 | 41.2 | 35.7 | 29.6 | 27.2 |
| 12.3 | 18.4 | 52.4 | 51.5 | 47.9 | 45.3 | 44.4 | 33.4 | 25.3 | 22.0 | 21.7 |
| 4.1 | -11.9 | 42.9 | 43.8 | 46.5 | 43.3 | 30.3 | 26.3 | 22.3 | 11.5 | 14.8 |
| 1.4 | -12.1 | 34.3 | 37.5 | 39.2 | 39.2 | 27.3 | 19.7 | 7.5 | -1.3 | 8.5 |

Bliss Independence Score

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 1000 | | 6.8 | 6.7 | 8.3 | 6.3 | 2.3 | 0.4 | 2.2 | 3.1 | 3.9 |
| 333.3 | | 9.2 | 7.2 | 9.9 | 5.9 | 1.6 | 2.8 | 1.0 | 2.9 | 4.0 |
| 111.1 | | 7.9 | 7.4 | 11.9 | 10.2 | 5.7 | 5.0 | 2.0 | 2.6 | 4.2 |
| 37.0 | | 1.0 | 4.6 | 6.8 | 2.0 | 0.1 | -1.8 | 0.9 | 5.3 | 7.2 |
| 12.3 | | -0.5 | -3.8 | 2.4 | 2.2 | -1.3 | 2.8 | 7.9 | 9.4 | 9.2 |
| 4.1 | | -8.9 | -15.3 | -14.6 | -15.3 | -8.3 | -13.7 | -13.8 | -5.4 | -9.4 |
| 1.4 | | -0.4 | -9.2 | -7.4 | -11.3 | -5.4 | -7.2 | 0.8 | 7.2 | -3.3 |

[P1X+P2X+P3X] + Docetaxel in cell line 'SK-MES-1' on Day #5

Percent Inhibition Relative to Control

| Docetaxel (ng/mL) | [P1X+P2X+P3X] (nM) | | | | | | | | | |
|---|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 58.7 | 51.8 | 46.1 | 39.4 | 29.7 | 6.9 | -5.1 | -7.5 | -5.8 |
| 1000 | 62.6 | 83.4 | 83.1 | 83.5 | 79.8 | 77.7 | 73.7 | 67.8 | 63.9 | 61.8 |
| 333.3 | 59.4 | 80.1 | 82.3 | 80.7 | 79.2 | 76.7 | 70.5 | 65.6 | 62.2 | 61.9 |
| 111.1 | 45.1 | 81.0 | 79.3 | 78.8 | 75.7 | 74.4 | 66.2 | 59.5 | 54.5 | 57.2 |
| 37.0 | 23.5 | 74.0 | 66.6 | 62.6 | 58.0 | 55.1 | 45.9 | 32.5 | 28.7 | 30.8 |
| 12.3 | 4.8 | 62.0 | 42.1 | 59.6 | 48.5 | 46.3 | 31.7 | 18.2 | 1.8 | 2.2 |
| 4.1 | -8.2 | 55.5 | 53.3 | 49.0 | 42.7 | 41.3 | 21.6 | 10.6 | -3.6 | -0.5 |
| 1.4 | -4.8 | 60.7 | 54.1 | 50.1 | 50.3 | 37.3 | 24.0 | 15.6 | 1.6 | 1.9 |

Bliss Independence Score

| Docetaxel (ng/mL) | [P1X+P2X+P3X] (nM) | | | | | | | | | |
|---|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 1000 | | *1.2* | -1.1 | -3.7 | -2.5 | -4.0 | -8.5 | -7.1 | -4.1 | -1.4 |
| 333.3 | | *3.1* | -1.9 | -2.6 | -3.8 | -5.2 | -8.3 | -8.3 | -5.8 | -4.9 |
| 111.1 | | -3.7 | -5.8 | -8.4 | -9.0 | -13.0 | -17.3 | -17.2 | -13.5 | -15.3 |
| 37.0 | | -5.6 | -3.5 | -3.8 | -4.4 | -8.9 | -17.1 | -12.9 | -10.9 | -11.7 |
| 12.3 | | -1.3 | *12.0* | -10.9 | -6.2 | -13.2 | -20.3 | -18.3 | -4.1 | -2.9 |
| 4.1 | | -0.2 | -5.5 | -7.3 | -8.3 | -17.4 | -22.3 | -24.3 | -12.7 | -14.0 |
| 1.4 | | -4.0 | -4.6 | -6.6 | -13.8 | -11.0 | -21.6 | -25.7 | -14.3 | -12.8 |

[P1X+P2X+P3X] + Docetaxel in cell line 'SW 900' on Day #5

Percent Inhibition Relative to Control

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | 0.0 | 40.2 | 27.0 | 36.4 | 40.8 | 38.8 | 40.5 | 40.4 | 21.8 | 4.5 |
| 1000 | 9.6 | 47.1 | 44.4 | 42.8 | 48.4 | 42.0 | 41.6 | 33.8 | 34.3 | 22.1 |
| 333.3 | 16.0 | 52.0 | 45.5 | 49.7 | 46.4 | 44.1 | 44.8 | 34.0 | 35.1 | 18.7 |
| 111.1 | 16.6 | 47.1 | 51.7 | 52.4 | 47.9 | 47.0 | 48.2 | 36.7 | 33.4 | 23.0 |
| 37.0 | 11.0 | 49.4 | 51.1 | 48.4 | 47.0 | 47.7 | 43.8 | 35.9 | 34.2 | 20.3 |
| 12.3 | 12.4 | 37.3 | 34.7 | 35.3 | 48.7 | 48.2 | 38.9 | 29.5 | 15.2 | 12.9 |
| 4.1 | -14.8 | 37.4 | 35.4 | 39.5 | 40.3 | 35.2 | 33.4 | 21.0 | 7.1 | 4.1 |
| 1.4 | -14.3 | 37.1 | 43.1 | 38.1 | 35.3 | 38.2 | 42.3 | 29.6 | 17.0 | 6.8 |

Bliss Independence Score

| Docetaxel (ng/mL) | [P1X+P2X+P3X] (nM) | | | | | | | | |
|---|---|---|---|---|---|---|---|---|---|
| | 0.0 | 2000 | 666.7 | 222.2 | 74.1 | 24.7 | 8.2 | 2.7 | 0.9 | 0.3 |
| 0.0 | | | | | | | | | | |
| 1000 | | -1.2 | -10.4 | -0.3 | -2.0 | 2.6 | 4.6 | 12.3 | -5.0 | -8.5 |
| 333.3 | | -2.3 | -6.8 | -3.1 | 3.8 | 4.5 | 5.2 | 15.9 | -0.8 | 1.1 |
| 111.1 | | 3.0 | -12.6 | -5.4 | 2.7 | 2.0 | 2.1 | 13.5 | 1.4 | -2.6 |
| 37.0 | | -2.6 | -16.0 | -5.0 | 0.3 | -2.2 | 3.3 | 11.0 | -3.7 | -5.2 |
| 12.3 | | 10.3 | 1.4 | 9.0 | -0.6 | -1.9 | 9.0 | 18.2 | 16.3 | 3.5 |
| 4.1 | | -6.1 | -19.2 | -12.5 | -8.3 | -5.5 | -1.7 | 10.5 | 3.1 | -13.7 |
| 1.4 | | -5.5 | -26.5 | -10.8 | -3.1 | -8.2 | -10.3 | 2.2 | -6.4 | -15.9 |

Fig 17H

[P1X+P2X+P3X] + SN-38 in cell line 'A549' on Day #3

Percent Inhibition Relative to Control

| [P1X+P2X+P3X] (nM) \ SN-38 (nM) | 0.00 | 1000 | 250.0 | 62.50 | 15.60 | 3.90 | 0.98 | 0.24 | 0.06 | 0.02 |
|---|---|---|---|---|---|---|---|---|---|---|
| 0.00 | 0.0 | 80.0 | 72.6 | 58.5 | 27.1 | 16.0 | 9.5 | 13.8 | 11.5 | 13.1 |
| 1000 | 69.9 | 89.3 | 87.6 | 83.6 | 75.8 | 74.0 | 72.4 | 72.4 | 73.2 | 73.1 |
| 250.0 | 73.5 | 90.0 | 88.0 | 85.4 | 78.5 | 77.0 | 75.4 | 76.0 | 75.3 | 74.6 |
| 62.50 | 72.4 | 89.5 | 88.2 | 86.0 | 78.1 | 76.8 | 72.7 | 74.7 | 74.8 | 74.2 |
| 15.60 | 67.2 | 88.6 | 86.6 | 83.7 | 75.3 | 71.5 | 69.3 | 70.0 | 70.4 | 70.0 |
| 3.90 | 57.4 | 86.6 | 83.1 | 80.5 | 66.5 | 61.8 | 60.8 | 58.9 | 60.9 | 58.2 |
| 0.98 | 28.6 | 84.7 | 78.2 | 72.5 | 53.7 | 36.9 | 40.1 | 37.5 | 40.2 | 37.8 |
| 0.24 | 7.2 | 82.2 | 75.4 | 63.3 | 36.1 | 24.5 | 20.4 | 22.8 | 19.8 | 22.5 |

Bliss Independence Score

| [P1X+P2X+P3X] (nM) \ SN-38 (nM) | 0.00 | 1000 | 250.0 | 62.50 | 15.60 | 3.90 | 0.98 | 0.24 | 0.06 | 0.02 |
|---|---|---|---|---|---|---|---|---|---|---|
| 0.00 | | | | | | | | | | |
| 1000 | | 4.7 | 4.1 | 3.9 | 2.2 | 0.7 | 0.3 | 1.7 | 0.1 | 0.7 |
| 250.0 | | 4.7 | 4.7 | 3.6 | 2.2 | 0.7 | 0.6 | 1.1 | 1.2 | 2.4 |
| 62.50 | | 5.0 | 4.2 | 2.5 | 1.8 | 0.0 | 2.3 | 1.5 | 0.7 | 1.8 |
| 15.60 | | 4.8 | 4.4 | 2.7 | 0.8 | 1.0 | 1.0 | 1.7 | 0.6 | 1.5 |
| 3.90 | | 4.8 | 5.2 | 1.8 | 2.4 | 2.5 | 0.6 | 4.3 | 1.5 | 4.8 |
| 0.98 | | 1.0 | 2.3 | -2.2 | -5.8 | 3.2 | -4.7 | 0.9 | -3.4 | 0.0 |
| 0.24 | | -0.8 | -0.9 | -1.8 | -3.8 | -2.4 | -4.4 | -2.7 | -1.9 | -3.2 |

Fig 18A

[P1X+P2X+P3X] + SN-38 in cell line 'HCT 116' on Day #3

Percent Inhibition Relative to Control

| SN-38 (nM) | [P1X+P2X+P3X] (nM) | | | | | | |
|---|---|---|---|---|---|---|---|
| | 0.0 | 2000 | 500.0 | 250.0 | 125.0 | 62.5 | |
| 0.0 | 0.0 | 5.8 | 5.4 | 5.4 | 16.0 | 3.5 | |
| 1000 | 93.5 | 93.3 | 93.3 | 93.1 | 82.6 | 93.6 | |
| 250.0 | 87.4 | 89.0 | 89.7 | 89.1 | 88.9 | 89.6 | |
| 62.5 | 75.9 | 79.0 | 79.6 | 79.6 | 79.4 | 78.1 | |
| 15.0 | 60.4 | 66.9 | 61.2 | 66.1 | 66.0 | 66.4 | |
| 3.9 | 49.5 | 54.5 | 55.9 | 56.0 | 56.5 | 53.3 | |
| 1.0 | 29.5 | 39.3 | 40.7 | 38.4 | 37.4 | 34.6 | |
| 0.2 | 6.8 | 12.1 | 14.9 | 11.8 | 14.5 | 9.7 | |

Bliss Independence Score

| SN-38 (nM) | [P1X+P2X+P3X] (nM) | | | | | | |
|---|---|---|---|---|---|---|---|
| | 0.0 | 2000 | 500.0 | 250.0 | 125.0 | 62.5 | |
| 0.0 | | | | | | | |
| 1000 | | 0.6 | 0.6 | 0.7 | 11.9 | 0.1 | |
| 250.0 | | -0.9 | -1.6 | -1.0 | 0.5 | -1.8 | |
| 62.5 | | -1.6 | -2.4 | -2.4 | 0.4 | -1.3 | |
| 15.0 | | -4.2 | 1.3 | -3.6 | 0.7 | -4.6 | |
| 3.9 | | -2.1 | -3.7 | -3.8 | 1.1 | -2.1 | |
| 1.0 | | -5.7 | -7.4 | -5.1 | 3.5 | -2.7 | |
| 0.2 | | 0.1 | -3.1 | 0.0 | 7.3 | 0.3 | |

Fig 18B

[P1X+P2X+P3X] + SN-38 in cell line 'HT-29' on Day #3

Percent Inhibition Relative to Control

| | | [P1X+P2X+P3X] (nM) | | | | | |
|---|---|---|---|---|---|---|---|
| | | 0.0 | 2000 | 500.0 | 250.0 | 125.0 | 62.5 |
| SN-38 (nM) | 0.0 | 0.0 | 9.9 | 17.0 | 12.2 | 17.5 | 15.9 |
| | 1000 | 82.3 | 81.4 | 82.0 | 80.7 | 81.4 | 81.6 |
| | 250.0 | 77.9 | 78.0 | 79.0 | 78.6 | 77.4 | 77.8 |
| | 62.5 | 56.9 | 63.1 | 63.3 | 60.6 | 60.6 | 57.4 |
| | 15.0 | 16.2 | 35.4 | 34.2 | 33.4 | 30.1 | 34.4 |
| | 3.9 | 20.5 | 33.5 | 34.7 | 34.1 | 30.7 | 29.8 |
| | 1.0 | 6.7 | 21.0 | 22.9 | 20.0 | 18.2 | 18.9 |
| | 0.2 | 5.5 | 8.5 | 15.4 | 9.3 | 12.2 | 8.2 |

Bliss Independence Score

| | | [P1X+P2X+P3X] (nM) | | | | | |
|---|---|---|---|---|---|---|---|
| | | 0.0 | 2000 | 500.0 | 250.0 | 125.0 | 62.5 |
| SN-38 (nM) | 0.0 | | | | | | |
| | 1000 | | 2.6 | 3.3 | 3.7 | 4.0 | 3.5 |
| | 250.0 | | 2.0 | 2.6 | 2.0 | 4.3 | 3.5 |
| | 62.5 | | -1.9 | 0.9 | 1.6 | 3.8 | 6.3 |
| | 15.0 | | -10.9 | -3.7 | -6.9 | 0.8 | -4.9 |
| | 3.9 | | -5.1 | -0.7 | -3.9 | 3.6 | 3.2 |
| | 1.0 | | -5.0 | -0.3 | -1.9 | 4.8 | 2.6 |
| | 0.2 | | 6.5 | 6.2 | 7.8 | 9.8 | 12.3 |

Percent Inhibition Relative to Control

[P1X+P2X+P3X] + SN-38 in cell line 'LoVo' on Day #3

| [P1X+P2X+P3X] (nM) | SN-38 (nM) | | | | | | | | |
|---|---|---|---|---|---|---|---|---|---|
| | 0.00 | 1000 | 250.0 | 62.50 | 15.60 | 3.90 | 0.98 | 0.24 | 0.06 | 0.02 |
| 0.00 | 0.0 | 90.7 | 82.3 | 39.0 | -0.8 | -2.1 | -1.9 | -1.0 | -0.8 | -1.8 |
| 1000 | 32.3 | 96.8 | 92.2 | 61.6 | 30.0 | 27.5 | 32.5 | 32.2 | 30.7 | 34.6 |
| 250.0 | 25.5 | 97.0 | 92.2 | 60.7 | 33.8 | 32.2 | 30.2 | 26.7 | 30.8 | 33.3 |
| 62.50 | 25.8 | 96.7 | 91.7 | 61.7 | 31.5 | 26.1 | 25.3 | 27.8 | 27.1 | 29.7 |
| 15.60 | 14.2 | 96.2 | 90.2 | 54.3 | 25.6 | 19.3 | 19.1 | 16.9 | 15.6 | 17.5 |
| 3.90 | 8.2 | 94.8 | 86.5 | 45.9 | 15.6 | 7.1 | 3.8 | 11.8 | 10.0 | 11.7 |
| 0.98 | 4.5 | 91.5 | 82.2 | 45.4 | 14.6 | 7.5 | 5.2 | 5.0 | 6.8 | 6.2 |
| 0.24 | -3.8 | 90.8 | 82.3 | 41.3 | 10.0 | 0.3 | -2.6 | 0.6 | 2.1 | 3.4 |

Bliss Independence Score

| [P1X+P2X+P3X] (nM) | SN-38 (nM) | | | | | | | | |
|---|---|---|---|---|---|---|---|---|---|
| | 0.00 | 1000 | 250.0 | 62.50 | 15.60 | 3.90 | 0.98 | 0.24 | 0.06 | 0.02 |
| 0.00 | | | | | | | | | | |
| 1000 | | -3.1 | -4.2 | -2.9 | 1.7 | 3.3 | -1.6 | -0.6 | 1.0 | -3.5 |
| 250.0 | | -3.9 | -5.4 | -6.1 | -8.8 | -8.3 | -6.1 | -1.9 | -5.9 | -9.1 |
| 62.50 | | -3.6 | -4.8 | -7.0 | -6.4 | -1.9 | -1.0 | -2.8 | -1.9 | -5.3 |
| 15.60 | | -4.1 | -5.4 | -6.6 | -12.1 | -6.9 | -6.5 | -3.5 | -2.1 | -4.8 |
| 3.90 | | -3.3 | -2.8 | -1.9 | -8.1 | -0.7 | 2.6 | -4.5 | -2.5 | -5.1 |
| 0.98 | | -0.4 | 0.8 | -3.7 | -10.9 | -4.9 | -2.5 | -1.5 | -3.1 | -3.4 |
| 0.24 | | -0.4 | -0.7 | -4.7 | -14.6 | -6.3 | -3.2 | -5.5 | -6.8 | -9.1 |

ANTIBODIES AGAINST EPIDERMAL GROWTH FACTOR RECEPTOR (EGFR) AND USES THEREOF

RELATED APPLICATIONS

This application is a continuation of U.S. application Ser. No. 14/147,331, filed on Jan. 3, 2014, which is a continuation-in-part of International Application No. PCT/US2012/045235, filed on Jul. 2, 2012, which claims priority to U.S. Application No. 61/504,633, filed on Jul. 5, 2011, and U.S. Application No. 61/558,945, filed on Nov. 11, 2011. The contents of the aforementioned applications are hereby incorporated by reference.

BACKGROUND

The natural immune system has evolved to make antibodies for efficient neutralization of pathogens. Natural antibody preparations isolated from immunized animals are polyclonal in origin, and exhibit immunodominance as compared to individual antibodies, which are restricted to one or a few epitopes of a particular antigen. Anti-tumor antibodies are able to block growth or kill tumor cells to which they bind have been developed as highly effective cancer therapeutic agents. Mixtures of anti-tumor antibodies may achieve tumor suppressive effects that are greater than achieved by any individual antibody in the mixture Such results have been achieved by combining two or more neutralizing antibodies against the epidermal growth factor receptor, EGFR (ErbB1). Antibodies that bind to and inhibit EGFR have proven to provide useful anti-cancer benefits and are of great medical and commercial value. Particular combinations of pairs of antagonistic, yet non-competitive, anti-EGFR antibodies resulted in downregulation of EGFR which was faster and more effective than application of either antibody alone (Friedman et al. (2005) PNAS 102:1915-1920). The combination of two cross-competitive (i.e., competitive with each other for binding to antigen) anti-EGFR antibodies has shown to be non-synergistic. It is possible that binding of a plurality of antibodies to distinct epitopes of EGFR forms lattices of complexed receptors on cell surfaces, leading to more efficient internalization and degradation than obtained with antibodies targeting a single epitope. The combination of a particular pair of anti-EGFR receptor antibodies have also been reported to result in additive and in some cases synergistic, antitumor activity in vivo (Perera et al. (2005) Clin Cancer Res 11:6390-6399). Monoclonal antibody 806, raised against the mutant de2-7 EGFR, combined with antagonistic antibody 528 displayed significantly higher anti-tumor activity in a glioma xenograft model than treatment with either antibody alone. The mechanism of the synergistic anti-tumor activity was shown to be associated with rapid downregulation of EGFR, which was not induced by treatment with the individual antibodies. Similarly EGFR phosphorylation was greatly reduced in the presence of another pair of anti-EGFR antibodies, cetuximab and EMD55900 (Kamat et al. (2008) Cancer Biol Ther 7:726-33).

Certain combinations of antibodies targeting the related receptor, ErbB2, have also been shown to function in synergy (Friedman et al. (2005). Trastuzumab combined with pertuzumab inhibited the survival of BT474 breast cancer cells at doses in which individual antibodies are ineffective (Nahta et al. (2004) Cancer Res 64:2343-2346). In another study three non-competitive anti-ErbB2 antibodies demonstrated far more effective in vitro killing of BT474 cells in combination than individually and similar results were obtained in a BT474 in vivo xenograft model (Spiridon et al. (2002) Clin Cancer Res 8:1699-701).

Other evidence that combining more than one antibody may enhance the growth suppressive (e.g., cytotoxic) effect of antibodies on tumor cells has been reported. For example, monoclonal antibodies to the tumor antigen 17-1A were combined, tumor cell lysis was studied, and it was found that monoclonal antibodies, as well as combinations of competing antibodies, were ineffective, whereas combinations of two or more non-competing antibodies resulted in complete tumor cell lysis.

In addition to combining antibodies, higher antibody potency has also been achieved by increasing the antigen affinity of recombinantly expressed anti-tumor antibodies through recombinant DNA techniques known as affinity maturation.

Accordingly, additional approaches and methods for producing anti-tumor antibody action so as to enhance the responsiveness of tumors to anti-EGFR antibodies and antibody combinations are still needed, including anti-EGFR antibodies with higher tumor affinity and combinations of such high-affinity anti-EGFR antibodies that enhance signaling inhibition and provide more effective cytostatic or cytotoxic anti-tumor outcomes.

SUMMARY

Novel monoclonal antibodies that bind to EGFR and inhibit various EGFR functions are provided herein. These antibodies provide useful therapeutic effects, and when combined with each other or with other anti-ErbB receptor antibodies (e.g., other anti-EGFR antibodies), are capable of exhibiting a synergistic or additive therapeutic effect compared to the administration of each antibody alone. These antibodies, when administered individually or in combinations as herein provided, are useful for treating a variety of disorders (e.g., cancers) associated with EGFR-mediated cellular signaling. Accordingly, isolated novel monoclonal antibodies that exhibit the properties of binding to EGFR and inhibiting various EGFR functions, and combinations of such antibodies that exhibit such properties are also provided herein. Uses of these antibodies for diagnostic and therapeutic purposes are also provided, as are uses of the antibodies and antibody combinations herein disclosed.

In one embodiment, a monoclonal antibody is provided which binds EGFR extracellular domain and comprises heavy and light chain CDR1, CDR2, and CDR3, sequences, wherein the heavy and light chain CDR1, CDR2, and CDR3, sequences are selected from the group consisting of:

(a) heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively;

(b) heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively; and (c) heavy chain CDR1, CDR2, and CDR3 sequences of SEQ ID NOs: 13, 14, and 15, respectively, and light chain CDR1, CDR2, and CDR3 sequences of SEQ ID NOs: 16, 17, and 18, respectively.

In another embodiment, a monoclonal antibody is provided that binds to EGFR extracellular domain and comprises a heavy chain variable region and a light chain variable region, wherein the heavy and light chain variable region sequences are selected from the group consisting of:

(a) a heavy chain variable region comprising SEQ ID NO: 19 and a light chain variable region comprising SEQ ID NO: 20;

(b) a heavy chain variable region comprising SEQ ID NO: 21 and a light chain variable region comprising SEQ ID NO: 22; and (c) a heavy chain variable region comprising SEQ ID NO: 23 and a light chain variable region comprising SEQ ID NO: 24.

The aforementioned monoclonal antibodies can bind to EGFR with a $K_D$ of, for example, better than 100 nM, or better than 10 nM, or better than 1 nM, or better than 100 pM, or better than 10 pM, or better than 1 pM. The monoclonal antibodies can exhibit one or more of the functional properties disclosed herein. The monoclonal antibody can be, for example, a human antibody. In other embodiments, the antibody can be a bispecific antibody, immunoconjugate, Fab, Fab'2, ScFv, Affibody®, avimer, nanobody or a domain antibody. In other embodiments, the monoclonal antibody can be, e.g., an IgG1, IgG2, IgG3, IgG4, IgM, IgA1, IgA2, IgAsec, IgD, or IgE isotype antibody.

Also provided are pharmaceutical compositions comprising any one or more of the aforementioned anti-EGFR monoclonal antibodies and a pharmaceutically acceptable carrier. Kits are also provided. The kit can comprise, for example, a pharmaceutical composition in a container. Methods of treating cancer in a subject, comprising administering to the subject an effective amount of the pharmaceutical composition comprising any one or more of the aforementioned anti-EGFR monoclonal antibodies are also provided. The aforementioned anti-EGFR monoclonal antibodies or combinations thereof for the treatment of a cancer (or for manufacture of a medicament for the treatment of a cancer) are also provided.

In another embodiment, a composition comprising two or three monoclonal antibodies which bind to EGFR extracellular domain is provided, wherein the two or three monoclonal antibodies are selected from the group consisting of:

(a) a monoclonal antibody comprising heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively;

(b) a monoclonal antibody comprising heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively and (c) a monoclonal antibody comprising heavy chain CDR1, CDR2, and CDR3 sequences of SEQ ID NOs: 13, 14, and 15, respectively, and light chain CDR1, CDR2, and CDR3 sequences of SEQ ID NOs: 16, 17 and 18, respectively; and wherein the composition comprises (a) and (b), (a) and (c), (b) and (c) or (a), (b) and (c).

In yet another embodiment, a composition comprising two or three monoclonal antibodies which bind to EGFR extracellular domain is provided, wherein the two or three monoclonal antibodies are selected from the group consisting of:

(a) a monoclonal antibody comprising a heavy chain variable region comprising SEQ ID NO: 19 and a light chain variable region comprising SEQ ID NO: 20;

(b) a monoclonal antibody comprising a heavy chain variable region comprising SEQ ID NO: 21 and a light chain variable region comprising SEQ ID NO: 22; and (c) a monoclonal antibody comprising a heavy chain variable region comprising SEQ ID NO: 23 and a light chain variable region comprising SEQ ID NO: 24; and wherein the composition comprises (a) and (b), (a) and (c), (b) and (c) or (a) (b) and (c).

Each of monoclonal antibodies (a), (b) and (c) in the aforementioned compositions comprising two or three antibodies can bind to EGFR with a $K_D$ of, for example, better than 100 nM, or better than 10 nM or better than 1 nM. Each of monoclonal antibodies (a), (b) and (c) can exhibit one or more of the functional properties disclosed herein. Each of monoclonal antibodies (a), (b) and (c) can be, for example, a human antibody. In other embodiments, one or more of monoclonal antibodies (a), (b), and (c) is independently selected from the group consisting of a bispecific antibody, immunoconjugate, Fab, Fab'2, ScFv, Affibody®, avimer, nanobody, and a domain antibody. In other embodiments, each of monoclonal antibodies (a), (b), and (c) is independently selected from the group consisting of IgG1, IgG2, IgG3, IgG4, IgM, IgA1, IgA2, IgAsec, IgD and IgE isotype antibodies. Monoclonal antibodies (a), (b) and (c) may also be in the form of IgY and camelid antibodies.

Also provided is a pharmaceutical composition comprising any one of the aforementioned compositions comprising two or three anti-EGFR monoclonal antibodies and a pharmaceutically acceptable carrier. Kits are also provided. The kit can comprise, for example, a pharmaceutical composition in a container. Methods of treating cancer in a subject, comprising administering to the subject an effective amount of the pharmaceutical composition comprising any one of the aforementioned compositions comprising two or three anti-EGFR monoclonal antibodies are also provided. The aforementioned compositions comprising two or three anti-anti-EGFR monoclonal antibodies (and their use for the manufacture of a medicament) for the treatment of a cancer are also provided.

In another embodiment, a composition is provided comprising three monoclonal anti-EGFR antibodies, said composition comprising a first antibody, a second antibody and a third antibody, wherein (i) the first antibody comprises heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively; (ii) the second antibody comprises heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively; and (iii) the third antibody comprises heavy chain CDR1, CDR2, and CDR3 sequences of SEQ ID NOs: 13, 14, and 15 respectively, and light chain CDR1, CDR2, and CDR3 sequences of SEQ ID NOs: 16, 17, and 18, respectively, and wherein the first second and third antibodies are present at a molar ratio of 2:2:1 to each other.

In yet another embodiment, a composition is provided comprising three monoclonal anti-EGFR antibodies, said composition comprising a first antibody, a second antibody and a third antibody, wherein (i) the first antibody comprises a heavy chain variable region comprising SEQ ID NO: 19 and a light chain variable region comprising SEQ ID NO: 20; (ii) the second antibody comprises a heavy chain variable region comprising SEQ ID NO: 21 and a light chain variable region comprising SEQ ID NO: 22; and (iii) the third antibody comprises a heavy chain variable region comprising SEQ ID NO: 23 and a light chain variable region comprising SEQ ID NO: 24, and wherein the first second and third antibodies are present at a molar ratio of 2:2:1 to each other.

Each of the first, second and third antibodies in the aforementioned compositions can bind to EGFR with a $K_D$ of, for example, better than 100 nM, or better than 10 nM or better than 1 nM. In another embodiment, the first antibody binds to EGFR with a $K_D$ in a range of $1\times10^{-9}$ M to $1.1\times10^{-11}$ M, the second antibody binds to EGFR with a $K_D$ in a range of $1\times10^{-9}$ M to $7.0\times10^{-11}$ M and the third antibody binds to EGFR with a $K_D$ in a range of $1\times10^{-9}$ M to $3.6\times10^{-10}$ M. Each of the first, second and third antibodies in the aforementioned compositions can exhibit one or more of the functional properties disclosed herein. Each of the first, second and third antibodies in the aforementioned compositions can be, for example, a human antibody. In other embodiments, one or more of the first antibody, the second antibody and the third antibody is independently selected from the group consisting of a bispecific antibody, immunoconjugate, Fab, Fab'2, ScFv, affibody, avimer, nanobody, and a domain antibody. In other embodiments, each of the first antibody, the second antibody and the third antibody is independently selected from the group consisting of IgG1, IgG2, IgG3, IgG4, IgM, IgA1, IgA2, IgAsec, IgD and IgE isotype antibodies.

Also provided are pharmaceutical compositions comprising any one of the aforementioned anti-EGFR compositions comprising a first antibody, a second antibody and a third antibody at a 2:2:1 ratio, and a pharmaceutically acceptable carrier. In one embodiment, the pharmaceutical composition is a sterile composition. In another embodiment, the pharmaceutical composition is suitable for injection. In yet another embodiment, the pharmaceutical composition is a sterile composition suitable for intravenous injection. Kits are also provided. The kit can comprise, for example, a pharmaceutical composition in a container. Methods of treating cancer in a subject, comprising administering to the subject an effective amount of the pharmaceutical composition comprising any one of the aforementioned anti-EGFR compositions comprising first, second and third antibodies at a 2:2:1 ratio are also provided. Use of any of the aforementioned anti-EGFR compositions comprising first, second and third antibodies at a 2:2:1 ratio for the manufacture of a medicament for the treatment of a cancer are also provided.

In another embodiment, a method of preparing an anti-EGFR antibody composition is provided, the method comprising combining in a single composition:

(a) a monoclonal antibody comprising heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively;

(b) a monoclonal antibody comprising heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively; and (c) a monoclonal antibody comprising heavy chain CDR1, CDR2, and CDR3 sequences of SEQ ID NOs: 13, 14, and 15 respectively, and light chain CDR1, CDR2, and CDR3 sequences of SEQ ID NOs: 16, 17, and 18, respectively;

wherein (a), (b) and (c) are combined at a molar ratio of 2:2:1 to each other.

In another embodiment, a method of preparing an anti-EGFR antibody composition is provided, the method comprising combining in a single composition:

(a) a monoclonal antibody comprising a heavy chain variable region comprising SEQ ID NO: 19 and a light chain variable region comprising SEQ ID NO:20;

(b) a monoclonal antibody comprising a heavy chain variable region comprising SEQ ID NO: 21 and a light chain variable region comprising SEQ ID NO: 22; and (c) a monoclonal antibody comprising a heavy chain variable region comprising SEQ ID NO: 23 and a light chain variable region comprising SEQ ID NO: 24;

wherein (a), (b) and (c) are combined at a molar ratio of 2:2:1 to each other.

In another embodiment, a method of treating a subject with anti-EGFR antibodies is provided, the method comprising administering to the subject:

(a) a monoclonal antibody comprising heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively;

(b) a monoclonal antibody comprising heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively; and (c) a monoclonal antibody comprising heavy chain CDR1, CDR2, and CDR3 sequences of SEQ ID NOs: 13, 14, and 15 respectively, and light chain CDR1, CDR2, and CDR3 sequences of SEQ ID NOs: 16, 17, and 18, respectively;

wherein (a), (b) and (c) are administered to the subject at a molar ratio of 2:2:1 to each other.

In another embodiment, a method of treating a subject with anti-EGFR antibodies is provided, the method comprising administering to the subject:

(a) a monoclonal antibody comprising a heavy chain variable region comprising SEQ ID NO: 19 and a light chain variable region comprising SEQ ID NO:20;

(b) a monoclonal antibody comprising a heavy chain variable region comprising SEQ ID NO: 21 and a light chain variable region comprising SEQ ID NO: 22; and (c) a monoclonal antibody comprising a heavy chain variable region comprising SEQ ID NO: 23 and a light chain variable region comprising SEQ ID NO: 24;

wherein (a), (b) and (c) are administered to the subject at a molar ratio of 2:2:1 to each other. In further embodiments, the method further comprises co-administration to the subject of an effective amount of an additional agent selected from the group consisting of irinotecan, MM-121, and docetaxel.

Other features and advantages of the invention will be apparent from the following detailed description, and from the claims.

BRIEF DESCRIPTION OF THE FIGURES

FIGS. 16A-N each present a set of two tables showing the results of a cell viability assay for cell lines as indicated, demonstrating inhibition of tumor cell proliferation by treatment with combinations of P1X+P2X+P3X antibodies with MM-121 antibody in the presence of EGF and HRG ligands.

FIGS. 17A-H each present a set of two tables showing the results of a cell viability assay for cell lines as indicated, demonstrating inhibition of tumor cell proliferation by treatment with combinations of P1X+P2X+P3X antibodies with docetaxel in the presence of EGF ligand.

FIGS. 18A-D each present a set of two tables showing the results of a cell viability assay for cell lines as indicated, demonstrating inhibition of tumor cell proliferation by treatment with combinations of P1X+P2X+P3X antibodies with SN-38 in the presence of EGF ligand.

DETAILED DESCRIPTION

I. Definitions

Figure 1A:
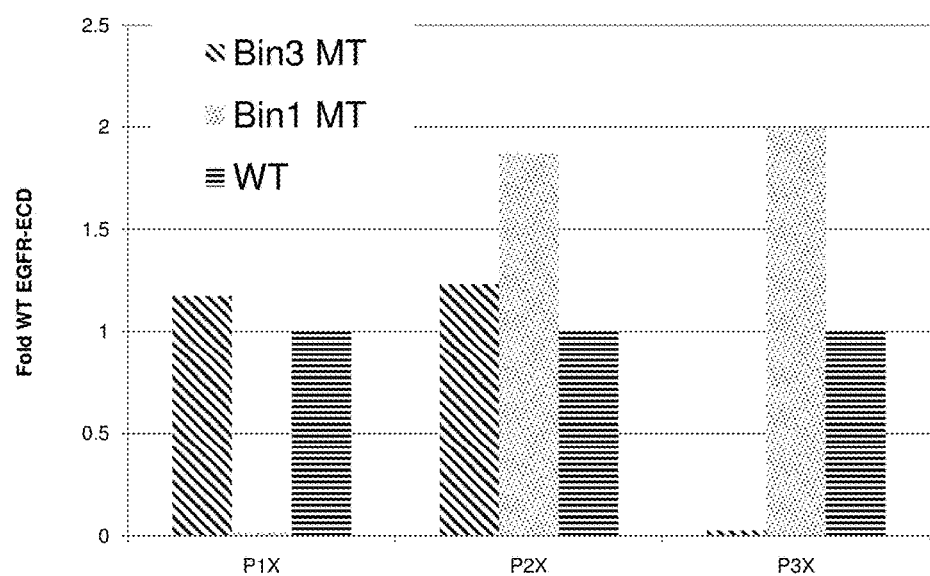
FIG. 1A is a bar graph showing the results of a direct ELISA epitope binning experiment with the P1X, P2X and P3X antibodies using wild-type EGFR-ECD antigen (WT), a Bin 1 epitope mutant (Bin 1 MT) and a Bin 3 epitope mutant (Bin 3 MT).

The terms "EGFR," "ErbB1," and "EGF receptor" are used interchangeably herein to refer to human EGFR protein; see UniProtKB/Swiss-Prot entry P00533. The amino acid sequence of the extracellular domain of human EGFR (EGFR-ECD) is shown in Example 1 and in SEQ ID NO:33.

The term "inhibition" as used herein, refers to any statistically significant decrease in biological activity, including full blocking of the activity. For example, "inhibition" can refer to a statistically significant decrease of about 10%, 20%, 30%, 40%, 50%, 60%, 70%, 80%, 90%, or about 100% in biological activity.

Inhibition of phosphorylation, as used herein, refers to the ability of an antibody to statistically significantly decrease the phosphorylation of a substrate protein relative to the signaling in the absence of the antibody (control). As is known in the art, intracellular signaling pathways include, for example, phosphoinositide 3'-kinase/Akt (PI3K/Akt/PTEN or "AKT") and/or mitogen-activated protein kinase (MAPK/ERK or "ERK") pathways. As is also known in the art, EGFR mediated signaling can be measured by assaying for the level phosphorylation of the substrate (e.g., phosphorylation or no phosphorylation of AKT and/or ERK). Accordingly, in one embodiment, anti-EGFR antibody combinations and compositions provide statistically significant inhibition of the level of phosphorylation of either or both of AKT and ERK by at least 10%, or at least 20%, or at least 30%, or at least 40%, or at least 50%, or at least 60%, or at least 70%, or at least 80%, or at least 90%, or about 100% relative to the level of phosphorylation of AKT and/or ERK in the absence of such antibody (control). Such EGFR mediated signaling can be measured using art recognized techniques which measure a protein in a cellular cascade involving EGFR, e.g., ELISA, western, or multiplex methods, such as Luminex®.

The phrase "inhibition of the growth of cells expressing EGFR," as used herein, refers to the ability of an antibody to statistically significantly decrease the growth of a cell expressing EGFR relative to the growth of the cell in the absence of the antibody (control) either in vivo or in vitro. In one embodiment, the growth of a cell expressing EGFR (e.g., a cancer cell) may be decreased by at least 10%, or at least 20%, or at least 30%, or at least 40%, or at least 50%, or at least 60%, or at least 70%, or at least 80%, or at least 90%, or about 100% when the cells are contacted with an antibody composition of combination disclosed herein, relative to the growth measured in the absence of the antibody composition of combination (control). Cellular growth can be assayed using art recognized techniques which measure the rate of cell division, the fraction of cells within a cell population undergoing cell division, and/or the rate of cell loss from a cell population due to terminal differentiation or cell death (e.g., using a cell titer glow assay or thymidine incorporation).

The phrase "inhibition of an EGFR ligand binding to EGFR," as used herein, refers to the ability of an antibody to statistically significantly decrease the binding of an EGFR ligand to its receptor, EGFR, relative to the EGFR ligand binding in the absence of the antibody (control). This means that, in the presence of the antibody, the amount of the EGFR ligand that binds to EGFR relative to a control (no antibody), is statistically significantly decreased. The amount of an EGFR ligand which binds EGFR may be decreased in the presence of an antibody composition or combination disclosed herein by at least 10%, or at least 20%, or at least 30%, or at least 40%, or at least 50%, or at least 60%, or at least 70%, or at least 80%, or at least 90%, or about 100% relative to the amount in the absence of the antibody (control). A decrease in EGFR ligand binding can be measured using art-recognized techniques that measure the level of binding of labeled EGFR ligand (e.g., radiolabelled EGF or radiolabeled betacellulin) to cells expressing EGFR in the presence or absence (control) of the antibody.

The phrase "inhibition of EGFR dimerization," as used herein, refers to the ability of an antibody to statistically significantly decrease EGFR dimerization (pairing with another ErbB receptor to form homodimers, e.g., ErbB1/ErbB1 pairings, or heterodimers, e.g., ErbB 1/ErbB3 pairings) relative to EGFR dimerization in the absence of the antibody (control). In one embodiment, dimerization of EGFR may be decreased by at least 10%, or at least 20%, or at least 30%, or at least 40%, or at least 50%, or at least 60%, or at least 70%, or at least 80%, or at least 90%, or about 100% when cells expressing EGFR are contacted with an antibody composition or combination disclosed herein, relative to dimerization of EGFR measured in the absence of the antibody (control). A decrease in EGFR dimerization can be measured using art-recognized techniques that measure the level of EGFR dimerization in the presence or absence (control) of the antibody.

The phrase "downregulation of EGFR expression," as used herein, refers to the ability of an antibody to statistically significantly decrease the expression of EGFR on a cell surface, for example, by increasing internalization of EGFR and/or by decreasing recycling of EGFR from intracellular vesicles relative to EGFR expression in the absence of the antibody (control). In one embodiment, expression of EGFR may be decreased by at least 10%, or at least 20%, or at least 30%, or at least 40%, or at least 50%, or at least 60%, or at least 70%, or at least 80%, or at least 90%, or about 100% when cells expressing EGFR are contacted with an antibody composition of combination provided herein, relative to expression of EGFR on the cell surface measured in the absence of the antibody (control). Downregulation of EGFR expression on a cell surface includes, for example, an increase in internalization/recycling of the receptor, and/or an increase in internalization/degradation of the receptor. An increase in EGFR internalization can be measured using art-recognized techniques that measure the level of EGFR internalization in the presence or absence (control) of the antibody.

With respect to combinations of EGFR antibodies (described herein), the words "additive" or "additivity," as used herein, refer to the activity of two or more antibodies wherein their combined activity (relative to a particular function, e.g., inhibition of cell growth) is equal to the sum of their individual activities. That is, the sum of the activities of two or more antibodies provided herein, when acting individually on a cell expressing EGFR, is approximately equivalent to the combined effect of the same antibodies acting together on the same cell. In one embodiment, the additive effect is measured with respect to any of the properties discussed above (e.g., inhibition of AKT or ERK phosphorylation, inhibition of the growth of cells expressing EGFR, etc.). The words "synergy" or "synergistic," as used herein, refer to the activity of two or more antibodies wherein their combined activity (relative to a particular function, e.g., inhibition of cell growth) is greater than the expected additive effect of their individual activities. For example, the expected additive effect can be defined according to Bliss independence criteria. In accordance with the Bliss criteria, the effect of two or more drugs (e.g., antibodies) is equal to the sum of the effects of the individual drugs minus the multiplication of the effects of the individual drugs:

$$E12=E1+E2-E1*E2$$

where E1 is the fractional inhibition by drug 1, E2 is the fractional inhibition by drug 2, and E12 is the expected fractional inhibition by the combination. % inhibition is calculated by multiplying fractional inhibition by 100%. A Bliss independence score is calculated by subtraction of the observed % inhibition from the calculated E12% inhibition:

$$\text{Bliss independence score}=(E12-\text{fraction inhibition observed})*100\%$$

The synergistic effect can apply to any of the properties discussed herein (e.g., inhibition of EGFR-dependant AKT or ERK phosphorylation, inhibition of the growth of cells expressing EGFR, etc.). In a particular embodiment, at least 10%, or at least 20%, or at least 30%, or at least 40%, or at least 50%, or at least 60%, or at least 70%, or at least 80%, or at least 90%, or greater increase in activity of the combined antibodies relative to the additive effect of their individual activities is achieved.

HSA indicates highest single agent. As used herein, HSA refers to a criterion in which the activity of a combination of two drugs (e.g. antibodies) is compared to the higher of the two individual activities of the two drugs when used as single agents at the same doses as used in the combination. A combination of drugs is assigned an HSA score of "True" if the observed activity of the combination is greater than the higher activity of either of the two single drugs and "False" if otherwise. The HSA can be measured for any of the properties discussed herein (e.g., inhibition of EGFR-dependent AKT or ERK phosphorylation, inhibition of the growth of cells expressing EGFR, etc.).

The definitions of the terms "additive," "additivity," "synergy," "synergistic," and "HSA," as described above, also apply to a combination comprised of a combination of EGFR antibodies and another drug (e.g. a chemotherapeutic agent, an antibody with specificity for a protein other than EGFR, etc.) with the following modification: the activity of the combination of EGFR antibodies is treated as a singular drug (e.g. "drug 1").

The term "antibody" or "immunoglobulin," as used interchangeably herein, includes whole antibodies and any antigen binding fragment (antigen-binding portion) or single chain cognates thereof. An "antibody" comprises at least one heavy (H) chain and one light (L) chain. In naturally occurring IgGs, for example, these heavy and light chains are inter-connected by disulfide bonds and there are two paired heavy and light chains, these two also inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR) or Joining (J) regions (JH or JL in heavy and light chains respectively). Each $V_H$ and $V_L$ is composed of three CDRs three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (Clq) of the classical complement system. Thus one or more fragments of an antibody that retain the ability to specifically bind to an antigen (e.g., EGFR) may be used in the combinations disclosed herein. It has been shown that fragments of a full-length antibody can perform the antigen-binding function of an antibody. Examples of binding fragments denoted as an antigen-binding portion or fragment of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al. (1989) Nature 341, 544-546), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions are paired to form monovalent molecules (such a single chain cognate of an immunoglobulin fragment is known as a single chain Fv (scFv). Such single chain antibodies are also intended to be encompassed within the term "antibody". Antibody fragments are obtained using conventional techniques known to those with skill in the art, and the fragments are screened for utility in the same general manner as are intact antibodies. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Antigen binding fragments (including scFvs) of such immunoglobulins are also encompassed by the term "monoclonal antibody" as used herein. Monoclonal antibodies are highly specific, being directed against a single antigenic site. Furthermore, in contrast to conventional (polyclonal) antibody preparations, which typically include different antibodies, directed against different determinants (epitopes), each monoclonal antibody is directed against a single determinant on the antigen. Monoclonal antibodies can be prepared using any art recognized technique and those described herein such as, for example, a hybridoma method, a transgenic animal, recombinant DNA methods (see, e.g., U.S. Pat. No. 4,816,567), or using phage antibody libraries using the techniques described in, for example, U.S. Pat. No. 7,388,088 and US patent application Ser. No. 09/856,907 (PCT Int. Pub. No. WO 00/31246). Monoclonal antibodies include chimeric antibodies, human antibodies and humanized antibodies and may occur naturally or be produced recombinantly.

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody," as used herein, is intended to include antibodies having variable regions in which both the framework and CDR regions are derived from human germline immunoglobulin sequences as described, for example, by Kabat et al. (See Kabat, et al. (1991) *Sequences of proteins of Immunological Interest, Fifth Edition*, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue that is not encoded by the human germline immunoglobulin sequence. Typically, the human antibody can have up to twenty positions replaced with amino acid residues that are not part of the human germline immunoglobulin sequence. In a particular embodiment, these replacements are within the CDR regions as described in detail below.

The term "humanized antibody" refers to an antibody that includes at least one humanized antibody chain (i.e., at least one humanized light or heavy chain). The term "humanized antibody chain" (i.e., a "humanized immunoglobulin light chain") refers to an antibody chain (i.e., a light or heavy chain, respectively) having a variable region that includes a variable framework region substantially from a human antibody and complementarity determining regions (CDRs) (e.g., at least one CDR, two CDRs, or three CDRs) substantially from a non-human antibody, and further includes constant regions (e.g., one constant region or portion thereof, in the case of a light chain, and preferably three constant regions in the case of a heavy chain).

"Isolated," as used herein, is intended to refer to an antibody or combination of two, three or four antibodies that is substantially free of other antibodies having different antigenic specificities (e.g., an isolated composition of antibodies ca, cf, and ch, each of which specifically bind to EGFR, is substantially free of antibodies that specifically bind antigens other than EGFR). In addition, an isolated antibody is typically substantially free of other cellular material and/or chemicals. In one embodiment, a combination of "isolated" monoclonal antibodies having different EGFR binding specificities are combined in a well-defined composition.

As used herein, "isotype" refers to the antibody class (e.g., IgM or IgG1) that is encoded by heavy chain constant region genes. In some embodiments, a monoclonal antibody composition provided herein comprises only antibodies of the IgG1 isotype. In other embodiments, a monoclonal antibody composition provided herein comprises only antibodies of the IgG2 isotype. In other embodiments, a monoclonal antibody composition provided herein comprises antibodies of two or three different isotypes.

An "antigen" is an entity (e.g., a proteinaceous entity or peptide) to which an antibody binds. In various embodiments, an antigen is EGF. In a particular embodiment, an antigen is human EGFR.

Accordingly, also encompassed by the present disclosure are combinations of antibodies that bind to epitopes on EGFR which comprise all or a portion of the epitopes recognized by the particular antibodies of the combinations described herein. In another embodiment, the antibodies are provided that compete for binding to EGFR with the antibodies described herein. Competing antibodies and antibodies that recognize the same or an overlapping epitope can be identified using routine techniques such as an immunoassay, for example, by showing the ability of one antibody to block the binding of another antibody to a target antigen, i.e., a competitive binding assay. Competitive binding may be determined using an assay such as described in the Examples below.

The terms "specific binding," "specifically binds," "selective binding," and "selectively binds," mean that an antibody exhibits appreciable affinity for a particular antigen or epitope and, generally, does not exhibit significant cross-reactivity with other antigens and epitopes. "Appreciable" or preferred binding includes binding with a $K_D$ of $10^6$, $10^7$, $10^8$, $10^9$, or $10^{10}$ $M^{-1}$ or better. The $K_D$ of an antibody antigen interaction (the affinity constant) indicates the concentration of antibody at which 50% of antibody and antigen molecules are bound together. Thus, at a suitable fixed antigen concentration, 50% of a higher (i.e., stronger) affinity antibody will bind antigen molecules at a lower antibody concentration than would be required to achieve the same percent binding with a lower affinity antibody. Thus a lower $K_D$ value indicates a higher (stronger) affinity. As used herein, "better" affinities are stronger affinities, and are of lower numeric value than their comparators, with a $K_D$ of $10^7 M^{-1}$ being of lower numeric value and therefore representing a better affinity than a $K_D$ of $10^6 M^{-1}$. Affinities better (i.e., with a lower $K_D$ value and therefore stronger) than $10^7 M^{-1}$, preferably better than $10^8 M^{-1}$, are generally preferred. Values intermediate to those set forth herein are also contemplated, and a preferred binding affinity can be indicated as a range of affinities, for example preferred binding affinities for anti-EGFR antibodies disclosed herein are, $10^6$ to $10^{12} M^{-1}$, preferably $10^7$ to $10^{12} M^{-1}$, more preferably $10^8$ to $10^{12}$ M. An antibody that "does not exhibit significant cross-reactivity" is one that will not appreciably bind to an off target antigen (e.g., a non-EGFR protein). For example, in one embodiment, an antibody that specifically binds to EGFR will exhibit at least a two, and preferably three, or four or more orders of magnitude better binding affinity (i.e., binding exhibiting a two, three, or four or more orders of magnitude lower $K_D$ value) for EGFR than for ErbB molecules other than ErbB 1 (EGFR) or for non-ErbB proteins or peptides. Specific or selective binding can be determined according to any art-recognized means for determining such binding, including, for example, according to Scatchard analysis and/or competitive (competition) binding assays as described herein.

The term "$K_D$," as used herein, is intended to refer to the dissociation equilibrium constant of a particular antibody-antigen interaction or the affinity of an antibody for an antigen. In one embodiment, the antibody provided herein binds an antigen (e.g., EGFR) with an affinity ($K_D$) of 100 nM or better (i.e., or less) (e.g., 90 nM, 80 nM, 70 nM, 60 nM, 50 nM, 40 nM, 30 nM, 20 nM, 10 nM, 5 nM, 1 nM or less), as measured using a surface plasmon resonance assay, a cell binding assay, or an equilibrium dialysis assay. In a particular embodiment, an antibody binds EGFR with an affinity (as represented by dissociation constant $K_D$) of 8 nM or better (e.g., 7 nM, 6 nM, 5 nM, 4 nM, 2 nM, 1.5 nM, 1.4 nM, 1.3 nM, 1.2 nM, 1.1 nM, 1 nM or lower), as measured by a surface plasmon resonance assay or a cell binding assay. In other embodiments, an antibody binds an antigen (e.g., EGFR) with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument using recombinant EGFR as the analyte and the antibody as the ligand, and binds to the predetermined antigen with an affinity that is at least two-fold greater than its affinity for binding to a non-specific antigen (e.g., BSA, casein) other than the predetermined antigen or a closely-related antigen. Other methods for determining $K_D$ include equilibrium binding to live cells expressing EGFR via flow cytometry (FACS) or in solution using KinExA® technology.

The term "$K_{off}$," as used herein, is intended to refer to the off rate constant for the dissociation of an antibody from the antibody/antigen complex.

The terms "IC50" and "IC90," as used herein, refer to the measure of the effectiveness of a compound (e.g., an anti-EGFR antibody) in inhibiting a biological or biochemical function (e.g., the function or activity of EGFR) by 50% and 90%, respectively. For example, IC50 indicates how much of an anti-EGFR antibody is needed to inhibit the activity of EGFR (e.g., the growth of a cell expressing EGFR) by half. That is, it is the half maximal (50%) inhibitory concentration (IC) of an anti-EGFR antibody (50% IC, or $IC_{50}$). According to the FDA, IC50 represents the concentration of a drug that is required for 50% inhibition in vitro. The IC50 and IC90 can be determined by techniques known in the art, for example, by constructing a dose-response curve and examining the effect of different concentrations of the antagonist (i.e., the anti-EGFR antibody) on reversing EGFR activity.

As used herein, "glycosylation pattern" is defined as the pattern of carbohydrate units that are covalently attached to a protein, more specifically to an immunoglobulin protein.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody fragments (e.g., $V_H$, $V_L$, CDR3), is intended to refer to a nucleic acid molecule in which the nucleotide sequences are essentially free of other genomic nucleotide sequences, e.g., those encoding antibodies that bind antigens other than EGFR, which other sequences may naturally flank the nucleic acid in human genomic DNA.

The term "modifying," or "modification," as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis. For example, in some embodiments, an antibody or an antigen-binding portion thereof identified using the methods provided herein can be modified, to thereby modify the binding affinity of the antibody or antigen-binding portion thereof to EGFR.

"Conservative amino acid substitutions" in the sequences of the antibodies are provided, i.e., nucleotide and amino acid sequence modifications which do not abrogate the binding of the antibody encoded by the nucleotide sequence or containing the amino acid sequence, to the antigen, i.e., EGFR. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. Thus, a predicted nonessential amino acid residue in an anti-EGFR antibody is preferably replaced with another amino acid residue from the same class. Methods of identifying nucleotide and amino acid conservative substitutions which do not eliminate antigen binding are well-known in the art.

The term "non-conservative amino acid substitution" refers to the substitution of an amino acid in one class with an amino acid from another class; for example, substitution of an Ala, a class II residue, with a class III residue such as Asp, Asn, Glu, or Gln.

Alternatively, in another embodiment, mutations (conservative or non-conservative) can be introduced randomly along all or part of an anti-EGFR antibody coding sequence, such as by saturation mutagenesis, and the resulting modified anti-EGFR antibodies can be screened for binding activity.

A "consensus sequence" is a sequence formed from the most frequently occurring amino acids (or nucleotides) in a family of related sequences. In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence. Similarly, the consensus sequence for the CDRs of can be derived by optimal alignment of the CDR amino acid sequences of EGFR antibodies provided herein.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art.

The nucleic acid compositions, while often comprising a native sequence (except for modified restriction sites and the like), from either cDNA, genomic or mixtures thereof may alternately be mutated, in accordance with standard techniques to provide altered gene sequences. For coding sequences, these mutations, may modify the encoded amino acid sequence as desired. In particular, DNA sequences substantially homologous to native V, D, J, constant, switches and other such sequences described herein are contemplated.

The term "operably linked" refers to a nucleic acid sequence placed into a functional relationship with another nucleic acid sequence. For example, DNA for a presequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, other forms of expression vectors, such as viral vectors (e.g., replication defective retroviruses, adenoviruses and adeno-associated viruses), which serve equivalent functions are also contemplated.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject, an antibody or antibody pair or trio disclosed herein, for example, a subject having a disease or disorder associated with EGFR dependent signaling or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, adjunctive or combined administration (coadministration) includes simultaneous administration of two or more compounds in the same or different dosage form, or separate administration of two or more compounds (e.g., sequential administration). For example, two or more of the antibodies can be simultaneously administered together (e.g., formulated together). Alternatively, the antibodies can be administered in combination (e.g., formulated for separate administration and administered concurrently or sequentially). For example, a first antibody can be administered followed by the administration of a second antibody, or vice versa. Such concurrent or sequential administration preferably results in the two or more compounds (e.g., antibodies) being simultaneously present in treated patients.

The term "disease associated with EGFR dependent signaling," or "disorder associated with EGFR dependent signaling," as used herein, includes disease states and/or symptoms associated with a disease state, where increased levels of EGFR and/or activation of cellular cascades involving EGFR are found. The term "disease associated with EGFR dependent signaling," also includes disease states and/or symptoms associated with the activation of alternative EGFR signaling pathways. In general, the term "disease associated with EGFR dependent signaling," refers to any disorder, the onset, progression or the persistence of the symptoms of which requires the participation of EGFR. Exemplary EGFR-mediated disorders include, but are not limited to, for example, cancer.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma and various types of head and neck cancer. In a particular embodiment, a cancer treated or diagnosed using the methods disclosed herein is selected from melanoma, breast cancer, ovarian cancer, renal carcinoma, gastrointestinal/colon cancer, lung cancer, and prostate cancer.

The term "effective amount," as used herein, refers to that amount of an antibody or an antigen binding portion thereof that binds EGFR, which is sufficient to effect treatment, prognosis or diagnosis of a disease associated with EGFR dependent signaling, as described herein, when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody. Dosage regiments may be adjusted to provide the optimum therapeutic response. An effective amount is also one in which any toxic or detrimental effects (i.e., side effects) of an antibody are minimized and/or outweighed by the beneficial effects.

The term "therapeutic agent" in intended to encompass any and all compounds that have an ability to decrease or inhibit the severity of the symptoms of a disease or disorder, or increase the frequency and/or duration of symptom-free or symptom-reduced periods in a disease or disorder, or inhibit or prevent impairment or disability due to a disease or disorder affliction, or inhibit or delay progression of a disease or disorder, or inhibit or delay onset of a disease or disorder, or inhibit or prevent infection in an infectious disease or disorder. Non-limiting examples of therapeutic agents include small organic molecules, monoclonal antibodies, bispecific antibodies, recombinantly engineered biologics, RNAi compounds, tyrosine kinase inhibitors, and commercial antibodies. In certain embodiments, tyrosine kinase inhibitors include, e.g., one or more of erlotinib, gefitinib, and lapatinib, which are currently marketed pharmaceuticals. Commercially available pharmaceutical anti-EGFR antibodies include cetuximab and panitumumab. Other pharmaceutical anti-EGFR antibodies include zalutumumab, nimotuzumab, and matuzumab, which are in development.

The term "patient" includes human and other mammalian subjects that receive either prophylactic or therapeutic treatment.

The term "subject" includes any mammal, e.g., a primate. For example, the methods and compositions herein disclosed can be used to treat a subject having cancer. In a particular embodiment, the subject is a human.

The term "sample" refers to tissue, body fluid, or a cell (or a fraction of any of the foregoing) taken from a patient or a subject. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues can be obtained (e.g., leukemic cells from blood) and appropriately prepared. Other samples, including urine, tears, serum, plasma, cerebrospinal fluid, feces, sputum, cell extracts etc. can also be useful for particular cancers.

The term "SN-38," as used herein, refers to 7-Ethyl-10-hydroxy-camptothecin, which is an active metabolite of irinotecan commonly used in the art as a tool compound for irinotecan in in vitro experiments (CAS #86639-52-3). Irinotecan is a member of the topoisomerase I inhibitor class of drugs and is a semi-synthetic and water soluble analog of the naturally-occurring alkaloid, camptothecin. Also known as CPT-11, irinotecan is currently marketed formulated as an aqueous solution as Camptosar® (irinotecan hydrochloride injection). Topoisomerase I inhibitors such as irinotecan work to arrest uncontrolled cell growth by inhibiting the unwinding of DNA and thereby preventing DNA replication.

The pharmacology of irinotecan is complex, with extensive metabolic conversions involved in the activation, inactivation, and elimination of the drug. Irinotecan is a prodrug that is converted by nonspecific carboxylesterases into a 100-1000 fold more active metabolite, SN-38. Because these esterases, which act on irinotecan within the body are not expressed by many cells, including many, if not all, of the experimental cell lines used in the Examples below, SN-38 is often substituted for irinotecan in cell culture experiments. Irinotecan hydrochloride injection is approved in the United States for treatment of metastatic colon or renal cancer and is also used to treat colorectal, gastric, lung, uterine cervical and ovarian cancers.

Various aspects of the disclosure are described in further detail in the following subsections.

II. Anti-EGFR Antibodies and Combinations Thereof

Novel anti-EGFR monoclonal antibodies are disclosed herein, including three referred to in the Examples as P1X, P2X and P3X. The P1X, P2X and P3X monoclonal antibodies are affinity matured antibodies of parental antibodies referred to as ca, cd and ch, respectively, disclosed in PCT Application No. PCT/US2011/35238. The CDR amino acid sequences of the parental and affinity matured antibodies are shown below, with the changed amino acids in the affinity matured antibodies bolded and underlined:

```
ca V_H  CDR1            CDR2             CDR3
        SYAIS           IIPIFGTANY       DPSVDL
        (SEQ ID NO: 1)  (SEQ ID NO: 27)  (SEQ ID NO: 28)

P1X V_H CDR1            CDR2             CDR3
        SYAIS           IIPIFGTVNY       DPSVNL
        (SEQ ID NO: 1)  (SEQ ID NO: 2)   (SEQ ID NO: 3)

ca V_L  CDR1            CDR2             CDR3
        QSISSWLA        DASSL            QQFAAHA
        (SEQ ID NO: 29) (SEQ ID NO: 5)   (SEQ ID NO: 30)

P1X V_L CDR1            CDR2             CDR3
        QSISSWWA        DASSL            QQYHAHP
        (SEQ ID NO: 4)  (SEQ ID NO: 5)   (SEQ ID NO: 6)

cd V_H  CDR1            CDR2             CDR3
        SYAIS           IIPIFGTANY       MGRGKV
        (SEQ ID NO: 7)  (SEQ ID NO: 27)  (SEQ ID NO: 9)

P2X V_H CDR1            CDR2             CDR3
        SYAIS           IIPIFGAANP       MGRGKV
        (SEQ ID NO: 7)  (SEQ ID NO: 8)   (SEQ ID NO: 9)

cd V_L  CDR1              CDR2           CDR3
        QSVLYSSNNKNYLA    WASTR          QQYYGSP
        (SEQ ID NO: 31)   (SEQ ID NO: 11)(SEQ ID NO: 12)

P2X V_L CDR1              CDR2           CDR3
        QSVLYSPNNKNYLA    WASTR          QQYYGSP
        (SEQ ID NO: 10)   (SEQ ID NO: 11)(SEQ ID NO: 12)

ch V_H  CDR1            CDR2             CDR3
        SYGIN           ISAYNGNTNY       DLGGYGSGS
        (SEQ ID NO: 13) (SEQ ID NO: 32)  (SEQ ID NO: 15)

P3X V_H CDR1            CDR2             CDR3
        SYGIN           ISAYNGNTYY       DLGGYGSGS
        (SEQ ID NO: 13) (SEQ ID NO: 14)  (SEQ ID NO: 15)

ch V_L  CDR1            CDR2             CDR3
        QSVSSNLA        GASTR            QDYRTWPR
        (SEQ ID NO: 16) (SEQ ID NO: 17)  (SEQ ID NO: 18)

P3X V_L CDR1            CDR2             CDR3
        QSVSSNLA        GASTR            QDYRTWPR
        (SEQ ID NO: 16) (SEQ ID NO: 17)  (SEQ ID NO: 18)
```

The full-length $V_H$ and $V_L$ amino sequences for P1X are shown in SEQ ID NO: 19 and 20, respectively. The full-length $V_H$ and $V_L$ amino sequences for P2X are shown in SEQ ID NO: 21 and 22, respectively. The full-length $V_H$ and $V_L$ amino sequences for P3X are shown in SEQ ID NO: 23 and 24, respectively. Additionally, the $V_H$ and $V_L$ CDR segments as presented herein are arranged, e.g., in the amino to carboxy terminal order of CDR1, CDR2 and CDR3.

In one embodiment, a monoclonal antibody is provided which binds EGFR extracellular domain and comprises heavy and light chain CDR1, CDR2, and CDR3, sequences, wherein the heavy and light chain CDR1, CDR2, and CDR3, sequences are selected from the group consisting of:
(a) heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively;
(b) heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively; and
(c) heavy chain CDR1, CDR2, and CDR3 sequences of SEQ ID NOs: 13, 14, and 15, respectively, and light chain CDR1, CDR2, and CDR3 sequences of SEQ ID NOs: 16, 17, and 18, respectively.

In another embodiment, a monoclonal antibody is provided that binds to EGFR extracellular domain and comprises a heavy chain variable region and a light chain variable region, wherein the heavy and light chain variable region sequences are selected from the group consisting of:
(a) a heavy chain variable region comprising SEQ ID NO: 19 and a light chain variable region comprising SEQ ID NO: 20;
(b) a heavy chain variable region comprising SEQ ID NO: 21 and a light chain variable region comprising SEQ ID NO: 22; and
(c) a heavy chain variable region comprising SEQ ID NO: 23 and a light chain variable region comprising SEQ ID NO: 24.

Combinations of the aforementioned anti-EGFR antibodies are also provided. Such combinations can contain, for example, any combination of two of the aforementioned anti-EGFR antibodies. Another combination can comprise all three of the aforementioned anti-EGFR antibodies. Accordingly, in another aspect, a composition comprising two or three monoclonal antibodies which bind to EGFR extracellular domain is provided, wherein the two or three monoclonal antibodies are selected from the group consisting of:
(a) a monoclonal antibody comprising heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively;
(b) a monoclonal antibody comprising heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively and
(c) a monoclonal antibody comprising heavy chain CDR1, CDR2, and CDR3 sequences of SEQ ID NOs: 13, 14, and 15, respectively, and light chain CDR1, CDR2, and CDR3 sequences of SEQ ID NOs: 16, 17 and 18, respectively; and wherein the composition comprises (a) and (b), (a) and (c), (b) and (c) or (a), (b) and (c).

In yet another embodiment, a composition comprising two or three monoclonal antibodies which bind to EGFR extracellular domain is provided, wherein the two or three monoclonal antibodies are selected from the group consisting of:
(a) a monoclonal antibody comprising a heavy chain variable region comprising SEQ ID NO: 19 and a light chain variable region comprising SEQ ID NO: 20;
(b) a monoclonal antibody comprising a heavy chain variable region comprising SEQ ID NO: 21 and a light chain variable region comprising SEQ ID NO: 22; and
(c) a monoclonal antibody comprising a heavy chain variable region comprising SEQ ID NO: 23 and a light chain variable region comprising SEQ ID NO: 24; and wherein the composition comprises (a) and (b), (a) and (c), (b) and (c) or (a) (b) and (c).

The anti-EGFR antibodies disclosed herein, whether as a single antibody or in a combination of antibodies, can bind to EGFR with a $K_D$ of, for example, better than 100 nM, or better than 10 nM or better than 1 nM. As used herein with respect to $K_D$, the term "better than _____ nM" means that an antibody has a $K_D$, expressed as a nanomolar concentration, that is lower than the indicated number. For example, a $K_D$ that is "better than" 100 nM indicates a $K_D$, expressed as a nanomolar concentration, that is lower in value than 100 nM (e.g., is 50 nM).

In other embodiments, a P1X-related antibody, such as an antibody comprising heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively, or an antibody comprising $V_H$ and $V_L$ sequences of SEQ ID NOs: 19 and 20, respectively, can bind to EGFR with a $K_D$ in a range of about $1 \times 10^{-9}$ M to $1.1 \times 10^{-11}$ M or better.

In other embodiments, a P2X-related antibody, such as an antibody comprising heavy chain CDR1, CDR2, and CDR3 sequences of SEQ ID NOs: 7, 8 and 9 respectively, and light chain CDR1, CDR2, and CDR3 sequences of SEQ ID NOs: 10, 11, and 12, respectively, or an antibody comprising $V_H$ and $V_L$ sequences of SEQ ID NOs: 21 and 22, respectively, can bind to EGFR with a $K_D$ in a range of about $1 \times 10^{-9}$ M to $7.0 \times 10^{-11}$ M or better.

In other embodiments, a P3X-related antibody, such as an antibody comprising heavy chain CDR1, CDR2, and CDR3 sequences of SEQ ID NOs: 13, 14 and 15 respectively, and light chain CDR1, CDR2, and CDR3 sequences of SEQ ID NOs: 16, 17, and 18, respectively, or an antibody comprising $V_H$ and $V_L$ sequences of SEQ ID NOs: 23 and 24, respectively, can bind to EGFR with a $K_D$ in a range of about $1 \times 10^{-9}$ M to $3.6 \times 10^{-10}$ M or better.

The anti-EGFR antibodies disclosed herein, whether as a single antibody or in a combination of antibodies, can exhibit one or more other functional properties as disclosed herein, including but not limited to (a) inhibition of AKT or ERK phosphorylation, e.g., EGFR-dependant AKT or ERK phosphorylation, as measured in a cell-based assay;

(b) inhibition of the growth of cells expressing EGFR;

(c) inhibition of EGF ligand binding to EGFR (e.g., inhibition of binding of one or more ligands that bind EGFR, including EGF, heparin binding EGF-like growth factor (HB-EGF), transforming growth factor (TGF), epigen, epiregulin, betacellulin, or amphiregulin);

(d) inhibition of EGFR dimerization;

(e) downregulation of EGFR on cell surfaces (e.g., by internalization and recycling of the receptor, and/or internalization and degradation of the receptor);

(f) inhibition of in vitro tumor cell proliferation; and/or (g) inhibition of in vivo tumor growth.

Antibodies disclosed herein include all known forms of antibodies and other protein scaffolds with antibody-like properties. For example, the antibody can be a human antibody, a humanized antibody, a bispecific antibody, an immunoconjugate, a chimeric antibody or a protein scaffold with antibody-like properties, such as fibronectin or ankyrin repeats. The antibody also can be a Fab, Fab'2, ScFv, Affibody®, avimer, nanobody, or a domain antibody. The antibody also can have any isotype, including any of the following isotypes: IgG1, IgG2, IgG3, IgG4, IgM, IgA1, IgA2, IgAsec, IgD, and IgE. IgG antibodies are preferred. Full-length antibodies can be prepared from $V_H$ and $V_L$ sequences using standard recombinant DNA techniques and nucleic acid encoding the desired constant region sequences to be operatively linked to the variable region sequences. Non-limiting examples of suitable constant region sequences include the kappa light chain constant region disclosed in SEQ ID NO: 25 and the IgG1 heavy chain constant region disclosed in SEQ ID NO: 26.

As disclosed in the examples, it has been discovered that triple combinations of the P1X+P2X+P3X antibodies are particularly efficacious when used at a P1X:P2X:P3X molar ratio of 2:2:1. Thus, for such a triple antibody combination, 40% of the total concentration is selected to be P1X, 40% of the total concentration is selected to be P2X and 20% of the total concentration is selected to be P3X.

Accordingly, in another embodiment, s a composition is provided comprising three monoclonal anti-EGFR antibodies, said composition comprising a first antibody, a second antibody and a third antibody, wherein (i) the first antibody comprises heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively; (ii) the second antibody comprises heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively; and (iii) the third antibody comprises heavy chain CDR1, CDR2, and CDR3 sequences of SEQ ID NOs: 13, 14, and 15 respectively, and light chain CDR1, CDR2, and CDR3 sequences of SEQ ID NOs: 16, 17, and 18, respectively, and wherein the first second and third antibodies are present at a molar ratio of 2:2:1 to each other.

In yet another embodiment, a composition is provided comprising three monoclonal anti-EGFR antibodies, said composition comprising a first antibody, a second antibody and a third antibody, wherein (i) the first antibody comprises a heavy chain variable region comprising SEQ ID NO: 19 and a light chain variable region comprising SEQ ID NO: 20; (ii) the second antibody comprises a heavy chain variable region comprising SEQ ID NO: 21 and a light chain variable region comprising SEQ ID NO: 22; and (iii) the third antibody comprises a heavy chain variable region comprising SEQ ID NO: 23 and a light chain variable region comprising SEQ ID NO: 24, and wherein the first second and third antibodies are present at a molar ratio of 2:2:1 to each other.

Methods of preparing anti-EGFR antibody compositions comprising three antibodies are provided, wherein the antibodies are prepared at a 2:2:1 ratio. More specifically, in another embodiment, a method of preparing an anti-EGFR antibody composition is provided, the method comprising combining in a single composition:

(a) a monoclonal antibody comprising heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively;

(b) a monoclonal antibody comprising heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively; and (c) a monoclonal antibody comprising heavy chain CDR1, CDR2, and CDR3 sequences of SEQ ID NOs: 13, 14, and 15 respectively, and light chain CDR1, CDR2, and CDR3 sequences of SEQ ID NOs: 16, 17, and 18, respectively;

wherein (a), (b) and (c) are combined at a molar ratio of 2:2:1 to each other.

In another embodiment, a method of preparing an anti-EGFR antibody composition is provided, the method comprising combining in a single composition:

(a) a monoclonal antibody comprising a heavy chain variable region comprising SEQ ID NO: 19 and a light chain variable region comprising SEQ ID NO:20;

(b) a monoclonal antibody comprising a heavy chain variable region comprising SEQ ID NO: 21 and a light chain variable region comprising SEQ ID NO: 22; and (c) a monoclonal antibody comprising a heavy chain variable region comprising SEQ ID NO: 23 and a light chain variable region comprising SEQ ID NO: 24;

wherein (a), (b) and (c) are combined at a molar ratio of 2:2:1 to each other.

Methods of treating a subject with three anti-EGFR antibodies wherein the antibodies are administered to the subject at a 2:2:1 ratio are also provided. More specifically, a method of treating a subject with anti-EGFR antibodies is provided, the method comprising administering to the subject:

(a) a monoclonal antibody comprising heavy chain CDR1, CDR2, and CDR3 sequences of SEQ ID NOs: 1, 2, and 3 respectively, and light chain CDR1, CDR2, and CDR3 sequences of SEQ ID NOs: 4, 5, and 6, respectively;

(b) a monoclonal antibody comprising heavy chain CDR1, CDR2, and CDR3 sequences of SEQ ID NOs: 7, 8, and 9, respectively, and light chain CDR1, CDR2, and CDR3 sequences of SEQ ID NOs: 10, 11 and 12, respectively; and (c) a monoclonal antibody comprising heavy chain CDR1, CDR2, and CDR3 sequences of SEQ ID NOs: 13, 14, and 15 respectively, and light chain CDR1, CDR2, and CDR3 sequences of SEQ ID NOs: 16, 17, and 18, respectively;

wherein (a), (b) and (c) are administered to the subject at a molar ratio of 2:2:1 to each other.

In another embodiment, a method of treating a subject with anti-EGFR antibodies is provided, the method comprising administering to the subject:

(a) a monoclonal antibody comprising a heavy chain variable region comprising SEQ ID NO: 19 and a light chain variable region comprising SEQ ID NO:20;

(b) a monoclonal antibody comprising a heavy chain variable region comprising SEQ ID NO: 21 and a light chain variable region comprising SEQ ID NO: 22; and (c) a monoclonal antibody comprising a heavy chain variable region comprising SEQ ID NO: 23 and a light chain variable region comprising SEQ ID NO: 24;

wherein (a), (b) and (c) are administered to the subject at a molar ratio of 2:2:1 to each other.

Further details on formulating anti-EGFR antibodies into pharmaceutical compositions and methods of using such compositions in EGFR-related diseases are described in subsections below.

III. Methods for Producing Antibodies (i) Monoclonal Antibodies

The monoclonal antibodies of provided herein most typically are prepared by standard recombinant DNA techniques based on the amino acid sequences of the $V_H$ and $V_L$ regions disclosed herein.

Additionally or alternatively, monoclonal antibodies can be produced using a variety of known techniques, such as the standard somatic cell hybridization technique, viral or oncogenic transformation of B lymphocytes, or yeast or phage display techniques using libraries of human antibody genes. In particular embodiments, the antibodies are fully human monoclonal antibodies.

Accordingly, in one embodiment, a hybridoma method is used for producing an antibody that binds EGFR. In this method, a mouse or other appropriate host animal can be immunized with a suitable antigen in order to elicit lymphocytes that produce or are capable of producing antibodies that will specifically bind to the antigen used for immunization.

Alternatively, lymphocytes may be immunized in vitro. Lymphocytes can then be fused with myeloma cells using a suitable fusing agent, such as polyethylene glycol, to form a hybridoma cell. Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods. Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies that bind EGFR can be isolated from antibody libraries generated using well know techniques such as those described in, for example, U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al., Additionally, production of high affinity (nM range) human antibodies by chain shuffling, as well as combinatorial infection and in vivo recombination as a strategy for constructing very large phage libraries may also be used. See, e.g., U.S. patent application Ser. No. 09/856,907 (PCT Int. Pub. No. WO 00/31246)

In a particular embodiment, the monoclonal antibody that binds EGFR is produced using phage display. This technique involves the generation of a human Fab library having a unique combination of immunoglobulin sequences isolated from human donors and having synthetic diversity in the heavy-chain CDRs is generated. The library is then screened for Fabs that bind to EGFR.

In yet another embodiment, human monoclonal antibodies directed against EGFR can be generated using transgenic or transchromosomic mice carrying parts of the human immune system rather than the mouse system (see e.g., U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.).

In another embodiment, human antibodies can be raised using a mouse that carries human immunoglobulin sequences on transgenes and transchomosomes, such as a mouse that carries a human heavy chain transgene and a human light chain transchromosome (see e.g., PCT Publication WO 02/43478 to Ishida et al.).

Still further, alternative transgenic animal systems expressing human immunoglobulin genes are available in the art and can be used to raise anti-EGFR antibodies. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-EGFR antibodies. For example, mice carrying both a human heavy chain transchromosome and a human light chain tranchromosome can be used. Furthermore, cows carrying human heavy and light chain transchromosomes have been described in the art and can be used to raise anti-EGFR antibodies.

In yet another embodiment, antibodies can be prepared using a transgenic plant and/or cultured plant cells (such as, for example, tobacco, maize and duckweed) that produce such antibodies. For example, transgenic tobacco leaves expressing antibodies can be used to produce such antibodies by, for example, using an inducible promoter. Also, transgenic maize can be used to express such antibodies and antigen binding portions thereof. Antibodies can also be produced in large amounts from transgenic plant seeds including antibody portions, such as single chain antibodies (scFv's), for example, using tobacco seeds and potato tubers.

The binding specificity of monoclonal antibodies (or portions thereof) that bind EGFR prepared using any technique including those disclosed here, can be determined by immunoprecipitation or by an in vitro binding assay, such as radioimmunoassay (RIA) or enzyme-linked immunoabsorbent assay (ELISA). The binding affinity of a monoclonal antibody or portion thereof also can be determined by Scatchard analysis.

In certain embodiments, an EGFR antibody produced using any of the methods discussed above may be further altered or optimized to achieve a desired binding specificity and/or affinity using art recognized techniques, such as those described herein.

In one embodiment, partial antibody sequences derived from an EGFR antibody may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Such framework sequences can be obtained from public DNA databases that include germline antibody gene sequences.

Thus, one or more structural features of an anti-EGFR antibody, such as the CDRs, can be used to create structurally related anti-EGFR antibodies that retain at least one desired functional property, e.g., inhibiting growth of cells expressing EGFR.

In a particular embodiment, one or more CDR regions disclosed herein is combined recombinantly with known human framework regions and CDRs to create additional, recombinantly-engineered, anti-EGFR antibodies. The heavy and light chain variable framework regions can be derived from the same or different antibody sequences.

It is well known in the art that antibody heavy and light chain CDR3 domains play a particularly important role in the binding specificity/affinity of an antibody for an antigen. Accordingly, in certain embodiments, antibodies are generated that include the heavy and/or light chain CDR3s of the particular antibodies described herein. The antibodies can further include the heavy and/or light chain CDR1 and/or CDR2s of the antibodies disclosed herein.

The CDR 1, 2, and/or 3 regions of the engineered antibodies described above can comprise the exact amino acid sequence(s) as those disclosed herein. However, the ordinarily skilled artisan will appreciate that some deviation from the exact CDR sequences may be possible, particularly for CDR1 and CDR2 sequences, which can tolerate more variation than CDR3 sequences without altering epitope specificity (such deviations are, e.g., conservative amino acid substitutions). Accordingly, in another embodiment, the engineered antibody may be composed of one or more CDR1s and CDR2s that are, for example, 90%, 95%, 98%, 99% or 99.5% identical to the corresponding CDRs of an antibody named herein.

In another embodiment, one or more residues of a CDR may be altered to modify binding to achieve a more favored on-rate of binding. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Modifications can also be made within one or more of the framework or joining regions of the heavy and/or the light chain variable regions of an antibody, so long as antigen binding affinity subsequent to these modifications is better than $10^6$ $M^{-1}$.

In another embodiment, the antibody is further modified with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Homodimeric antibodies with enhanced anti-tumor activity may also be prepared using heterobifunctional cross-linkers. Alternatively, an antibody can be engineered which has dual Fc regions and may thereby have enhanced complement lysis and ADCC capabilities.

Also provided are bispecific antibodies and immunoconjugates, as discussed below.

(ii) Bispecific Antibodies

Bispecific antibodies herein include at least two binding specificities for EGFR which preferably bind non-overlapping or non-competing epitopes. Such bispecific antibodies can include additional binding specificities, e.g., a third EGFR binding specificity and/or a binding specificity for another ErbB receptor (e.g., ErbB3) or another antigen, such as the product of an oncogene. Bispecific antibodies can be prepared as full length antibodies or antibody fragments (e.g. F(ab')$_2$ bispecific antibodies).

Methods for making bispecific antibodies are well known in the art (see, e.g., WO 05117973 and WO 06091209). For example, production of full length bispecific antibodies can be based on the coexpression of two paired immunoglobulin heavy chain-light chains, where the two chains have different specificities. Various techniques for making and isolating bispecific antibody fragments directly from recombinant cell culture have also been described. For example, bispecific antibodies have been produced using leucine zippers. Another strategy for making bispecific antibody fragments by the use of single-chain Fv (sFv) dimers has also been reported.

In a particular embodiment, the bispecific antibody comprises a first antibody (or binding portion thereof) which binds to EGFR derivatized or linked to another functional molecule, e.g., another peptide or protein (e.g., another antibody or ligand for a receptor) to generate a bispecific molecule that binds to at least two different binding sites or target molecules. An antibody may be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, an antibody disclosed herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, bispecific molecules comprising at least one first binding specificity for EGFR and a second binding specificity for a second target epitope are contemplated. In a particular embodiment, the second target epitope is an Fc receptor, e.g., human FcγRI (CD64) or a human Fcα receptor (CD89). Therefore, bispecific molecules capable of binding both to FcγR, FcαR or FcεR expressing effector cells (e.g., monocytes, macrophages or polymorphonuclear cells (PMNs)), and to target cells expressing EGFR are also provided. These bispecific molecules target EGFR expressing cells to effector cell and trigger Fc receptor-mediated effector cell activities, such as phagocytosis of an EGFR expressing cells, antibody dependent cell-mediated cytotoxicity (ADCC), cytokine release, or generation of superoxide anion.

In one embodiment, the bispecific molecules comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

The bispecific molecules can be prepared by conjugating the constituent binding specificities, e.g., the anti-FcR and anti-EGFR binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand×Fab fusion protein. A bispecific molecule can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (RIA), FACS analysis, bioassay (e.g., growth inhibition), or western blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA). The radioactive isotope can be detected by such means as the use of a α γ-βcounter or a scintillation counter or by autoradiography.

(iii) Immunoconjugates

Immunoconjugates provided herein can be formed by conjugating the antibodies described herein to another therapeutic agent. Suitable agents include, for example, a cytotoxic agent (e.g., a chemotherapeutic agent), a toxin (e.g. an enzymatically active toxin of bacterial, fungal, plant or animal origin, or fragments thereof), and/or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-EGFR antibodies. Examples include $^{212}$Bi, $^{131}$I, $^{131}$In, $^{90}$Y and $^{186}$Re.

Immunoconjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., WO94/11026).

IV. Methods for Screening Antibodies

Subsequent to producing antibodies they can be screened for various properties, such as those described herein, using a variety of assays that are well known in the art.

In one embodiment, the antibodies are screened (e.g., by flow cytometry or ELISA) for binding to EGFR using, for example, purified EGFR and/or EGFR-expressing cells, such as A431 cells. The epitopes bound by the anti-EGFR antibodies can further be identified and compared, for example, to identify non-competing antibodies (e.g., antibodies that bind different epitopes), as well as antibodies which compete for binding and/or bind the same or overlapping epitopes.

Competitive antibodies and non-competitive antibodies can be identified using routine techniques. Such techniques include, for example, an immunoassay, which shows the ability of one antibody to block (or not block) the binding of another antibody to a target antigen, i.e., a competitive binding assay. Competitive binding is determined in an assay in which the immunoglobulin under test inhibits specific binding of a reference antibody to a common antigen, such as EGFR. Numerous types of competitive binding assays are known, for example: solid phase direct or indirect radioimmunoassay (RIA), solid phase direct or indirect enzyme immunoassay (EIA), sandwich competition assay; solid phase direct biotin-avidin EIA; solid phase direct labeled assay, solid phase direct labeled sandwich assay; solid phase direct $^{125}$I labeled RIA; solid phase direct biotin-avidin EIA; and direct labeled RIA. The surface plasmon resonance technique set forth in the Materials and Methods of the Examples and in Example 2, below, can also be used advantageously for this purpose. Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other screening techniques for determining the epitope bound by antibodies disclosed herein include, for example, x-ray analysis of crystals of antigen:antibody complexes, which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

In another embodiment, the antibodies (e.g., non-competing antibodies anti-EGFR antibodies) are screened for the ability to bind to epitopes exposed upon binding to ligand, e.g., EGF (i.e., do not inhibit the binding of EGFR-binding ligands to EGFR). Such antibodies can be identified by, for example, contacting cells which express EGFR (e.g. A431 cells) with a labeled EGFR ligand (e.g., radiolabeled or biotinylated EGF) in the absence (control) or presence of the anti-EGFR antibody. If the antibody does not inhibit EGF binding to EGFR, then no statistically significantly decrease in the amount of label recovered, relative to the amount in the absence of the antibody, will be observed. Alternatively, if the antibody inhibits EGF binding to EGFR, then a statistically significantly decrease in the amount of label recovered, relative to the amount in the absence of the antibody, will be observed.

Antibodies also can be screened (tested) for their binding affinity. This can be done, for example, using a plasmon resonance assay, e.g., as described below.

Antibodies also can be screened for their ability to inhibit signaling through EGFR using signaling assays, such as, those described herein. For example, the ability of an antibody to inhibit EGFR ligand mediated phosphorylation of EGFRs can be assessed by treating cells expressing EGFR with an EGFR ligand (e.g., EGF) in the presence and absence of the antibody. The cells can then be lysed, crude lysates centrifuged to remove insoluble material, and EGFR phosphorylation measured, for example, by western blotting followed by probing with an anti-phosphotyrosine antibody.

Alternatively, the ability of an antibody to inhibit downstream signaling through EGFR can be measured by kinase assays for known substrates of EGFR such as, for example, AKT and/or ERK, following EGFR stimulation by EGF ligand. For example, cells expressing EGFR can be incubated with a candidate antibody and stimulated with EGF ligand. Cell lysates subsequently prepared from such cells can be immunoprecipitated with an antibody for a substrate of EGFR (or a protein in a cellular pathway involving EGFR) such as, an anti-AKT antibody, and assayed for kinase activity (e.g., AKT kinase activity) using art-recognized techniques. A decrease in or complete disappearance in level or activity (e.g., kinase activity) of a EGFR substrate or protein in a pathway involving EGFR in the presence of the antibody, relative to the level or activity in the absence of the antibody is indicative of an antibody which inhibits EGFR signaling.

Antibodies that decrease levels of EGFR on cell surfaces can be identified by their ability to downregulate or inhibit EGFR expression on tumor cells. In certain embodiments, the antibodies decrease EGFR on cell surfaces by inducing internalization (or increasing endocytosis) of EGFR (e.g., by internalization and recycling of the receptor and/or internalization and degradation of the receptor) or by inhibiting recycling of internalized EGFR. To test this, EGFR can be biotinylated and the number of EGFR molecules on the cell surface can be readily determined, for example, by measuring the amount of biotin on a monolayer of cells in culture in the presence or absence of an antibody, followed by immunoprecipitation of EGFR and probing with streptavidin. A decrease in detection of biotinylated EGFR over time in the presence of an antibody is indicative of an antibody that decreases EGFR levels on cell surfaces.

Antibodies and antibody combinations can also be tested for their ability to inhibit growth of cells expressing EGFR (either in vivo or in vitro), such as tumor cells, using art recognized techniques, including the Cell Titer-Glo Assay described in the Examples below and Tritium-labeled thymidine incorporation assay. Antibodies also can be screened for the ability to inhibit spheroid growth of cells expressing EGFR. This can be done by using an assay that approximates conditions of a developing tumor growth as described herein.

In another embodiment, combinations of anti-EGFR antibodies are screened for IC50 and/or IC90 values relative to inhibiting a particular EGFR activity or function, such as EGFR-mediated signaling (e.g., as measured by ELISA, Western, or multiplex methods, such as Luminex®). Combinations of antibodies, each of which possesses a particularly desired IC50 and/or IC90 value (e.g., an IC90 of about 80 nM for inhibiting EGFR signaling) can then be selected. In one embodiment, the combination has a greater IC50 or IC90 value than a known reference antibody (e.g., cetuximab). In another embodiment, the combination has an additive IC50 or IC90 (i.e., the sum of the activities of the antibodies, when acting individually on a cell expressing EGFR, is approximately equivalent to the combined effect of the same antibodies acting together on the same cell) In another embodiment, the combination has a synergistic IC50 or IC90 (i.e., the sum of the effects of the antibodies, when acting individually on a cell expressing EGFR, is less than the combined effect of the same antibodies acting together on the same cell).

V. Pharmaceutical Compositions

In another aspect, herein provided is a composition, e.g., a pharmaceutical composition, containing one or a combination of the anti-EGFR monoclonal antibodies disclosed herein, formulated together with a pharmaceutically acceptable carrier. In one embodiment, the compositions include a combination of multiple (e.g., two or three) isolated antibodies that bind different epitopes on EGFR. Such antibodies preferably have an additive or synergistic effect relative to inhibiting a particular EGFR activity or function, such as EGFR-mediated signaling. Preferred pharmaceutical compositions are sterile compositions, compositions suitable for injection, and sterile compositions suitable for injection by a desired route of administration, such as by intravenous injection.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

Compositions can be administered alone or in combination therapy, i.e., combined with other agents. For example, the combination therapy can include a composition provided herein with at least one or more additional therapeutic agents, such as the anti-cancer agents described herein. In one embodiment, combination therapy can use a composition provided herein of two or three of the anti-EGFR antibodies disclosed herein. In another embodiment, combination therapy can use a composition comprising at least one of the anti-EGFR antibodies disclosed herein combined with one or more other antibodies, such as one or more other anti-EGFR antibodies known in the art (e.g., anti-EGFR antibodies as disclosed in PCT Application No. PCT/US2011/3528). The compositions can also be administered in conjunction with radiation therapy and/or surgery. Particular combinations of anti-EGFR antibodies may also be administered separately or sequentially, with or without additional therapeutic agents.

Compositions can be administered by a variety of methods known in the art. As will be appreciated by the skilled artisan, the route and/or mode of administration will vary depending upon the desired results. The antibodies can be prepared with carriers that will protect the antibodies against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer compositions by certain routes of administration, it may be necessary to coat the constituents, e.g., antibodies, with, or co-administer the compositions with, a material to prevent its inactivation. For example, the compositions may be administered to a subject in an appropriate carrier, for example, liposomes, or a diluent. Acceptable diluents include saline and aqueous buffer solutions. Liposomes include water-in-oil-in-water CGF emulsions as well as conventional liposomes.

Acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional medium or agent is incompatible with the antibodies, use thereof in compositions provided herein is contemplated. Supplementary active constituents can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Including in the composition an agent that delays absorption, for example, monostearate salts and gelatin can bring about prolonged absorption of the injectable compositions.

Sterile injectable solutions can be prepared by incorporating the monoclonal antibodies in the required amount in an appropriate solvent with one or a combination of ingredients enumerated above, as required, followed by sterilization microfiltration. Generally, dispersions are prepared by incorporating the antibodies into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, human antibodies may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of antibodies calculated to produce the desired therapeutic effect in association with the required pharmaceutical carrier. The specification for the dosage unit forms provided herein are dictated by and directly dependent on (a) the unique characteristics of the antibodies and the particular therapeutic effect to be achieved, and (b) the limitations inherent in the art of compounding such antibodies for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations include those suitable for oral, nasal, topical (including buccal and sublingual), rectal, and parenteral administration. Parenteral administration is the most common route of administration for therapeutic compositions comprising antibodies. The formulations may conveniently be presented in unit dosage form and may be prepared by any methods known in the art of pharmacy. The amount of antibodies that can be combined with a carrier material to produce a single dosage form will vary depending upon the subject being treated, and the particular mode of administration. This amount of antibodies will generally be an amount sufficient to produce a therapeutic effect. Generally, out of one hundred percent, this amount will range from about 0.001 percent to about ninety percent of antibody by mass, preferably from about 0.005 percent to about 70 percent, most preferably from about 0.01 percent to about 30 percent.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Examples of suitable aqueous and nonaqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Particular examples of adjuvants which are well-known in the art include, for example, inorganic adjuvants (such as aluminum salts, e.g., aluminum phosphate and aluminum hydroxide), organic adjuvants (e.g., squalene), oil-based adjuvants, virosomes (e.g., virosomes which contain a membrane-bound heagglutinin and neuraminidase derived from the influenza virus).

Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of one or more agents that delay absorption such as aluminum monostearate or gelatin.

When compositions are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, compositions provided herein, may be used in a suitable hydrated form, and they may be formulated into pharmaceutically acceptable dosage forms by conventional methods known to those of skill in the art.

Actual dosage levels of the antibodies in the pharmaceutical compositions provided herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the composition required. For example, the physician or veterinarian could start doses of the antibodies at levels lower than that required to achieve the desired therapeutic effect and gradually increasing the dosage until the desired effect is achieved. In general, a suitable daily dose of compositions provided herein will be that amount of the antibodies which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for antibodies to be administered alone, it is preferable to administer antibodies as a formulation (composition).

Therapeutic compositions can be administered with medical devices known in the art, such as, for example, those disclosed in U.S. Pat. Nos. 5,399,163, 5,383,851, 5,312,335, 5,064,413, 4,941,880, 4,790,824, 4,596,556, 4,487,603, 4,486,194, 4,447,233, 4,447,224, 4,439,196, and 4,475,196.

In certain embodiments, the monoclonal antibodies can be formulated to ensure proper distribution in vivo. For example, the blood-brain barrier (BBB) excludes many highly hydrophilic compounds. To ensure that therapeutic antibodies cross the BBB (if desired), they can be formulated, for example, in liposomes. For methods of manufacturing liposomes, see, e.g., U.S. Pat. Nos. 4,522,811; 5,374,548; 5,399,331; 5,891,468; 6,056,973; 6,210,707; 6,224,903; 6,316,024; 7,122,202; 7,135,177; and 7,507,407 and US Patent Publication 20070116753. The liposomes may comprise one or more moieties that attach to and/or are selectively transported into specific cells or organs, thus enhance targeted drug delivery.

Pharmaceutical compositions are provided that comprise trios of anti-EGFR antibodies at a 2:2:1 ratio, that is the composition comprises three different anti-EGFR antibodies, in particular a P1X-related antibody, a P2X-related antibody and a P3X-related antibody, which bind to different EGFR epitopes, formulated at a specific 2:2:1 ratio. In addition to the three antibodies, these pharmaceutical compositions can comprise a pharmaceutically acceptable carrier and/or other excipient(s) such as those described in detail above. The pharmaceutical composition can be supplied in a single container containing all three antibodies or, alternatively, the pharmaceutical composition can comprise a package comprising three distinct containers each containing one of the three different anti-EGFR antibodies (as well as a pharmaceutically acceptable carrier and/or other excipient(s) as described above).

Uses of the above-described anti-EGFR antibodies are provided, either alone (as single agents), in pair combinations (two antibodies), or in triple combinations (three antibodies) in the manufacture of a medicament for the treatment of a disease associated with EGFR dependent signaling. The above-described anti-EGFR antibodies are also provided, either alone (as single agents), in pair combinations (two antibodies), or in triple combinations (three antibodies) for the treatment of cancer (or to be used in the manufacture of a medicament for the treatment of cancer), such as an EGFR-expressing cancer, such as a cancer including, but not limited to melanoma, breast cancer, ovarian cancer, renal carcinoma, gastrointestinal cancer, colon cancer, lung cancer, pancreatic cancer, skin cancer, head and neck cancer glioblastoma, prostate cancer and other solid and/or metastatic tumors.

Additionally, contemplated compositions may further include, or be prepared for use as a medicament in combination therapy with, an additional therapeutic agent, e.g., an additional anti-cancer agent. An "anti-cancer agent" is a drug used to treat tumors, cancers, malignancies, and the like. Drug therapy (e.g., with antibody compositions disclosed herein) may be administered without other treatment, or in combination with other treatments such as surgery, heat, or radiation therapy (e.g., with ionizing radiation). Several classes of anti-cancer agents may be used in cancer treatment, depending on the nature of the organ or tissue involved. For example, breast cancers are commonly stimulated by estrogens, and may be treated with drugs which inactive sex hormones. Similarly, prostate cancer may be treated with drugs that inactivate androgens. Anti-cancer agents for use in combination with antibody compositions disclosed herein include, among others, those listed in Appendix A, which should not be construed as limiting. One or more anti-cancer agents may be administered either simultaneously or before or after administration of an antibody composition disclosed herein. Antibody compositions disclosed herein can be administered sequentially or together with the additional anti-cancer agent, e.g., an anti cancer agent disclosed in Appendix A, below.

Also provided are kits comprising one or more anti-EGFR antibodies disclosed herein, optionally contained in a single vial or container, and include, e.g., instructions for use in treating or diagnosing a disease associated with EGFR upregulation and/or EGFR dependent signaling (e.g., a cancer such as those described in subsection VI below). The kits may include a label indicating the intended use of the contents of the kit. The term label includes any writing, marketing materials or recorded material supplied on or with the kit, or which otherwise accompanies the kit. Such kits may comprise the antibody composition in unit dosage form, such as in a single dose vial or a single dose pre-loaded syringe. Kits comprising a combination of the anti-EGFR antibodies disclosed herein (e.g., a combination of a P1X-related antibody, a P2X-related antibody, and a P3X-related antibody) can comprise a single vial containing all components of the combination or, alternatively, the kit can comprise each component in separate vials with instructions for administration of the antibodies in combination therapy. In a preferred embodiment, a P1X-related antibody, a P2X-related antibody, and a P3X-related antibody are supplied in a 2:2:1 ratio in a single vial or, alternatively, are supplied each in separate vials with instructions for administering the three antibodies at a 2:2:1 ratio.

VI. Methods of Using Antibodies

Antibodies and compositions disclosed herein can be used in a broad variety of therapeutic and diagnostic applications, particularly oncological applications. Accordingly, in another aspect, provided herein are methods for inhibiting EGFR activity in a subject by administering one or more antibodies or compositions described herein in an amount sufficient to inhibit EGFR-mediated activity. Particular therapeutic indications which can be treated include, for example, cancers of organs or tissues such as skin, brain and central nervous system, head and neck, esophagus, stomach, colon, rectum, anus, liver, pancreas, bile duct, gallbladder, lung or bronchus, breast, ovary, uterus, cervix, vagina, testis, germ cells, prostate, kidney, ureter, urinary bladder, adrenal, pituitary, thyroid, bone, muscle or other connective tissues, leukemia, multiple myeloma, Hodgkin's lymphoma and non-Hodgkin's lymphoma.

Antibodies of disclosed herein also can be used to diagnose or prognose diseases (e.g., cancers) associated with EGFR, for example, by contacting one or more antibodies, antibody pairs or antibody trios disclosed herein (e.g., ex vivo or in vivo) with cells from the subject, and measuring the level of binding to EGFR on the cells, wherein abnormally high levels of binding to EGFR indicate that the subject has a cancer associated with EGFR.

Also provided are methods of using the anti-EGFR antibodies disclosed herein in a variety of ex vivo and in vivo diagnostic and therapeutic applications involving EGFR dependent signaling, including a variety of cancers.

Accordingly, in one embodiment, a method is provided for treating a disease associated with EGFR dependent signaling by administering to a subject an antibody or preferably a combination of antibodies provided herein in an amount effective to treat the disease. Suitable diseases include, for example, a variety of cancers including, but not limited to, melanoma, breast cancer, ovarian cancer, renal carcinoma, gastrointestinal cancer, colon cancer, lung cancer, pancreatic cancer, skin cancer, head and neck cancer glioblastoma, prostate cancer and other solid and/or metastatic tumors.

The antibody can be administered alone or with another therapeutic agent that acts in conjunction with or synergistically with the antibody to treat the disease associated with EGFR mediated signaling. Such therapeutic agents include those described herein, for example, small organic molecules, monoclonal antibodies, bispecific antibodies, recombinantly engineered biologics, RNAi compounds, tyrosine kinase inhibitors, and commercial antibodies, as well as anticancer agents (e.g., cytotoxins, chemotherapeutic agents, small molecules and radiation). Non-limiting examples of anti-cancer agents that can be used in combination therapy with one or more of the anti-EGFR antibodies disclosed herein include, for example, the anti-ErbB3 antibody MM-121 and irinotecan. Further non-limiting examples are listed in Appendix A.

In one embodiment, the antibody is coadmistered with another antibody or agent. Coadministration includes simultaneous administration of the compounds in the same or different dosage form, or separate administration of the compounds (e.g., sequential administration). For example, two or more of the antibodies can be simultaneously administered together (e.g., formulated together). Alternatively, the antibodies can be administered in combination (e.g., formulated separately and administered concurrently or sequentially). For example, a first antibody can be administered followed by the administration of a second antibody, or vice versa. Such concurrent or sequential administration preferably results in the two or more compounds or antibodies being simultaneously present in treated patients.

Other embodiments are described in the following non-limiting Examples.

EXAMPLES

Materials and Methods for the Examples

In general, in the following examples, unless otherwise indicated, conventional techniques of chemistry, molecular biology, recombinant DNA technology, immunology (especially, e.g., antibody technology), and standard techniques in recombinant immunoglobulin preparation were used.

Cell Lines

All the cell lines to be used in the experiments described below are obtained from the National Cancer Institute (NCI), Cell Lines Service (CLS), Sigma-Aldrich Co. LLC. (Sigma), or ATCC.

analysis of the EGFR-ECD structure (Protein Data Bank ID: 1NQL; Ferguson K. M. et al. *Mol Cell.* 11: 507-517, 2003). Residues are mutated to alanines as noted in the protein sequences included in this application. DNA synthesis of expression constructs may be commercially obtained from DNA2.0 (www.dna20.com). Subsequent DNA subcloning, protein expression in 293F cells and protein purification are completed using conventional methods.

Inhibition of EGF-Mediated Signaling of EGFR or ERK in Tumor Cells

Inhibition of ligand-mediated tumor cell signaling is investigated as follows: A431 or Du145 cells are seeded at a density of 35,000 cells/well or 17,500 cells per half well in 96 well tissue culture plates and grown in DMEM or RPMI-1640 medium supplemented with antibiotics, 2 mM L-glutamine and 10% fetal bovine serum (FBS) for 24 hours at 37° C. and 5% carbon dioxide. Cells are serum starved in 1% FBS medium with antibiotics and 2 mM L-glutamine for about 20 hours at 37° C. and 5% carbon dioxide. Cells are then preincubated with varying concentrations of anti-EGFR antibodies for 2 hrs, and then stimulated with human EGF ligand (50 ng/ml) (PeproTech, cat # AF-100-15) for 10 minutes at 37° C. and 5%/carbon dioxide. Cells are washed with ice-cold PBS and lysed in 50 µl ice-cold Lysis buffer (Mammalian Protein Extract Lysis buffer (MPER-Pierce, #78505) amended with 150 mM NaCl and protease inhibitor cocktail (Sigma, P714)) by incubating on ice for 30 minutes. Lysates are either analyzed immediately by ELISA for ERK (a downstream effector of EGFR) and EGFR phosphorylation, or frozen at −80° C. until use.

ELISA Assays

For the phospho-EGFR sandwich ELISA, 96-half well GREINER high binding plates (Cat. #675077; GREINER BIO-ONE, Monroe, N.C.) are coated with 50 µL of an

TABLE 0

Cell Lines:

| Cell Line | Source | Catalog # | Type |
| --- | --- | --- | --- |
| A431 | ATCC | ATCC ® CRL-1555 ™ | human epidermoid carcinoma |
| DU145 | ATCC | ATCC ® HTB-81 ™ | human prostate carcinoma |
| H1975 | ATCC | ATCC ® CRL-5908 ™ | human lung non-small cell lung adenocarcinoma |
| HCC827 | ATCC | ATCC ® CRL-2868 ™ | human lung non-small cell lung adenocarcinoma |
| A549 | ATCC | ATCC ® CCL-185 ™ | human lung carcinoma |
| BxPC-3 | ATCC | ATCC ® CRL-1687 ™ | human pancreatic adenocarcinoma |
| NCI-H1355 | ATCC | ATCC ® CRL-5865 ™ | human lung adenocarcinoma |
| NCI-H226 | ATCC | ATCC ® CRL-5826 ™ | human lung squamous cell carcinoma/mesothelioma |
| NCI-H322M | Sigma | 95111734 | human lung non-small cell lung adenocarcinoma |
| NCI-H358 | ATCC | ATCC ® CRL-5807 ™ | human lung bronchioalveolar carcinoma; non-small cell lung cancer |
| HCT 116 | ATCC | ATCC ® CCL-247 ™ | human colon carcinoma |
| HOP-62 | NCI | | human lung carcinoma |
| HT-1197 | ATCC | ATCC ® CRL-1473 ™ | human bladder carcinoma |
| HT-29 | ATCC | ATCC ® HTB-38 ™ | human colorectal adenocarcinoma |
| LoVo | ATCC | ATCC ® CCL-229 ™ | human colorectal adenocarcinoma |
| RT-112 | CLS | 300324 | human bladder carcinoma |
| SCaBER | ATCC | ATCC ® HTB-3 ™ | human bladder squamous cell carcinoma |
| SK-MES-1 | ATCC | ATCC ® HTB-58 ™ | human lung squamous cell carcinoma |
| SW 900 | ATCC | ATCC ® HTB-59 ™ | human lung squamous cell carcinoma |

Protein Purification of EGFR Extracellular Domain (EGFR-ECD) Mutants

Mutants of the EGFR extracellular domain (EGFR-ECD) are generated for mAb epitope binning. Mutations were designed based upon both the cetuximab (Li S. et al., *Cancer Cell.* 7: 301-311, 2005) and H11 (Spangler J. et al. *PNAS.* 107: 13252-13257, 2010) epitopes and upon structural EGFR antibody (EGFR Ab-11, Clone: 199.12, without BSA and azide, Fisher Scientific, cat# MS396P1ABX), and incubated overnight at room temperature. The next morning, the plates are washed 3 times with 100 µl/well PBST (0.05% Tween-20) on a BIOTEK plate washer. Plates are subsequently blocked for about 1 hour at room temperature with 2% BSA in PBS. The plates are washed 3 times with 100

μl/well PBST (0.05% Tween-20) on the BIOTEK plate washer. Cell lysates (50 μl) or standards (pEGFR pY1068 ELISA kit, R&D Systems, cat# DYC3570) are diluted in 50% Lysis buffer and 1% BSA-PBS (per the manufacturer's recommendations) and are added to the plates in duplicates and incubated for 2 hrs at room temperature or overnight at 4° C. with shaking. Plates are then washed 3 times with 100 μl/well in the BIOTEK plate washer with PBST (PBS with 0.05% Tween-20). About 50 μl of a detection antibody conjugated to horse radish peroxidase (HRP) (pEGFR pY1068 ELISA kit, R&D Systems, cat# DYC3570) diluted in 2% BSA, PBS is added and incubated for about 2 hour at room temperature. The plate is washed 3 times with 100 μl/well in the BIOTEK plate washer with PBST (0.05% Tween-20). About 50 μL of SUPERSIGNAL PICO ELISA substrate is added and the plate is read using an Envision (Perkin Elmer) plate reader. For data analysis, duplicate samples are averaged and error bars are used to represent the standard deviation between the two replicates. Inhibition curves and corresponding IC50 values are calculated using GraphPad Prism software (GraphPad Software, Inc.) via regression of the data to a 4 parameter logistic equation.

The phospho-ERK ELISA is performed similarly to the phospho-EGFR ELISA with the following changes: Human pERK ELISA Duoset kit is purchased from R&D Systems (cat# DYC1018-5) and used as recommended by the manufacturer.

A direct ELISA is performed using EGFR-ECD wild-type (WT), a Bin1 epitope mutant, or a Bin3 epitope mutant as capture reagents (4 μg/ml). 96-half well GREINER high binding plates (Cat. #675077; GREINER BIO-ONE, Monroe, N.C.) are coated with 50 μL of capture reagent and incubated overnight at room temperature. Next morning, plates are washed 3 times with 100 μl/well in a BIOTEK plate washer with PBST (0.05% Tween-20) and blocked for about 1 hour at room temperature with 1% BSA in PBS, pH7.2. Varying concentrations (1, 0.25, 0.06, and 0.02 μg/ml) of monoclonal antibodies (mAbs) diluted in 1% BSA in PBS, pH7.2 are incubated with the capture reagents at room temperature for 2 hours, followed by detection with 1:50,000 dilution in 1% BSA in PBS, pH7.2 of Peroxidase-Conjugated AffiniPure Goat Anti-Human IgG Fc Fragment (Jackson Immunoresearch Catalog #109-035-008) for 2 hours. About 50 μL of Supersignal PICO ELISA substrate is added and the plate is read using an Envision (Perkin Elmer) plate reader. For data analysis, duplicate samples are averaged and error bars are used to represent the standard deviation between the two replicates.

Binding Affinity: Kinetic Exclusion Assay (KinExA)

Affinities and cross reactivity of antibodies are measured in solution with recombinant EGF receptor using KinExA instrumentation (SAPIDYNE Instruments, Boise, Id.). Materials used for this assay are a KinExA 3000 instrument and software (Sapidyne Instruments, Boise, Id.), polymethylmethacrylate (PMMA) beads (Sapidyne Instruments), human anti-EGFR IgG, recombinant human EGFR, Cy5-conjugated goat anti-human IgG (Jackson ImmunoResearch, West Grove, Pa.), phosphate buffered saline (PBS), and bovine serum albumin in PBS (100 mg/ml).

To couple the recombinant EGF receptor to PMMA beads, 100 μg of recombinant EGFR is added to a pre-measured aliquot of 200 mg PMMA beads, and PBS is added to make the total volume 1 ml. The beads are incubated for 1 hr at room temperature on a rotating wheel. Then the beads are briefly centrifuged and the supernatant is removed. 100 μl of 100 mg/ml BSA in PBS is added to the beads, with further addition of PBS to make a total volume of 1 ml. The beads are incubated again for 1 hr at room temperature on a rotating wheel. The beads are then transferred to a glass bottle containing 27 mL of PBS.

To determine the monovalent antibody binding affinity, a twelve-step dilution series of recombinant EGFR (75 nM, 25 nM, 8.3 nM, 2.8 nM, 0.9 nM, 0.3 nM, 100 pM, 33 pM, 11 pM, 4 pM, 1.3 pM, 0 pM) is prepared in 5 ml PBS having a constant concentration of anti-EGFR antibody. For accurate affinity measurement, the total antibody binding site concentration ("ABC"; twice the molar concentration of antibody, due to valence) should be less than the monovalent affinity of the antibody for EGFR. The antibody-receptor mixtures are incubated for 2 hr at room temperature in order to achieve equilibrium. Depending upon the expected affinity of the antibody-receptor complex, this equilibration time may be adjusted accordingly. In a separate tube, 15 mL of 2 μg/mL Cy5-conjugated anti-human IgG secondary antibody is prepared, using a 1:1000 dilution of stock (2 mg/mL) antibody into PBS. Then, the KinExA instrument lines are attached to each of the 12 antibody-receptor solution tubes. Each solution is injected through a packed EGFR-bead column. (The KinExA instrument automatically packs a fresh bead column for each injection.) After a wash step, the labeled secondary antibody is passed through the column. Finally, using the measured amount of uncomplexed receptor at different receptor concentrations, the equilibrium titration data is fit to a 1:1 binding model in the KinExA software to yield an affinity value $K_D$. The lower the value of $K_D$ the better (stronger, sometimes stated as higher) the binding affinity. Therefore a recitation that an antibody binds with a $K_D$ of x nM or better means it binds with a $K_D$ value of, e.g., $1 \times 10^{-8}$ M (10 nM) or with a lower $K_D$ value, e.g., $1 \times 10^{-10}$ M (0.1 nM), with the lower $K_D$ value indicating better (higher) affinity.

To determine the binding on-rate using the KinExA "direct method", the equilibrium monovalent binding affinity ($K_D$) is determined using the above approach and total antibody binding site concentration (ABC). Then, using the "Theoretical Binding Curve Demonstration" software (Sapidyne Instruments), the starting antigen concentration (L0) is determined for the kinetics experiment. To do this, the affinity and ABC values determined in the monovalent binding affinity experiment are entered, and a starting antigen concentration is selected as that concentration where roughly 20% of antibody will be unbound to antigen at equilibrium. This assures good signal-to-noise ratio in the experiment. 15 mL of 2 μg/mL Cy5-conjugated anti-human IgG secondary antibody is prepared, using a 1:1000 dilution of stock (2 mg/mL) antibody into PBS. In a separate tube, 8 mL of anti-EGFR antibody solution is prepared at a concentration of 2×ABC. This concentration is double the running concentration, since it is mixed with 8 mL of antigen solution prior to the experiment. In a separate tube, 8 mL of recombinant EGFR solution is prepared at a concentration of 2×L0. This concentration is also double the running concentration, since it is mixed with 8 mL of antibody solution prior to the experiment. Then, the EGFR coated beads and secondary antibody solution are placed in the appropriate container and line, respectively. The antibody and antigen solution are mixed thoroughly and immediately connected to the appropriate line, and the KinExA software is used to measure the amount of free antibody as a function of time in the resulting solution. To determine the association constant $k_{on}$ (Kon), the KinExA software is used to fit the depletion of the amount of free antibody as a function of time to a reversible bimolecular rate equation. The dissociation constant $K_{off}$ (Koff) is equal to the $K_{on}*K_D$ (Kd).

Binding Affinity: Surface Plasmon Resonance Assay

The Surface Plasmon Resonance Assay is performed as follows:

either antibody or antigen (300 RU) is immobilized on a CM5 chip using amine coupling. Different concentrations of antibodies or antigens are then injected to study their association and dissociation with the immobilized protein. Between different injections, the chip is regenerated using suitable regeneration buffer (such as glycine, pH 2.5). The dissociation phase is fitted using Equation 1 to determine $K_{off}$ (dissociate rate):

$$R=R_o*\exp(-K_{off}*t) \quad (1)$$

The association phase is fitted using this value of $K_{off}$ and Equation 2 to determine $K_{on}$ (association rate) and $K_D$ (equilibrium constant).

$$R = \frac{R_{max} * C}{K_D + C}(1 - \exp(-(K_{on} * C + K_{off})t)) \quad (2)$$

where C represents either the antigen or antibody concentration in solution, $R_{max}$ represents the saturation signal and t represents the time.

Epitope Binning: Surface Plasmon Resonance Assay

Epitope binning is performed using surface plasmon resonance assay, as described above. One of the antibodies is immobilized on the surface of the chip. Recombinantly expressed human EGFR extracellular domain (EGFR-ECD) is then injected. As EGFR-ECD associates with the antibody conjugated to the surface of the chip, the resonance signal increases. Sequential injections of antibodies that belong to the three bins 1, 2 and 3 are performed. If the antibody binds overlapping epitopes with the injected antibody, then the signal will not change compared to the previous injection. If the antibody binds to a non-overlapping epitope, the signal on the chip will be higher than the previous injection. The antibody conjugated to the chip is finally injected as free ligand to confirm lack of binding with overlapping epitopes.

Cell Binding Assay Cell binding assays for determining the $K_D$ values are performed as follows: A431 cells are detached with 3 mLs trypsin-EDTA at 37° C. for 5 minutes. Complete DMEM (10 mLs) is added immediately to the trypsinized cells, resuspended gently and spun down in a Beckman tabletop centrifuge at 1100 rpm for 5 minutes. Cells are resuspended in stain buffer (PBS+0.2% BSA+0.1% sodium azide) at a concentration of $2 \times 10^6$ cells per ml and 50 μl ($1 \times 10^5$ cells) aliquots are plated in a 96-well titer plate.

A 300 μl stock solution of 2000 nM anti-EGFR antibody is prepared in stain buffer and 100 μl of it is serially diluted into 200 μl of stain buffer. The concentrations of the diluted antibody range from 2000 nM to 0.1 nM. 150 μl aliquots of the different protein dilutions are then added directly to the 50 μl cell suspension giving final concentrations of 1500 nM, 500 nM, 166.7 nM, 55.6 nM, 18.5 nM, 6.17 nM, 2.05 nM, 0.68 nM, 0.23 nM and 0.076 nM antibody.

Aliquoted cells in the 96-well plate are incubated with the antibody dilutions for 2 hr at room temperature with shaking and washed 3 times with 300 μl stain buffer. Cells are then incubated with 100 μl of a 1:750 dilution of Alexa 647-labeled goat anti-human IgG in BD stain buffer for 45 minutes with shaking at 4° C. Finally, cells are washed twice, pelleted and resuspended in 250 μl stain buffer+0.5 μg/ml propidium iodide. Analysis of 10,000 cells is done in a FACSCALIBUR flow cytometer using the FL4 channel. MFI values and the corresponding concentrations of the anti-EGFR-antibodies are plotted on the y-axis and x-axis, respectively. The $K_D$ of the molecule is determined using GRAPHPAD PRISM software using the one-site binding model for a non-linear regression curve.

The $K_D$ value is calculated based on the formula $Y=B\max*X/K_D+X$ ($B$max=fluorescence at saturation. $X$=antibody concentration. $Y$=degree of binding).

Measurement of EGFR Levels via Immunoblotting

To prepare cell lysates, H1975 cells are trypsinized, harvested, counted, and plated in 6 well dishes at $1 \times 10^6$ cells per well and incubated overnight to allow attachment to the culture plate. Cells are pre-treated with 1 μM concentration of P1X+P2X+P3X (P1X+P2X+P3X or P1X, P2X, & P3X indicates a combination at a 2:2:1 molar ratio of P1X, P2X, and P3X) for 1, 2, 5, and 24 hours before stimulation with rhEGF (Peprotech, cat#100-15) for 10 minutes. Cells are lysed with 100 μl of Mammalian Protein Extraction Reagent (Pierce, cat#78505). Protein extraction reagent is supplemented with PhosSTOP (Roche, cat#04906837001) and Protease Inhibitor Cocktail tablets (Roche, cat#04693124001). Extracts of H1975 cells are denatured by boiling for 5 minutes in sample buffer, subjected to reducing conditions, and electrophoresed using SDS-PAGE 4-12% polyacrylamide gels for 50 minutes at 200V. Following transfer of proteins to a nitrocellulose membrane, nonspecific sites are blocked by incubation with Odyssey blocking buffer (LI-COR, cat#927-400-00) for one hour at room temperature. Membranes are incubated as required with mouse monoclonal anti-EGFR (1F4—labeling tEGFR; Cell Signaling, cat#2239); rabbit monoclonal anti-phospho44/42 MAPK (Erk1/2, Thr202/Tyr204, D13.14.4E—labeling pERK; Cell Signaling, cat#4370); rabbit monoclonal anti-phosphoAKT (Ser473, 193H12; Cell Signaling, cat#4058); rabbit monoclonal phospho-c-Jun (Ser73, D47G9—labeling p-c-Jun; Cell Signaling, cat#3270) and rabbit anti-PCNA (FL-261) (Santa Cruz Biotechnology, cat# sc-7907). Following overnight incubation with the primary antibodies, immunoblots are incubated with the appropriate IRDye-labeled secondary antibody (IR800CW goat anti-mouse (Odyssey, cat#926-3210) or IR800CW goat anti-rabbit (Odyssey, cat#926-3211)) for 10 minutes and vacuumed through the membrane using SNAP i.d., Protein Detection System (Millipore). Bands are detected using LI-COR Odyssey Infrared Imaging System and analyzed using Odyssey software.

Inhibition of Tumor Cell Proliferation In Vitro

Inhibition of cellular proliferation of cells expressing EGFR is examined in vitro as follows: HCC827 and H1975 cancer cells are seeded in 96 well tissue culture plates at 5,000 cells per well and grown in RPMI-1640 medium supplemented with antibiotics, 2 mM L-glutamine and 10% fetal calf serum (FCS) for 24 hours at 37° C. and 5% carbon dioxide. Medium is then switched to RPMI-1640 (with antibiotics, 2 mM L-glutamine, 1% FBS) supplemented with 50 ng/mL EGF or 200 ng/ml AREG (amphiregulin; R&D Systems) in the presence of varying concentrations of P1X+P2X+P3X or cetuximab (Bristol-Myers Squibb). Cell viability is measured using the CellTiter-Glo® (CTG) Luminescent Cell Viability Assay (Promega Corporation, cat# G7572) according to manufacturer's instructions. The CTG assay measures the number of viable cells in culture based upon quantitation of ATP present, which is an indicator of metabolically active cells. Control treatments include cells treated with RPMI-1640 with antibiotics, 2 mM L-glutamine, 1% FCS in the presence (referred to as "+EGF" or "+AREG") or absence (referred to as "−EGF" or "−AREG") of 50 ng/mL EGF or 200 ng/ml AREG.

Inhibition of Tumor Cell Proliferation In Vitro with Drug Combinations

Inhibition of cellular proliferation of cells expressing EGFR with combinations of therapeutic agents is examined in vitro as follows: indicated cancer cells are seeded into 96-well low-binding round-bottom tissue culture plates (Corning #7007) at the indicated cell number per well and grown in RPMI-1640 medium supplemented with antibiotics, 2 mM L-glutamine, 5 or 10% fetal calf serum (FCS) and indicated ligand(s), each at 5 nM, for 24 hours at 37° C. and 5% carbon dioxide. Therapeutic agents, alone or in combination, are then added in varying concentrations as indicated in figures in the same supplemented medium, and plates are allowed to incubate for 3 or 5 days at 37° C. and 5% carbon dioxide. Cell viability is measured using the CellTiter-Glo® (CTG) Luminescent Cell Viability Assay (Promega Corporation, cat# G7572) according to manufacturer's instructions. Control treatments include cells treated with RPMI-1640 with antibiotics, 2 mM L-glutamine, 5 or 10% FCS and indicated ligands, each at 5 nM.

Inhibition of cell proliferation with combinations of P1X+P2X+P3X with MM-121 is examined by the above protocol with the following modifications: cells are seeded at 5,000 cells/well and RPMI-1640 medium is supplemented with antibiotics, 2 mM glutamine, 5% FCS, 5 nM EGF and 5 nM heregulin (hereafter "HRG").

Inhibition of cell proliferation with combinations of P1X+P2X+P3X with docetaxel (hereafter "DTX") is examined by the above protocol with the following modifications: cells are seeded at 5,000 cells/well and RPMI-1640 medium is supplemented with antibiotics, 2 mM glutamine, 5% FCS and 5 nM EGF.

Inhibition of cell proliferation with combinations of P1X+P2X+P3X with SN-38 is examined by the above protocol with the following modifications: cells are seeded at 2,500 cells/well and RPMI-1640 medium is supplemented with antibiotics, 2 mM glutamine, 10% FCS and 5 nM EGF.

DU145 & H1975 Mouse Xenograft Studies

Nu/nu mice (Charles River Labs) are injected subcutaneously with cells. The resultant tumors are allowed to grow until they reach an average size of 300 mm$^3$. Dosing is then initiated with the indicated concentrations of combinations of P1X with P2X, and P3X, cetuximab or matched volume of PBS as vehicle control. Measurements are taken at 4 day intervals and tumor volumes calculated using the formula Volume=$\pi/6 \times (W \times L^2)$. Cetuximab and P1X+P2X+P3X doses are normalized to provide uniform serum exposures.

Efficacy of a combination of P1X with P2X, and P3X in vivo is assessed in a DU145 prostate cancer cell xenograft murine mouse model. 8×10$^6$ DU145 cells are injected subcutaneously into the flank of nu/nu mice. Once tumors reach an average size of 300 mm$^3$, treatment is initiated. Groups of 10 mice are treated with either vehicle control (PBS); 2.075 mg/kg of cetuximab, P1X with P2X, and P3X at component concentrations that were at a "murine ratio" designed to provide a 2:2:1 serum drug exposure for P1X, for P2X and for P3X, respectively, in the mouse, as follows: P1X=2.53 mg/kg, P2X=7.26 mg/kg and P3X=0.66 mg/kg. Mice in the cetuximab group are dosed every four days. Mice in the P1X+P2X+P3X group are dosed every two days. These doses and dosing intervals are chosen to give an equivalent serum exposure of cetuximab and the murine ratio antibody trio.

Patient Derived Colorectal Cancer Tumor Xenograft Study

The following example employs a bin 1 antibody, "ca", which is the parental antibody to the bin 1 antibody P1X. This antibody is described in co-pending patent application "Antibodies Against Epidermal Growth Factor Receptor (EGFR) and Uses Thereof", Publication No. US 2011-0287002, which is herein incorporated by reference.

Efficacy of a combination of ca+P2X+P3X in vivo is assessed in a patient derived colorectal cancer tumor xenograft murine mouse model (PDX model #ST094, South Texas Accelerated Research Therapeutics Discovery). In these human xenograft in mouse host experiments, antibody ca was substituted for antibody P1X because P1X, but not ca, cross reacts with (binds to) mouse EGFR as well as binding to human EGFR, and the binding of P1X to the mouse antigen depletes the amount of this antibody in the mouse circulation, altering exposure of the human tumor to the antibody. Results obtained with ca are predictive of results that would be obtained in human patients with P1X, except that the antibody trio comprising P1X would be expected to be more active than the trio comprising ca in its stead.

Fragments of tumors are implanted subcutaneously into the flank of female immune-deficient mice. Once tumors reach an average size of 125-225 mm$^3$, treatment is initiated. Groups of 10 mice are treated by intraperitoneal injection with either vehicle control (PBS); 100 mg/kg irinotecan; ca+P2X+P3X at component concentrations that were at a "murine ratio" designed to provide a 2:2:1 serum drug exposure for ca, for P2X and for P3X, respectively, in the mouse, as follows: for the first ("loading") dose, ca=40 mg/kg, P2X=28 mg/kg and P3X=20 mg/kg; for the remaining ("maintenance") doses, ca=20 mg/kg, P2X=28 mg/kg and P3X=10 mg/kg. Mice in the irinotecan group are dosed on Days 0, 7, and 14. Mice in the ca+P2X+P3X group are dosed every seven days with ca+P3X and three times per week with P2X. Mice in the [ca+P2X+P3X]+irinotecan combination group are dosed in the same manner as listed for the respective monotherapy groups. Measurements are taken twice weekly and tumor volumes calculated using the formula Volume=$\pi/6 \times (W^2 \times L)$.

Ligand Antagonism Cell Binding Assay

Cell binding assays for determining the binding of EGF ligand in the presence of single or multiple antibodies are performed as follows: A431 cells are detached with 5 mL trypsin-EDTA at 37° C. for 5 minutes. Complete DMEM (10 mL) is added immediately to the trypsinized cells, resuspended gently and spun down in a Beckman tabletop centrifuge at 1200 rpm for 7 minutes. Cells are resuspended in stain buffer (PBS+2% FBS+0.1% sodium azide) at a concentration of 3×10$^5$ cells per ml and 100 µl (3×10$^4$ cells) aliquots are plated in a 96-well titer plate.

A 5 mL 2× stock solution of anti-EGFR antibody is prepared in stain buffer at the concentrations indicated in each example. A 10 mL 3× stock solution of recombinant human EGF ligand conjugated to a biotin tag (biotin-EGF) is prepared in stain buffer and 100 µl of it is serially diluted into 200 µl of stain buffer. The concentrations of the diluted biotin-EGF range from 600 nM to 9 pM. 100 µl aliquots of the anti-EGFR antibody are then added directly to the 100 µl cell suspension giving a final concentration as indicated in each example. Aliquoted cells in the 96-well plate are incubated with the antibody dilutions for 1 hr at room temperature. 100 µl aliquots of the biotin-EGF are then added directly to the 100 µl cell suspension giving a final concentration of 200 nM, 66.67 nM, 22.22 nM, 7.41 nM, 2.47 nM, 0.82 nM, 0.27 nM, 0.09 nM, 0.03 nM, 0.01 nM, and 0.003 nM biotin-EGF. Aliquoted cells in the 96-well plate are incubated with the antibody and biotin-EGF dilutions for 10 min at room temperature, washed 1 time with 100 µl stain buffer, and then spun down in a Beckman tabletop centrifuge at 1200 rpm for 7 minutes. Cells are resuspended in 100 µl of a 1:500 dilution of Alexa Fluor® 647 Streptavidin conjugate (Invitrogen Life Technologies) in stain buffer for 30 minutes at room temperature in the dark. Finally, cells are washed twice with 100 µl stain buffer, pelleted and resuspended in 80 µl fixing buffer (PBS+2% FBS+2% paraformaldehyde) and transferred to 96-well U-bottom Assay Plates (Becton Dickinson) and sealed with foil and stored at 4° C.

Analysis of 10,000 cells is done in a FACSCALIBUR flow cytometer using the FL4 channel. Data are analyzed using WinList 6.0 software. Mean Fluorescence Intensity (MFI) values and the corresponding concentrations of the biotin-EGF ligand are plotted on the y-axis and x-axis, respectively.

Example 1: Epitope Mapping/Binning

Antibodies P1X, P2X, and P3X were generated via affinity maturation of parental antibodies. Respective parental antibodies ca, cd, and ch are disclosed in copending patent application Serial No. PCT/US2011/3528. Epitope mapping and binning experiments were performed to demonstrate that P1X, P2X, and P3X share the same non-overlapping epitopes as their respective parental molecules.

The Bins were designed so that selected antibodies would span three distinct, non-overlapping epitopes on the extracellular domain (ECD) of EGFR. These are grouped into three bins: Bin1 is mapped to Domain III of EGFR and represents the c225 epitope (the site of cetuximab binding); Bin2 is mapped to Domain I and represents the ICR10 epitope (Abcam Ab231) (Cochran et al. (2004) Journal of Immunological Methods, 287:147-158); and Bin3 is mapped to Domain III and represents the clone H11 epitope (Spangler J. et al. *PNAS.* 107: 13252-13257, 2010). Bin1 (B1-7MT-Ala) and Bin3 (B3-4MT) mutants were generated for epitope mapping at the amino acid positions shown below in bold in the EGFR extracellular domain.

Mutants
Bin1 (B1) Mutant Residues
B1-7MT-Ala: Q408A, Q432M, H433E, K467A, K489A, I491A, N497A Bin3 (B3) Mutant Residues
B3-4MT: S380A, F381G, T382A, H383G A direct ELISA was performed using EGFR-ECD wild-type (WT), a Bin1 epitope mutant (c225 epitope), or a Bin3 epitope mutant (H11 epitope) as capture reagents. Varying concentrations (1, 0.25, 0.06, and 0.02 µg/ml) of monoclonal antibodies (mAbs) P1X (Bin1), P2X (Bin2), and P3X (Bin3) were incubated with the capture reagents at room temperature for 2 hours, followed by detection with HRP-conjugated anti-human Fc polyclonal antibody for 1 hour. As shown in FIG. 1A, all three antibodies bound to the WT extracellular domain of EGFR, whereas the Bin1 antibody P1X did not bind to the Bin1 mutant epitope, and the P3X antibody did not bind to the Bin3 mutant epitope.

Figure 1B:
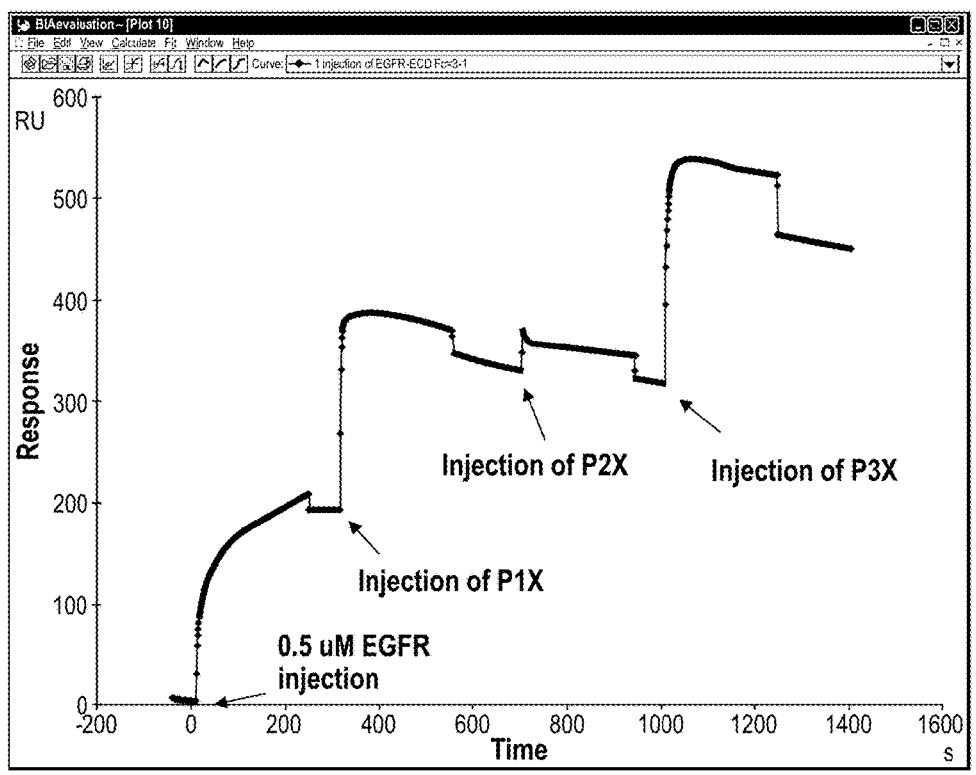
FIG. 1B is a graph showing the results of a surface plasmon resonance epitope binning experiment using the ICR10 epitope (Bin 2) conjugated on a Biacore chip, with injection of wild-type EGFR-ECD antigen, followed by sequential injection of the P1X, P2X and P3X antibodies.

A surface plasmon resonance experiment was performed to demonstrate that P2X associates to the ICR10 epitope on Domain I of EGFR extraceullular domain (FIG. 1B). ICR10 was conjugated to the surface of a BIACORE chip. 0.5 µM EGFR-ECD was injected followed by sequential injections of 0.5 µM of antibodies P1X (Bin1), P2X (Bin2), and P3X (Bin3). While P1X and P3X are observed to simultaneously associate with ICR10-bound EGFR-ECD, P2X is shown to not associate.

Figure 2A:
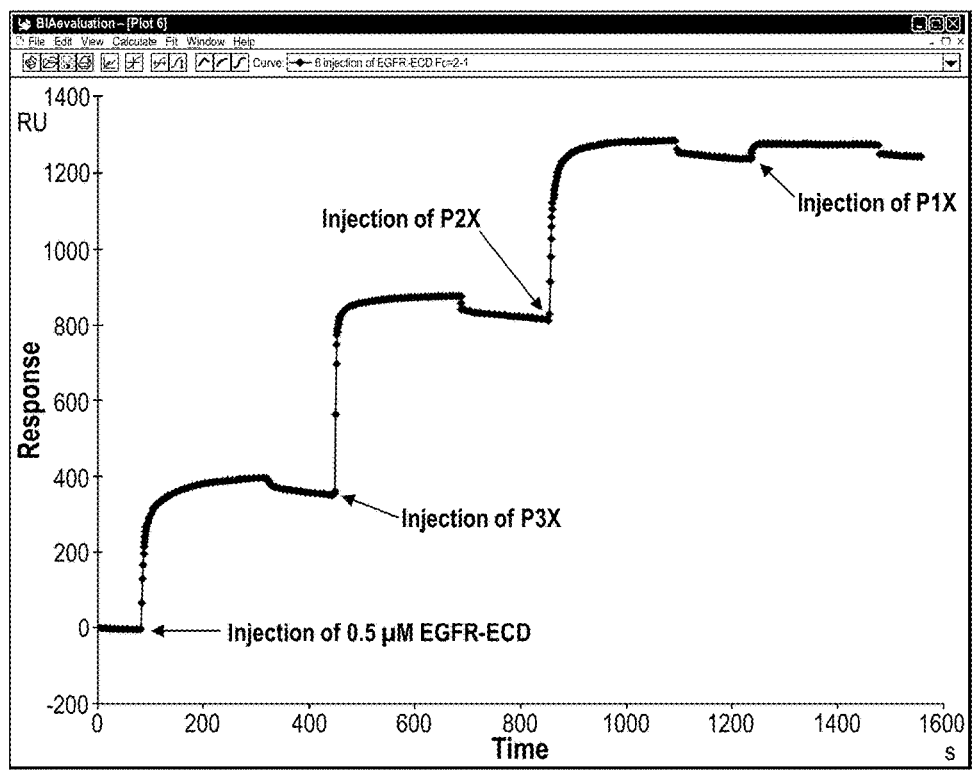
FIG. 2A is a graph showing the results of a surface plasmon resonance epitope binning experiment using the P1X antibody conjugated on a Biacore chip, with injection of wild-type EGFR-ECD antigen, followed by sequential injection of the P3X, P2X and P1X antibodies.
Figure 2B:
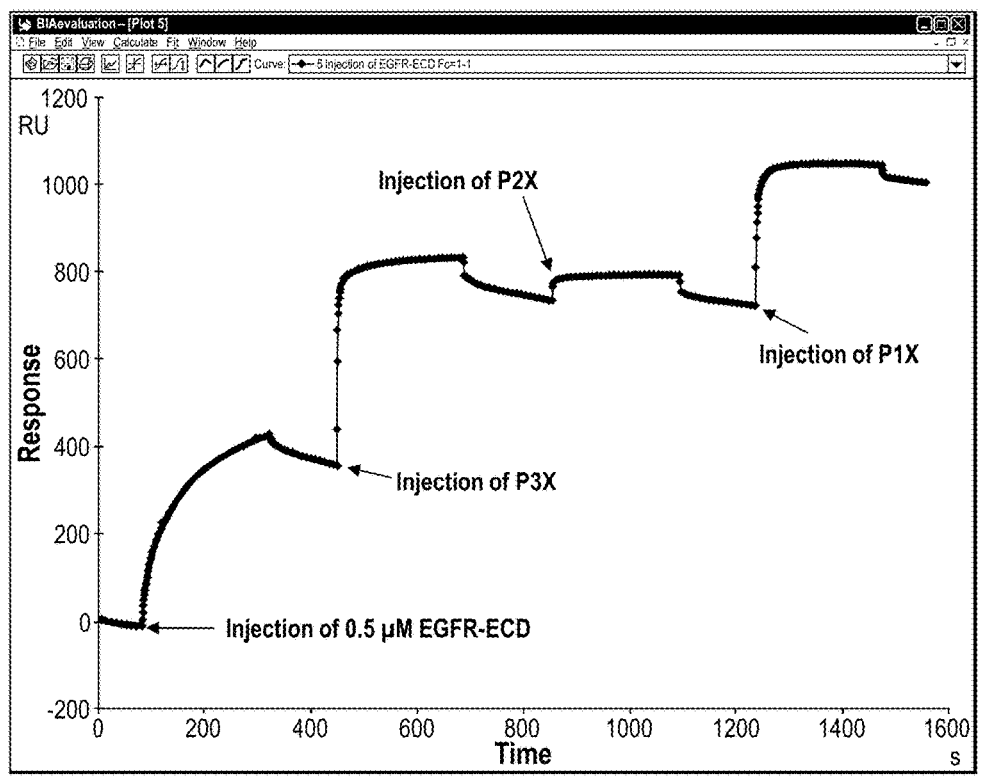
FIG. 2B is a graph showing the results of a surface plasmon resonance epitope binning experiment using the P2X antibody conjugated on a Biacore chip, with injection of wild-type EGFR-ECD antigen, followed by sequential injection of the P3X, P2X and P1X antibodies.
Figure 2C:
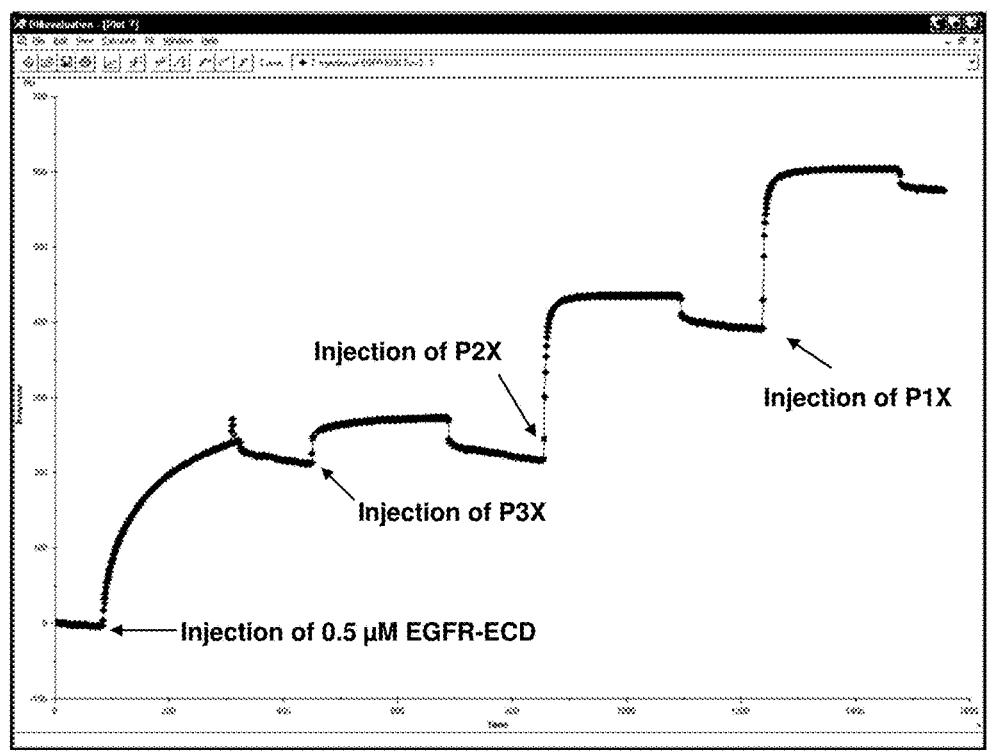
FIG. 2C is a graph showing the results of a surface plasmon resonance epitope binning experiment using the P3X antibody conjugated on a Biacore chip, with injection of wild-type EGFR-ECD antigen, followed by sequential injection of the P3X, P2X and P1X antibodies.

In order to demonstrate that the epitopes for P1X, P2X, and P3X are distinct and non-overlapping, a series of three surface plasmon resonance binning experiments were performed. P1X (FIG. 2A), P2X (FIG. 2B), or P3X (FIG. 2C) were conjugated to the surface of a BIACORE chip. 0.5 µM EGFR-ECD was injected followed by sequential injections of 0.5 µM of antibodies P3X, P2X, and P1X. Injection of the same antibody as conjugated on the BIACORE chip serves as a negative control. In all three experiments, the two antibodies from the remaining bins are observed to associate with EGFR-ECD. Thus, the results of the three experiments demonstrate that P1X, P2X, and P3X have non-overlapping, distinct epitopes and can simultaneously associate with EGFR-ECD.

```
EGFR ECD
                                                            (SEQ ID NO: 33)
  1 MRPSGTAGAA LLALLAALCP ASRALEEKKV CQGTSNKLTQ LGTFEDHFLS LQRMFNNCEV

61 VLGNLEITYV QRNYDLSFLK TIQEVAGYVL IALNTVERIP LENLQIIRGN MYYENSYALA

121 VLSNYDANKT GLKELPMRNL QEILHGAVRF SNNPALCNVE SIQWRDIVSS DFLSNMSMDF

181 QNHLGSCQKC DPSCPNGSCW GAGEENCQKL TKIICAQQCS GRCRGKSPSD CCHNQCAAGC

241 TGPRESDCLV CRKFRDEATC KDTCPPLMLY NPTTYQMDVN PEGKYSFGAT CVKKCPRNYV

301 VTDHGSCVRA CGADSYEMEE DGVRKCKKCE GPCRKVCNGI GIGEFKDSLS INATNIKHFK

361 NCTSISGDLH ILPVAFRGDS FTHTPPLDPQ ELDILKTVKE ITGFLLIQAW PENRTDLHAF

421 ENLEIIRGRT KQHGQFSLAV VSLNITSLGL RSLKEISDGD VIISGNKNLC YANTINWKKL

481 FGTSGQKTKI ISNRGENSCK ATGQVCHALC SPEGCWGPEP RDCVSCRNVS RGRECVDKCN

541 LLEGEPREFV ENSECIQCHP ECLPQAMNIT CTGRGPDNCI QCAHYIDGPH CVKTCPAGVM

601 GENNTLVWKY ADAGHVCHLC HPNCTYGCTG PGLEGCPTNG PKIPSHHHHH H
```

The following substitution mutants were made at the bolded amino acid positions using standard recombinant DNA technology to create the Bin1 (B1) and Bin3 (B3) epitope mutants with the following mutant residues:

Example 2: Binding Affinities

The monovalent affinities of P1X, P2X, and P3X to EGFR were measured by KinExA. Data are shown below in Table 1. Affinities of P1X, P2X, and P3X are all better than 0.4 nM and are all improved relative to the parent molecules. The affinity of P1X (11 pM) is 13.18 times better than the Bin 1 parent molecule ca (145 pM). The affinity of P2X (70 pM) is 7.71 times better than the Bin 2 parent molecule cd (540 pM). The affinity of P3X (360 pM) is 2.10 times better than the Bin 3 parent molecule ch (757 pM).

TABLE 1

| Antibody | Association Rate (1/M * sec) | Dissociation Rate (1/sec) | $K_D$ (M) |
|---|---|---|---|
| P1X | 3.73E+06 | 4.10E−05 | 1.10E−11 |
| ca (P1X parent) | N.D. | N.D. | 1.45E−10 |
| P2X | 7.06E+05 | 4.94E−05 | 7.00E−11 |
| cd (P2X parent) | 9.62E+05 | 5.20E−04 | 5.40E−10 |
| P3X | 1.16E+06 | 4.16E−04 | 3.60E−10 |
| ch (P3X parent) | 5.87E+05 | 4.44E−04 | 7.57E−10 |

Example 3: Cell Binding Assays with Single Antibodies

Figure 3:
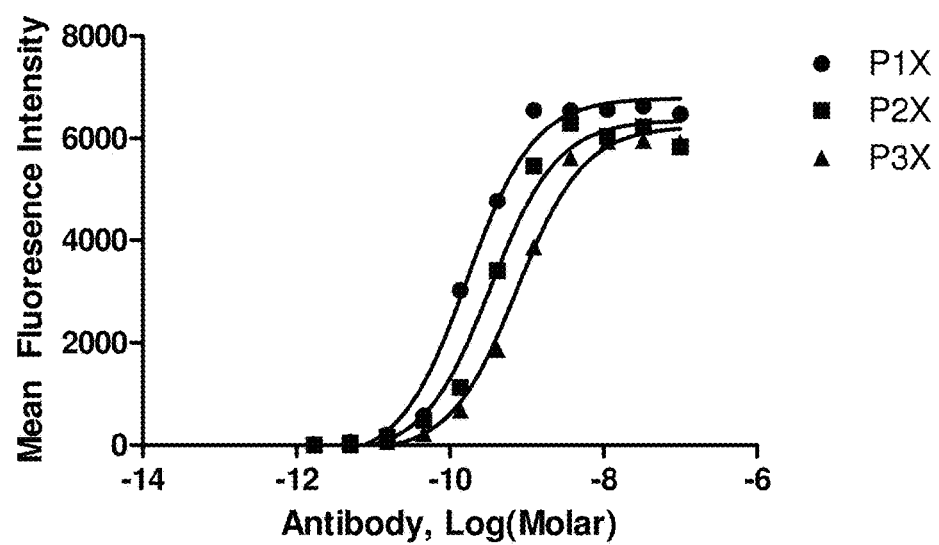
FIG. 3 is a graph showing the results of P1X, P2X and P3X antibody binding kinetics to EGFR on A431 cells as measured via flow cytometry (FACS plot).

A cell binding assay was performed to demonstrate that monoclonal antibodies P1X, P2X, and P3X can associate with EGFR on A431 cells (FIG. 3). A431 cells were incubated with a dilution series of single antibody for 2 hr and the amount of bound antibody measured by quantitative flow cytometry, as described in the methodology section above. The concentrations used in the dilution series for the antibodies are shown below in Table 2. The ordinarily skilled artisan will understand that each specific concentration value in Table 2 is subject to some minor experimental variability, so that each specific concentration given indicates a value of about the indicated concentration (e.g., a concentration indicated in a table as 0.1 nM represents a value of about 0.1 nM).

TABLE 2

| Conc, Log (Molar) | Conc, nM |
|---|---|
| −7.00 | 100.00 |
| −7.48 | 33.33 |
| −7.95 | 11.11 |
| −8.43 | 3.70 |
| −8.91 | 1.23 |
| −9.39 | 0.41 |
| −9.86 | 0.14 |
| −10.34 | 0.05 |
| −10.82 | 0.02 |
| −11.29 | 0.01 |
| −11.77 | 0.00 |

The on-cell binding affinities under these experimental conditions were calculated, via regression to a 4 parameter logistic equation using GraphPad Prism® software, to be 168 pM (P1X), 340 pM (P2X) and 748 pM (P3X).

Example 4: Phospho-EGF Receptor Signaling Inhibition by Single Antibodies

Figure 4:
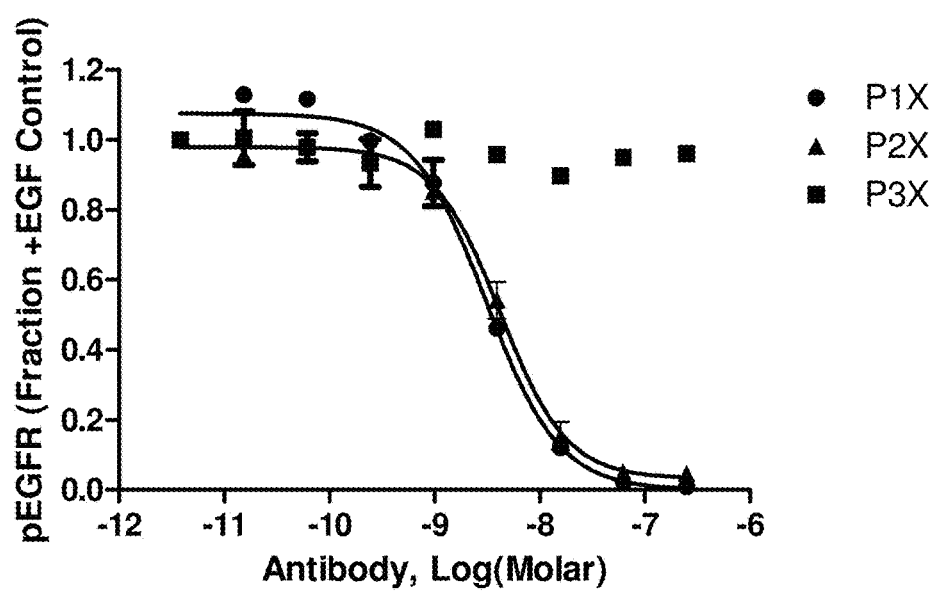
FIG. 4 is a graph showing the results of a phospho-EGFR (pEGFR) ELISA, demonstrating pEGFR inhibition by single antibodies: single-agent treatment with P1X, P2X or P3X antibody.

A431 cells were treated with single antibodies and their ability to inhibit EGF-dependent phospho-EGFR activity was measured by phospho-EGFR ELISA. P1X and P2X potently inhibit phospho-EGFR activity in a dose-dependent manner, with respective IC50 values of 3.09 nM and 4.19 nM, while treatment with P3X elicits partial phospho-EGFR inhibition (FIG. 4). The concentrations used in the dilution series for the antibodies are shown below in Table 3. The ordinarily skilled artisan will understand that each specific concentration value in Table 3 is subject to some minor experimental variability, so that each specific concentration given indicates a value of about the indicated concentration (e.g., a concentration indicated in a table as 0.1 nM represents a value of about 0.1 nM).

TABLE 3

| Conc, Log (Molar) | Conc, nM |
|---|---|
| −6.60 | 250.00 |
| −7.20 | 62.50 |
| −7.81 | 15.62 |
| −8.41 | 3.91 |
| −9.01 | 0.98 |
| −9.61 | 0.24 |
| −10.21 | 0.06 |
| −10.82 | 0.02 |
| −11.42 | 0.00 |

Figure 5A:
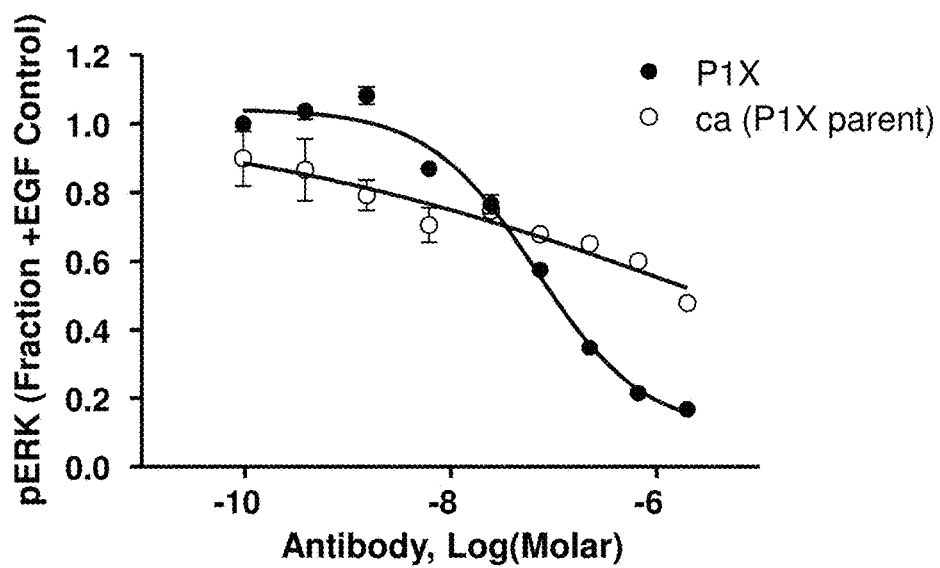
FIG. 5A is a graph showing the results of a phospho-ERK (pERK) ELISA, demonstrating the effect of affinity maturation on pERK inhibition by comparison of pERK inhibition by parental (ca antibody) and affinity matured P1X antibody.

Example 5: Phospho-ERK Signaling Inhibition by Single and Pairwise Combinations of Antibodies and Comparison to Parental Antibodies A431 cells were treated with a dilution series of single P1X or ca antibody and phospho-ERK inhibition measured by phospho-ERK ELISA (FIG. 5A). P1X elicited dose-dependent inhibition of phospho-ERK activity while the ca parental antibody elicited only partial inhibition.

Figure 5B:
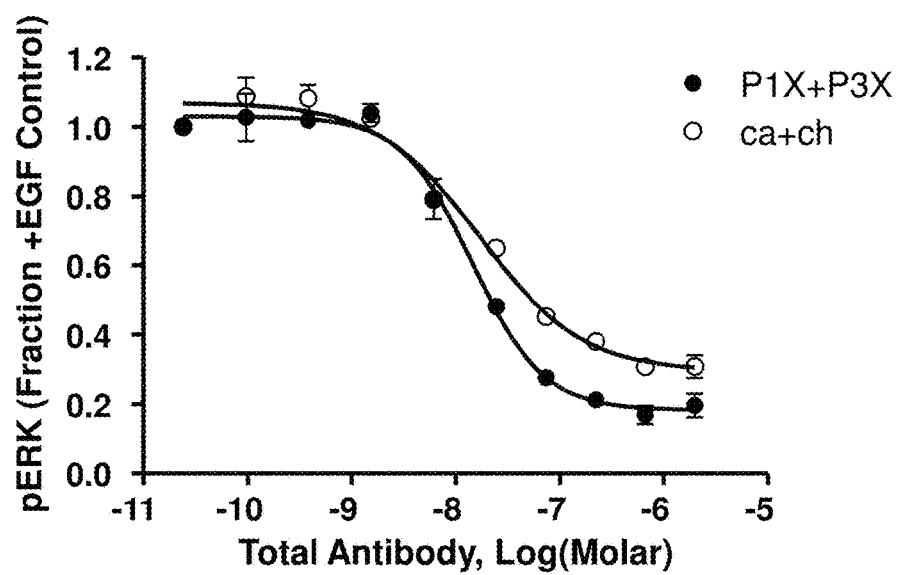
FIG. 5B is a graph showing the results of a phospho-ERK (pERK) ELISA, comparing pERK inhibition by parental (ca and ch antibodies) and affinity matured P1X+P3X antibodies.

A431 cells were treated with a dilution series of pairwise combinations of P1X+P3X or their respective parent antibodies ca+ch and phospho-ERK inhibition measured by phospho-ERK ELISA (FIG. 5B). Both combinations inhibit phospho-ERK generation in a dose-dependent manner, but the combination of P1X+P3X provides superior inhibition. The combination of P1X+P3X elicited 82% inhibition of phospho-ERK activity while the parental combination elicited only 71%, as calculated by a fit to a 4 parameter logistic equation using GraphPad Prism software.

Figure 5C:
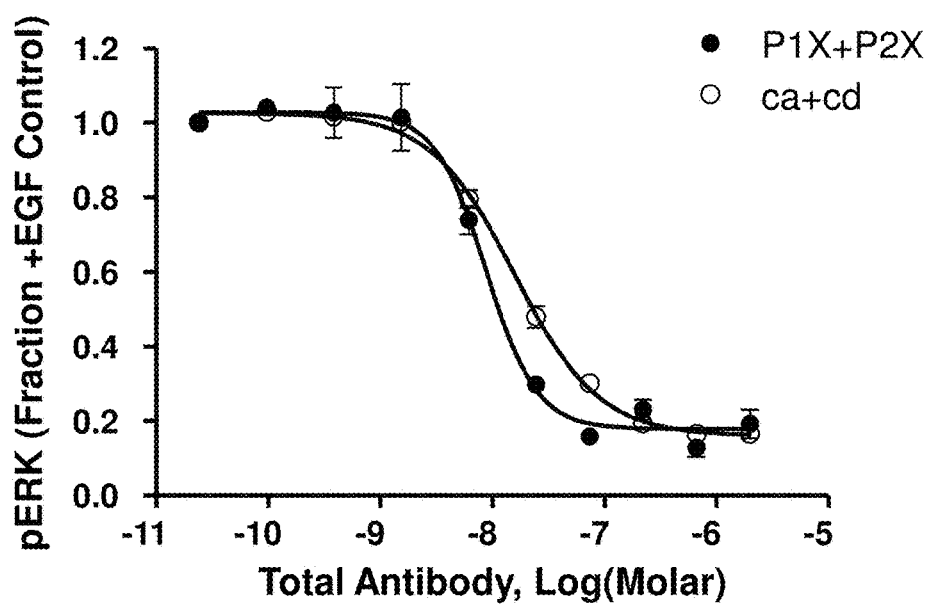
FIG. 5C is a graph showing the results of a phospho-ERK (pERK) ELISA, comparing pERK inhibition by parental (ca and cd antibodies) and affinity matured P1X+P2X antibodies.

A431 cells were treated with a dilution series of pairwise combinations of P1X+P2X or their respective parent antibodies ca+cd and phospho-ERK inhibition measured by phospho-ERK ELISA (FIG. 5C). Both combinations inhibit phospho-ERK generation in a dose-dependent manner, but the combination of P1X+P2X demonstrates an observable improvement in the IC90 value versus the parental combination.

The concentrations used in the dilution series for the antibodies are shown below in Table 4 (for the data in FIG. 5A) and in Table 5 (for the data in FIGS. 5B and 5C). The ordinarily skilled artisan will understand that each specific concentration value in Tables 4 and 5 is subject to some minor experimental variability, so that each specific concentration given indicates a value of about the indicated concentration (e.g., a concentration indicated in a table as 0.1 nM represents a value of about 0.1 nM).

TABLE 4

| Conc, Log (Molar) | Conc, nM |
|---|---|
| −5.70 | 2000.00 |
| −6.18 | 666.67 |
| −6.65 | 222.22 |
| −7.13 | 74.07 |
| −7.61 | 24.69 |
| −8.21 | 6.17 |
| −8.81 | 1.54 |

TABLE 4-continued

| Conc, Log (Molar) | Conc, nM |
|---|---|
| −9.41 | 0.39 |
| −10.02 | 0.10 |

TABLE 5

| Conc, Log(Molar) | Conc, nM |
|---|---|
| −5.69897 | 2000.00 |
| −6.176091 | 666.67 |
| −6.653213 | 222.22 |
| −7.130334 | 74.07 |
| −7.607455 | 24.69 |
| −8.209515 | 6.17 |
| −8.811575 | 1.54 |
| −9.413635 | 0.39 |
| −10.01569 | 0.10 |
| −10.61775 | 0.02 |

It is noted that the concentrations shown in Table 5 are total concentrations for the pairs of antibodies used. The ratio used is 1:1 so each individual antibody in the pair comprises half of the total concentration.

Figure 6A:
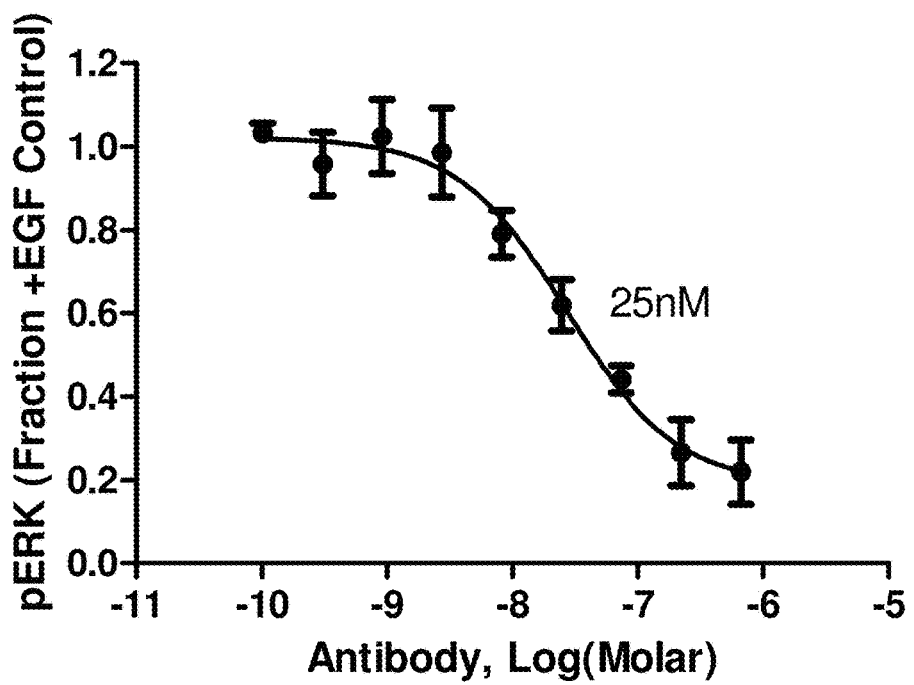
FIG. 6A is a graph showing the results of a phospho-ERK (pERK) ELISA, demonstrating pERK inhibition by P1X antibody, with an $IC_{50}$ value of approximately 25 nM.

Example 6: Phospho-ERK Signaling Inhibition by Different Combination Ratios of P1X, P2X, and P3X A431 cells were treated with a dilution series of P1X and phospho-ERK inhibition measured by ELISA (FIG. 6A). The concentrations used in the dilution series for the antibodies are shown below in Table 6. The ordinarily skilled artisan will understand that each specific concentration value in Table 6 is subject to some minor experimental variability, so that each specific concentration given indicates a value of about the indicated concentration (e.g., a concentration indicated in a table as 0.1 nM represents a value of about 0.1 nM).

TABLE 6

| Conc, Log(Molar) | Conc, nM |
|---|---|
| −5.69897 | 2000.00 |
| −6.176091 | 666.67 |
| −6.653213 | 222.22 |
| −7.130334 | 74.07 |
| −7.607455 | 24.69 |
| −8.084577 | 8.23 |
| −8.561698 | 2.74 |
| −9.038818 | 0.91 |
| −9.51594 | 0.30 |
| −9.993061 | 0.10 |

The experiment was carried out as described in the methodology section. Under these experimental conditions, P1X inhibits 81% of phospho-ERK activity at saturating doses with an IC50 value of about 25 nM (27 nM). Therefore the approximate location on the plot of the IC50 is indicated in FIG. 6A by "25 nM" and 25 nM was set as the constant concentration of P1X in the following experiments.

Figure 6B:
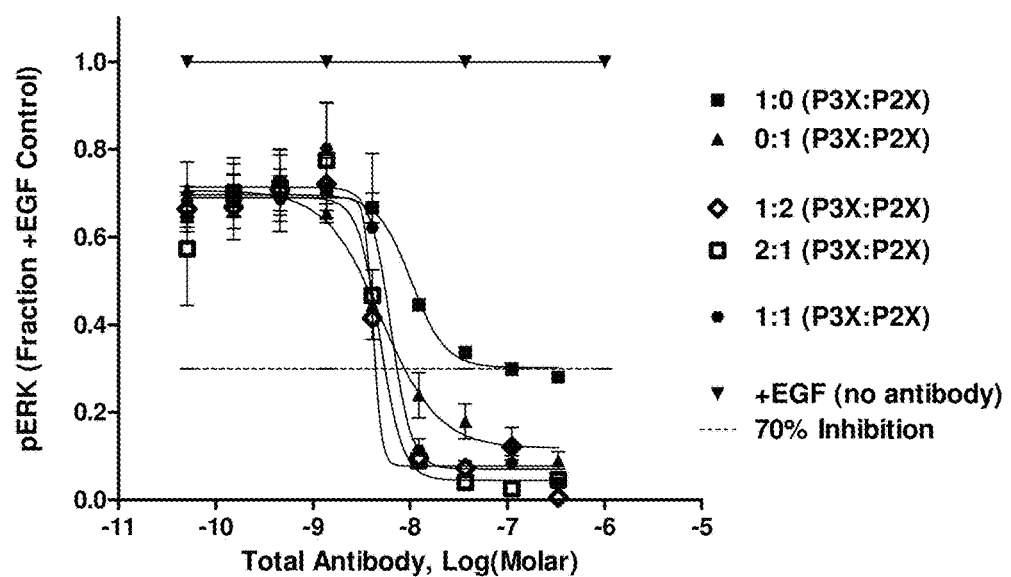
FIG. 6B is a graph showing the results of a phospho-ERK (pERK) ELISA for A431 cells treated with a dilution series of 5 combination ratios of P3X+P2X in combination with a constant P1X concentration of 25 nM.

A431 cells were treated with dilution series of 5 combination ratios of P3X+P2X in combination with a constant P1X concentration of 25 nM and phospho-ERK inhibition measured by ELISA (FIG. 6B). The concentrations used in the dilution series for the antibodies are shown below in Table 7. The ordinarily skilled artisan will understand that each specific concentration value in Table 7 is subject to some minor experimental variability, so that each specific concentration given indicates a value of about the indicated concentration (e.g., a concentration indicated in a table as 0.1 nM represents a value of about 0.1 nM).

TABLE 7

| Conc, Log(Molar) | Conc, nM |
|---|---|
| −5.69897 | 2000.00 |
| −6.176091 | 666.67 |
| −6.653213 | 222.22 |
| −7.130334 | 74.07 |
| −7.607455 | 24.69 |
| −8.084577 | 8.23 |
| −8.561698 | 2.74 |
| −9.038818 | 0.91 |
| −9.51594 | 0.30 |
| −9.993061 | 0.10 |

It is noted that the concentrations shown in Table 7 are total concentrations for P2X+P3X. The individual concentration of P2X and P3X is dependent on the indicated ratio. The experiment was carried out as described in the methodology section. The ratios of P3X:P2X used were 1:0, 0:1, 1:2, 2:1, and 1:1. All ratios inhibited greater than 70% of phospho-ERK activity, with those combinations containing all three antibodies providing the highest degree of inhibition.

Figure 6C:
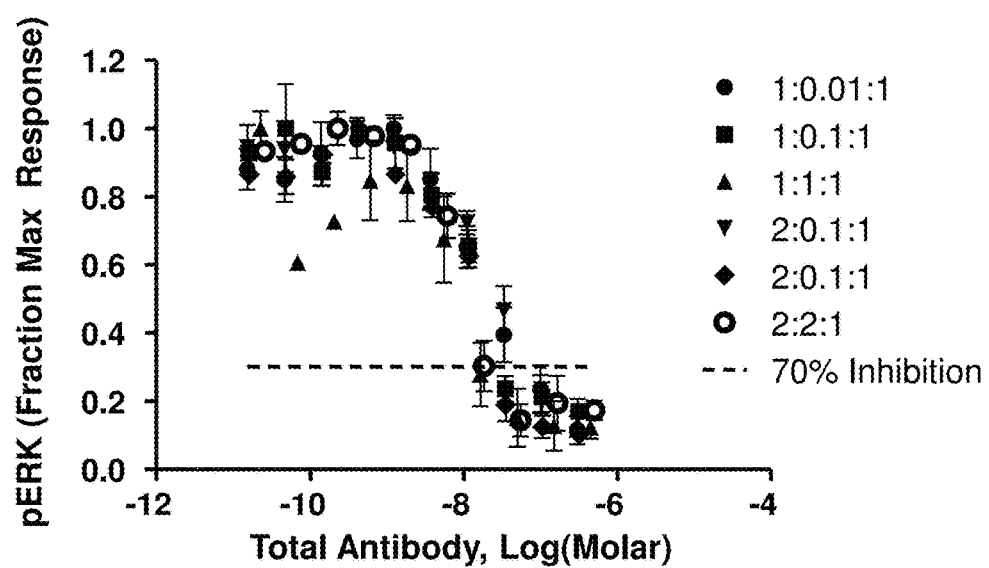
FIG. 6C is a graph showing the results of a phospho-ERK (pERK) ELISA for A431 cells treated with a dilution series of 6 combination ratios of P1X:P2X:P3X.

A431 cells were treated with dilution series of 6 combination ratios of P1X:P2X:P3X and phospho-ERK inhibition measured by ELISA (FIG. 6C). The concentrations used in the dilution series for the antibodies are shown below in Table 8. The ordinarily skilled artisan will understand that each specific concentration value in Table 8 is subject to some minor experimental variability, so that each specific concentration given indicates a value of about the indicated concentration (e.g., a concentration indicated in a table as 0.1 nM represents a value of about 0.1 nM).

TABLE 8

| | | Ratio (P1X:P2X:P3X) | | | | | |
|---|---|---|---|---|---|---|---|
| LogM | nM | 1:0.01:1 | 1:0.1:1 | 1:1:1 | 2:0.1:1 | 2:0.1:1 | 2:2:1 |
| −10.8148 | 0.0153 | X | | | | | |
| −10.8141 | 0.0153 | | | | X | | |
| −10.7958 | 0.0160 | | X | | | | |
| −10.7889 | 0.0163 | | | | | X | |
| −10.6409 | 0.0229 | | | X | | | |
| −10.5951 | 0.0254 | | | | | | X |
| −10.3377 | 0.0460 | X | | | | | |
| −10.3370 | 0.0460 | | | | X | | |
| −10.3187 | 0.0480 | | X | | | | |
| −10.3118 | 0.0488 | | | | | X | |
| −10.1638 | 0.0686 | | | X | | | |
| −10.1180 | 0.0762 | | | | | | X |
| −9.8606 | 0.1379 | X | | | | | |
| −9.8598 | 0.1381 | | | | X | | |
| −9.8415 | 0.1440 | | X | | | | |
| −9.8347 | 0.1463 | | | | | X | |
| −9.6866 | 0.2058 | | | X | | | |
| −9.6409 | 0.2286 | | | | | | X |
| −9.3834 | 0.4136 | X | | | | | |
| −9.3827 | 0.4143 | | | | X | | |
| −9.3644 | 0.4321 | | X | | | | |
| −9.3576 | 0.4390 | | | | | X | |
| −9.2095 | 0.6173 | | | X | | | |
| −9.1638 | 0.6859 | | | | | | X |
| −8.9063 | 1.2407 | X | | | | | |
| −8.9056 | 1.2428 | | | | X | | |
| −8.8873 | 1.2963 | | X | | | | |
| −8.8805 | 1.3169 | | | | | X | |
| −8.7324 | 1.8519 | | | X | | | |

TABLE 8-continued

| LogM | nM | 1:0.01:1 | 1:0.1:1 | 1:1:1 | 2:0.01:1 | 2:0.1:1 | 2:2:1 |
|---|---|---|---|---|---|---|---|
| −8.6866 | 2.0576 | | | | | | X |
| −8.4292 | 3.7222 | X | | | | | |
| −8.4285 | 3.7284 | | | | X | | |
| −8.4102 | 3.8889 | | X | | | | |
| −8.4033 | 3.9506 | | | | | X | |
| −8.2553 | 5.5555 | | | X | | | |
| −8.2095 | 6.1728 | | | | | | X |
| −7.9521 | 11.1667 | X | | | | | |
| −7.9514 | 11.1852 | | | | X | | |
| −7.9331 | 11.6667 | | X | | | | |
| −7.9262 | 11.8518 | | | | | X | |
| −7.7782 | 16.6667 | | | X | | | |
| −7.7324 | 18.5185 | | | | | | X |
| −7.4750 | 33.5000 | X | | | | | |
| −7.4742 | 33.5555 | | | | X | | |
| −7.4559 | 35.0000 | | X | | | | |
| −7.4491 | 35.5556 | | | | | X | |
| −7.3010 | 50.0000 | | | X | | | |
| −7.2553 | 55.5556 | | | | | | X |
| −6.9978 | 100.5000 | X | | | | | |
| −6.9971 | 100.6667 | | | | X | | |
| −6.9788 | 104.9999 | | X | | | | |
| −6.9720 | 106.6665 | | | | | X | |
| −6.8239 | 149.9999 | | | X | | | |
| −6.7782 | 166.6668 | | | | | | X |
| −6.5207 | 301.4998 | X | | | | | |
| −6.5200 | 302.0000 | | | | X | | |
| −6.5017 | 315.0003 | | X | | | | |
| −6.4949 | 320.0000 | | | | | X | |
| −6.3468 | 450.0005 | | | X | | | |
| −6.3010 | 500.0000 | | | | | | X |

The experiment was carried out as described in the methodology section. The ratios of P1X:P2X:P3X used were 1:0.01:1, 1:0.1:1, 1:1:1, 2:0.01:1, 2:0.1:1, and 2:2:1. All ratios inhibited greater than 70% of phospho-ERK activity.

Figure 6D:
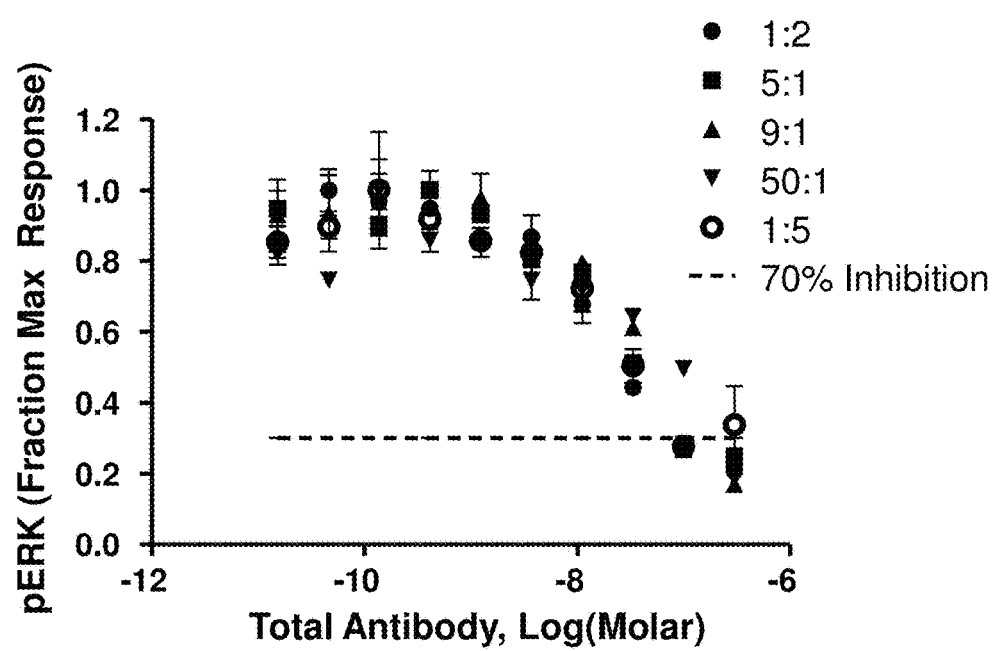
FIG. 6D is a graph showing the results of a phospho-ERK (pERK) ELISA for A431 cells treated with a dilution series of 5 combination ratios of P1X:P2X.

A431 cells were treated with dilution series of 5 combination ratios of P1X:P2X and phospho-ERK inhibition measured by ELISA (FIG. 6D). The concentrations used in the dilution series for the antibodies are shown below in Table 9. The ordinarily skilled artisan will understand that each specific concentration value in Table 9 is subject to some minor experimental variability, so that each specific concentration given indicates a value of about the indicated concentration (e.g., a concentration indicated in a table as 0.1 nM represents a value of about 0.1 nM).

TABLE 9

| Conc, Log(Molar) | Conc, nM |
|---|---|
| −6.522879 | 300.00 |
| −7 | 100.00 |
| −7.477121 | 33.33 |
| −7.954243 | 11.11 |
| −8.431364 | 3.70 |
| −8.908485 | 1.23 |
| −9.385606 | 0.41 |
| −9.862727 | 0.14 |
| −10.33985 | 0.05 |
| −10.81697 | 0.02 |

It is noted that the concentrations shown in Table 9 are total concentrations for P1X+P2X. The individual concentration of P1X and P2X is dependent on the indicated ratio. The experiment was carried out as described in the methodology section. The ratios of P1X:P2X used were 1:2, 5:1, 9:1, 50:1, and 1:5. All ratios except 1:5 (P1X:P2X) inhibited greater than 70% of phospho-ERK activity within the concentration range used in the experiment. However, fitting a 4 parameter logistic inhibition curve to the 1:5 ratio (P1X:P2X) data predicts that this combination will achieve 70% phospho-ERK inhibition at a concentration of 35.7 nM, marginally higher than the dose used in the experiment and well within the range achievable under physiological conditions.

Figure 7A:
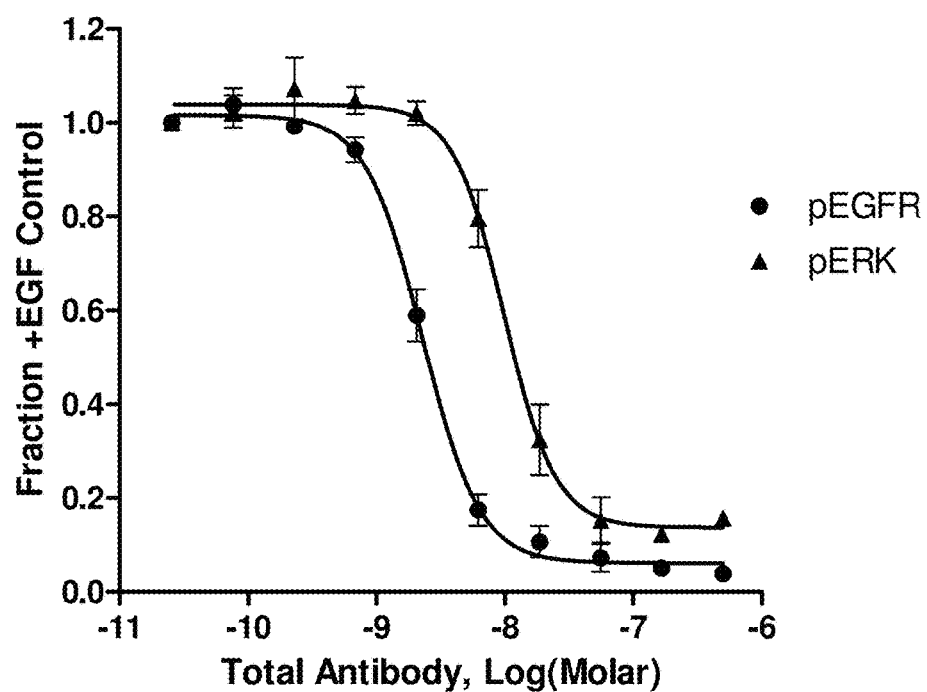
FIG. 7A is a graph showing the results of a phospho-EGFR (pEGFR) ELISA (circles) and a phospho-ERK (pERK) ELISA (triangles), demonstrating inhibition by a 2:2:1 combination of P1X:P2X:P3X.

Example 7: Phospho-EGFR and Phospho-ERK Signaling Inhibition by a 2:2:1 Ratio Combination of P1X, P2X, and P3X A431 cells were treated with a dilution series of a 2:2:1 molar ratio combination of antibodies P1X, P2X, and P3X (this combination at this molar ratio is referred to herein as "P1X+P2X+P3X") and phospho-EGFR and phospho-ERK inhibition measured by ELISA (FIG. 7A). The concentrations used in the dilution series for the antibodies are shown below in Table 10. The ordinarily skilled artisan will understand that each specific concentration value in Table 10 is subject to some minor experimental variability, so that each specific concentration given indicates a value of about the indicated concentration (e.g., a concentration indicated in a table as 0.1 nM represents a value of about 0.1 nM).

TABLE 10

| Conc, Log(Molar) | Conc, nM |
|---|---|
| −6.30 | 500.00 |
| −6.78 | 166.67 |
| −7.26 | 55.56 |
| −7.73 | 18.52 |
| −8.21 | 6.17 |
| −8.69 | 2.06 |
| −9.16 | 0.69 |
| −9.64 | 0.23 |
| −10.12 | 0.08 |
| −10.60 | 0.03 |

It is noted that the concentrations shown in Table 10 are total concentrations for P1X+P2X+P3X. The ratio used is 2:2:1, so the individual concentrations of P1X, P2X and P3X are 40%, 40% and 20%, respectively. Experiments were carried out as described in the methodology section. The combination of three antibodies is a potent inhibitor of both phospho-EGFR and phospho-ERK activities, with respective IC50 values of 2.30 nM and 9.87 nM.

Figure 7B:
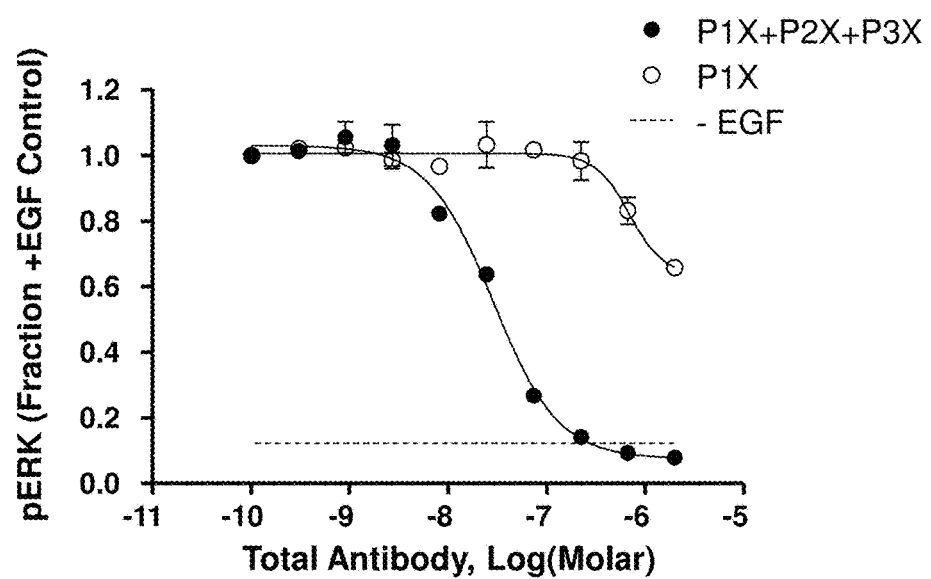
FIG. 7B is a graph showing the results of a phospho-ERK (pERK) ELISA, demonstrating inhibition by a 2:2:1 formulation of P1X:P2X:P3X (P1X+P2X+P3X) versus P1X single antibody alone.
Figure 7C:
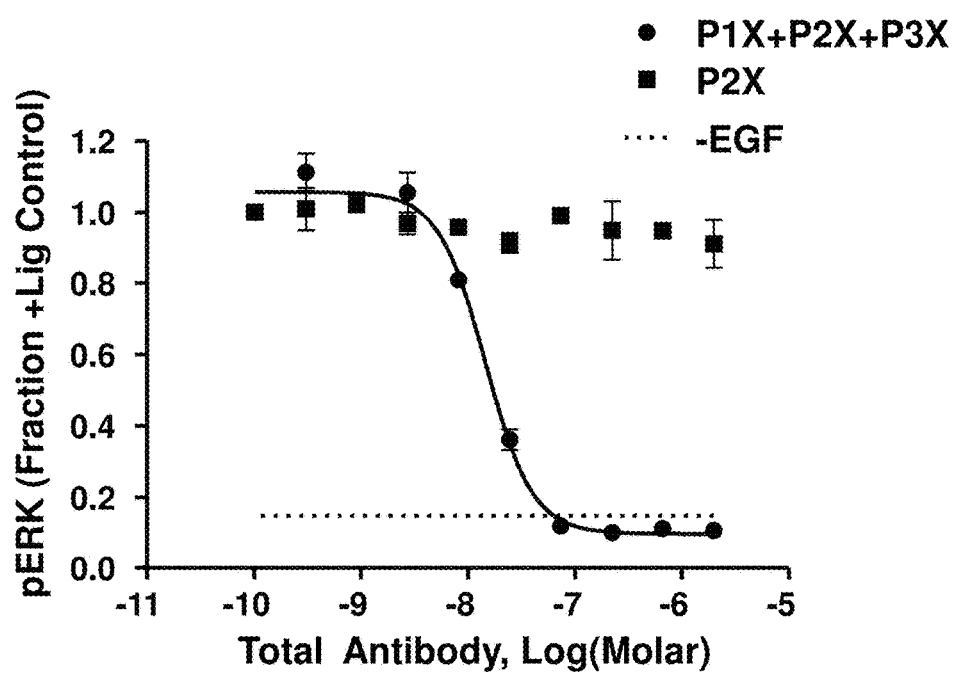
FIG. 7C is a graph showing the results of a phospho-ERK (pERK) ELISA, demonstrating inhibition by P1X+P2X+P3X versus P2X single antibody alone.

P1X+P2X+P3X was compared to P1X single (FIG. 7B) and P2X single (FIG. 7C). A431 cells were treated with a dilution series of antibody and phospho-ERK inhibition measured by ELISA. The concentrations used in the dilution series for the antibodies for the experiments shown in FIGS. 7B and 7C are shown below in Table 11. The ordinarily skilled artisan will understand that each specific concentration value in Table 11 is subject to some minor experimental variability, so that each specific concentration given indicates a value of about the indicated concentration (e.g., a concentration indicated in a table as 0.1 nM represents a value of about 0.1 nM).

TABLE 11

| Conc, Log(Molar) | Conc, nM |
|---|---|
| −5.69897 | 2000.00 |
| −6.176091 | 666.67 |
| −6.653213 | 222.22 |
| −7.130334 | 74.07 |

TABLE 11-continued

| Conc, Log(Molar) | Conc, nM |
| --- | --- |
| −7.607455 | 24.69 |
| −8.084577 | 8.23 |
| −8.561698 | 2.74 |
| −9.038818 | 0.91 |
| −9.51594 | 0.30 |
| −9.993061 | 0.10 |

It is noted that the concentrations shown in Table 11 are total concentrations for P1X+P2X+P3X. The ratio used is 2:2:1, so the individual concentrations of P1X, P2X and P3X are 40%, 40% and 20%, respectively. Experiments were carried out as described in the methodology section with the exception that 80 nM of EGF ligand was used to stimulate cells. The 2:2:1 ratio combination of antibodies is a potent inhibitor of phospho-ERK activity compared to P1X and P2X, which respectively provide partial and no inhibition.

Figure 8A:
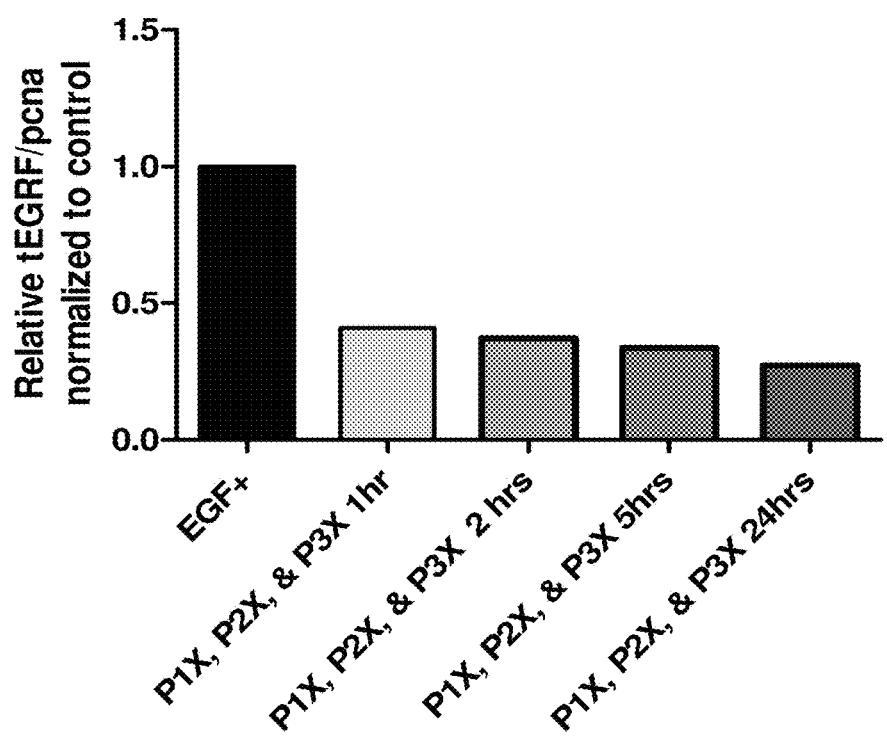
FIG. 8A is a bar graph showing western blot analysis results for total EGFR (tEGFR) internalization kinetics of H1975 cells pre-treated with P1X+P2X+P3X antibodies for various periods of time before stimulation with EGF.
Figure 8B:
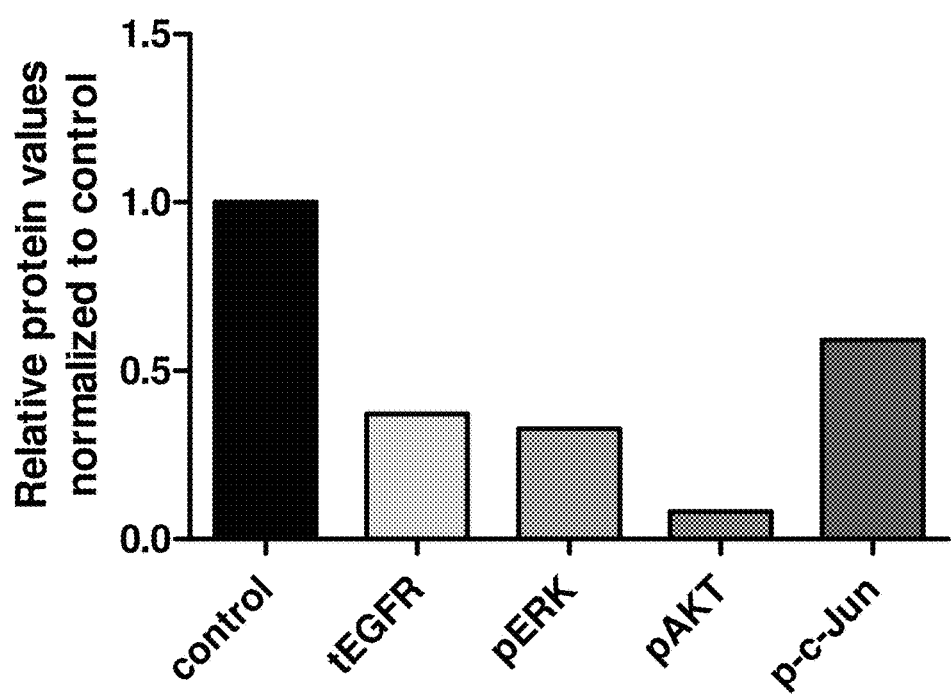
FIG. 8B is a bar graph showing western blot analysis results for H1975 cells pre-treated with P1X+P2X+P3X antibodies before stimulation with EGF, showing levels of tEGFR, pERK, phospho-AKT (pAKT) and phospho-c-Jun (p-c-Jun) in the cells, normalized to the loading control (PCNA) and to lysates of control untreated cells.

Example 8: EGF Receptor Down-Regulation and Inhibition of pERK, pAKT and p-c-Jun Signaling in H1975 Cells Following Treatment with P1X+P2X+P3X Cells were pre-incubated for 2 hours with of P1X+P2X+P3X equaling 1 µM total antibody prior to stimulation with 50 ng/ml rhEGF (PeproTech) for 10 minutes, as described in the methodology section above. Immunoblots of cell lysates were separately probed with antibodies against tEGFR, pERK, pAKT or p-c-Jun and densitometry of the bands was normalized to the loading control PCNA and to lysates of control untreated cells. EGF receptor down-regulation in response to P1X+P2X+P3X treatment is shown in FIG. 8A and inhibition of pERK, pAKT and p-c-Jun signaling in response to P1X+P2X+P3X treatment is shown in FIG. 8B.

Example 9: Inhibition of Tumor Cell Proliferation In Vitro

Figure 9A:
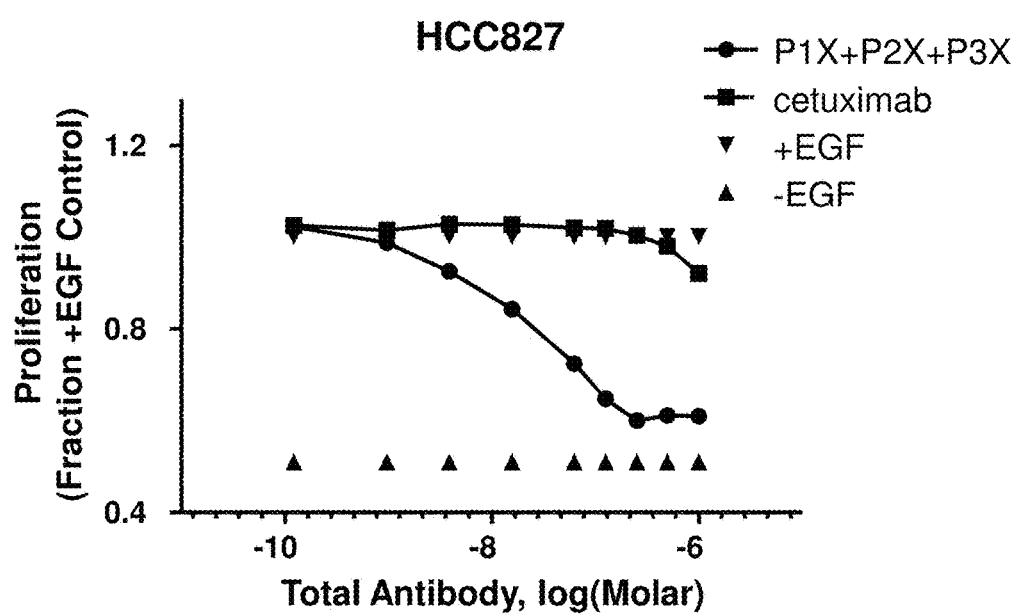
FIG. 9A is a graph showing the results of a cell viability assay for HCC827 cells, demonstrating inhibition of tumor cell proliferation by treatment with P1X+P2X+P3X antibodies, as compared to cetuximab, in the presence of EGF ligand.
Figure 9B:
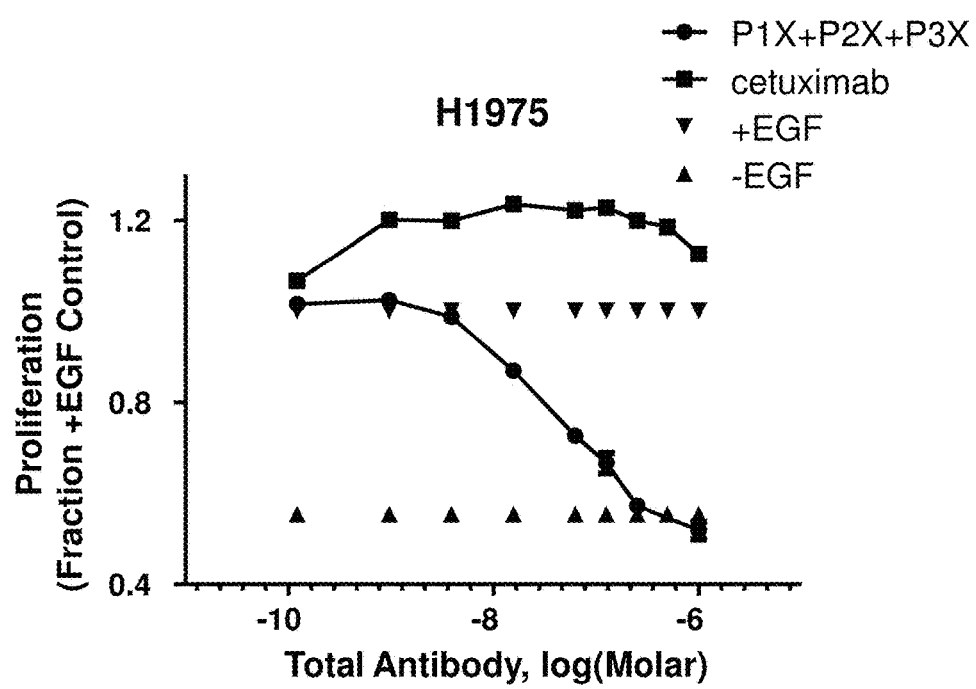
FIG. 9B is a graph showing the results of a cell viability assay for H1975 cells, demonstrating inhibition of tumor cell proliferation by treatment with P1X+P2X+P3X antibodies, as compared to cetuximab, in the presence of EGF ligand.
Figure 9C:
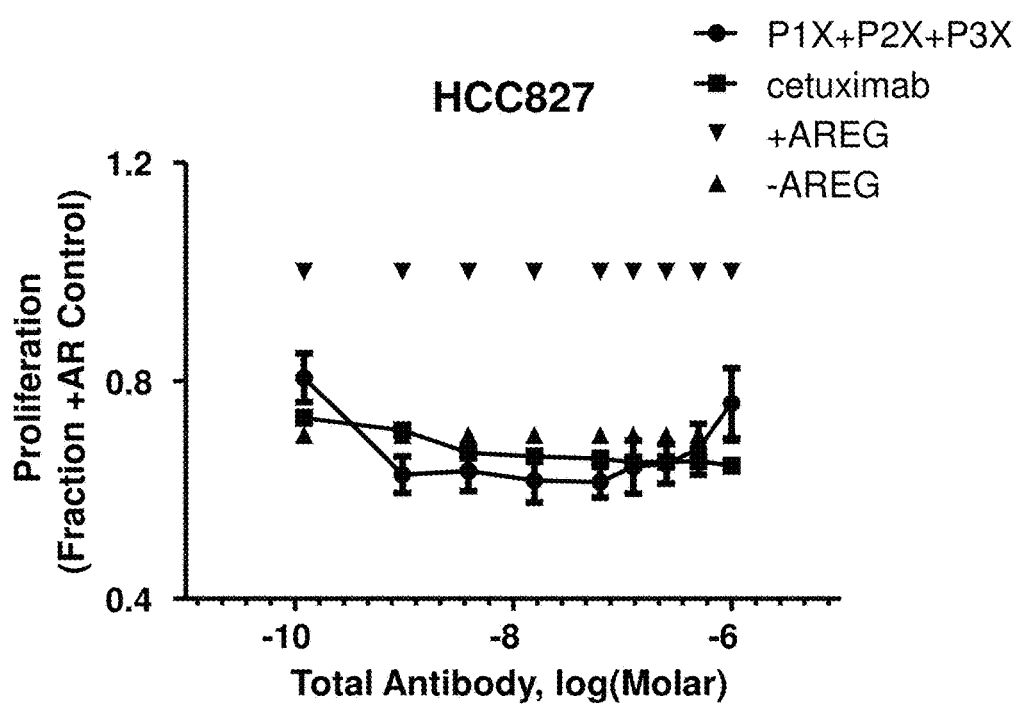
FIG. 9C is a graph showing the results of a cell viability assay for HCC827 cells, demonstrating inhibition of tumor cell proliferation by treatment with P1X+P2X+P3X antibodies, as compared to cetuximab, in the presence of amphiregulin (AREG) ligand.
Figure 9D:
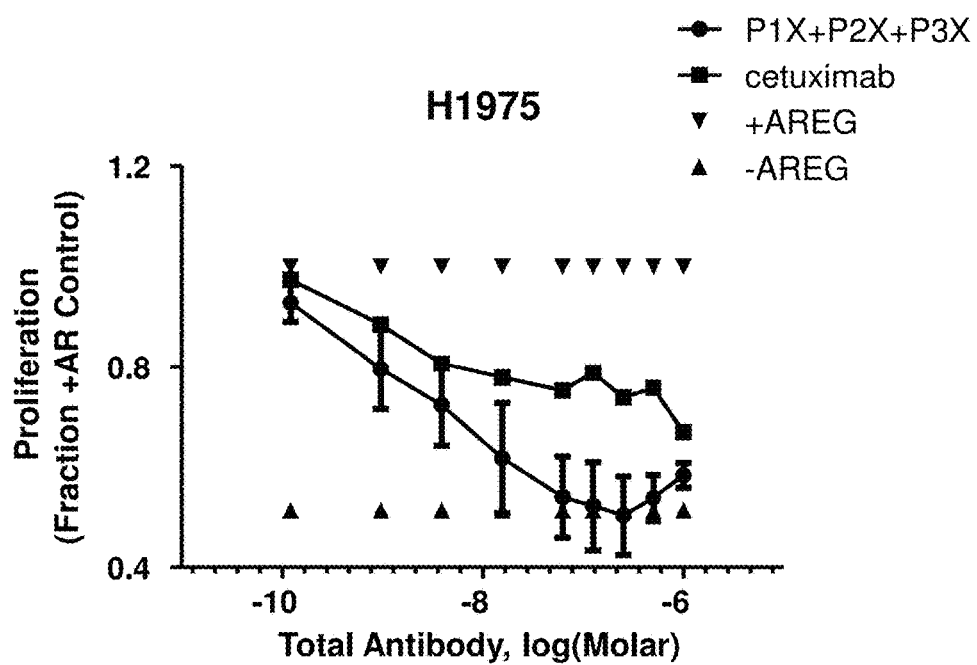
FIG. 9D is a graph showing the results of a cell viability assay for H1975 cells, demonstrating inhibition of tumor cell proliferation by treatment with P1X+P2X+P3X antibodies, as compared to cetuximab, in the presence of AREG ligand.

Inhibition of tumor cell proliferation in vitro was analyzed by the methods described above or minor variations thereof. The non-small cell lung cancer (NSCLC) lines HCC827 and H1975 were plated at 5000 cells/well and treated with antibody combinations ranging from 0.1-1 µM (final concentration). FIGS. 9A-9D show inhibition of cell proliferation using CellTiter-Glo® (CTG) Luminescent Cell Viability Assay (Promega Corporation) that measures the number of viable cells in culture based upon quantitation of ATP present, which is an indicator of metabolically active cells. FIGS. 9A and 9B show potent inhibition of growth of HCC827 and H1975 cells over a range of P1X+P2X+P3X concentrations, but not by cetuximab treatment or assay medium alone (1% FCS) in the presence of EGF ligand. FIGS. 9C and 9D show potent inhibition of growth of HCC827 and H1975 cells over a range of concentrations for both P1X+P2X+P3X and cetuximab, but not by assay medium alone (1% FCS) in the presence of AREG ligand. These results demonstrate the ability of P1X+P2X+P3X to inhibit tumor cell proliferation in vitro in response to both high-affinity (EGF) and low-affinity (AREG) ligands, whereas cetuximab is only effective in cells treated with low-affinity (AREG) ligand. The concentrations used in the dilution series for the antibodies for the experiments shown in FIGS. 9A-D are shown below in Table 12. The ordinarily skilled artisan will understand that each specific concentration value in Table 12 is subject to some minor experimental variability, so that each specific concentration given indicates a value of about the indicated concentration (e.g., a concentration indicated in a table as 0.1 nM represents a value of about 0.1 nM).

TABLE 12

| Conc, Log(Molar) | Conc, nM |
| --- | --- |
| −6.000000 | 1000.00 |
| −6.301030 | 500.00 |
| −6.602060 | 250.00 |
| −6.903090 | 125.00 |
| −7.204120 | 62.50 |
| −7.806180 | 15.63 |
| −8.408240 | 3.91 |
| −9.010300 | 0.98 |
| −9.913390 | 0.12 |

It is noted that the concentrations shown in Table 12 are total concentrations for P1X+P2X+P3X. The ratio used is 2:2:1, so the individual concentrations of P1X, P2X and P3X are 40%, 40% and 20%, respectively.

Example 10: Inhibition of Tumor Growth In Vivo

Efficacy of P1X+P2X+P3X in vivo was assessed in a H1975 lung cancer cell xenograft murine mouse model. $2 \times 10^6$ NCI-H1975 cells were injected subcutaneously into the flank of nu/nu mice. Once tumors had reached an average size of 300 mm$^3$ treatment was initiated. Groups of 10 mice were treated with either vehicle control (PBS); or the murine ratio antibody trio at the following component concentrations: murine ratio antibody trio-Low P1X=2.53 mg/kg, P2X=7.26 mg/kg and P3X=0.66 mg/kg or murine ratio antibody trio-Medium P1X=5.06 mg/kg, P2X=14.52 mg/kg and P3X=1.33 mg/kg. Mice were treated every two days.

Figure 10A:
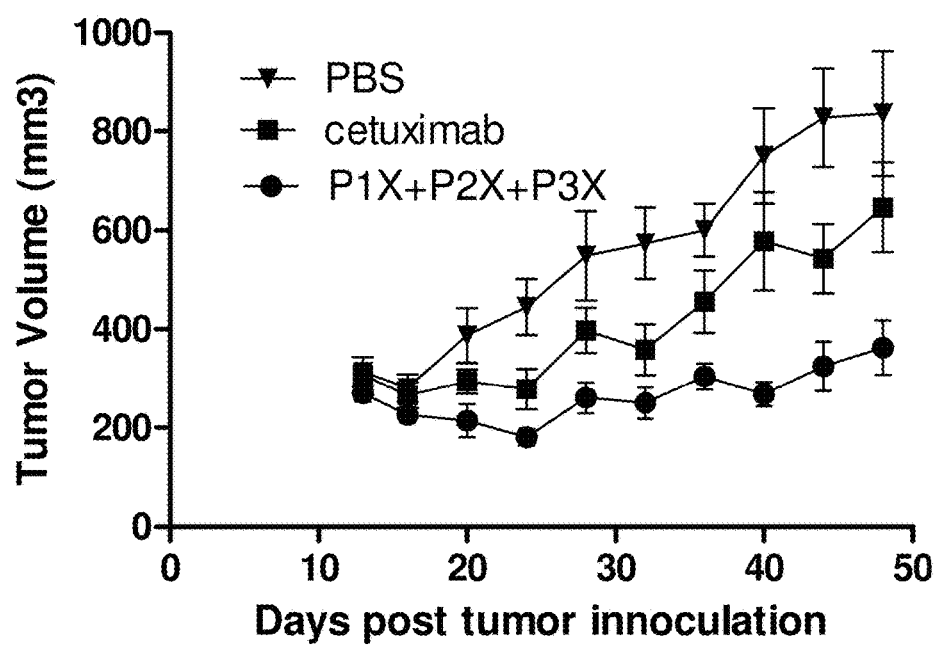
FIG. 10A is a graph showing the results of a DU145 tumor xenograft mouse model experiment, demonstrating decreased tumor volume in vivo in mice treated with P1X+P2X+P3X antibodies, as compared to PBS and cetuximab controls.
Figure 10B:
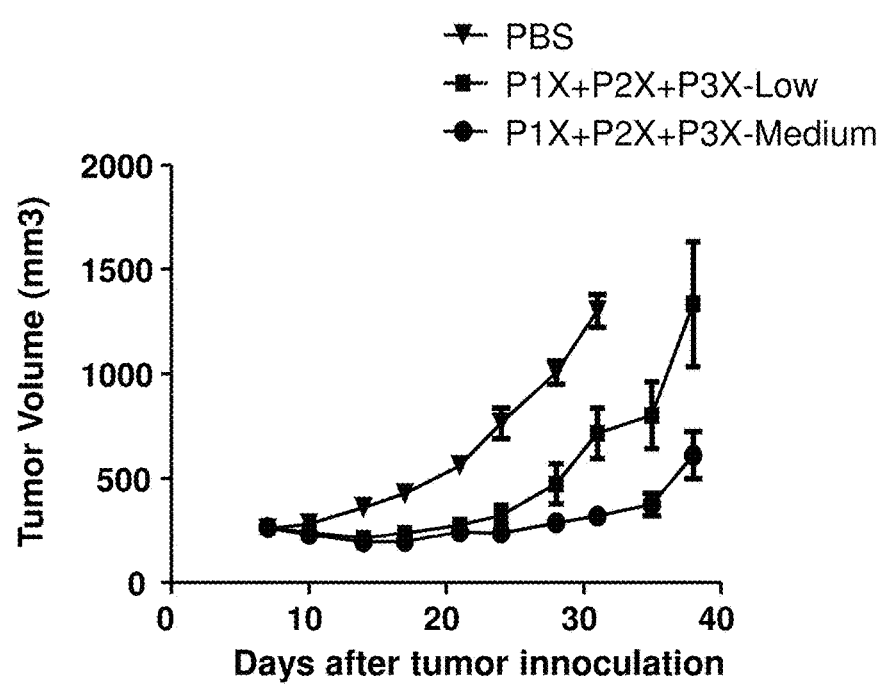
FIG. 10B is a graph showing the results of an H1975 tumor xenograft mouse model experiment, demonstrating decreased tumor volume in vivo in mice treated with P1X+P2X+P3X antibodies, as compared to PBS control.

The results shown in FIG. 10A (DU145 xenograft model) and FIG. 10B (H1975 xenograft model) demonstrate the ability of P1X+P2X+P3X to inhibit tumor growth (and, inferentially, cell proliferation) in vivo.

Example 11: Ligand Antagonism Cell Binding Assays with Single Antibodies

A cell binding assay was performed to demonstrate that monoclonal antibodies P1X, P2X, and P3X can antagonize the interaction of EGF ligand and EGF receptor on A431 cells. A431 cells were incubated with one dose of single antibody for 1 hr followed by a dilution series of biotin-EGF ligand and the amount of bound biotin-EGF ligand measured by quantitative flow cytometry, as described in the methods section above. The concentrations for the antibodies are shown below in Table 13 and represent a sub-saturating concentration (approx. EC90 concentration) of cell binding as determined from the analysis demonstrated in Example 3. The concentrations used in the dilution series for the biotin-EGF are shown below in Table 14. The values in Table 13 and Table 14 are subject to some minor experimental variability, so that each specific concentration given indicates a value of about the indicated concentration (e.g., a concentration indicated in a table as 0.1 nM represents a value of about 0.1 nM).

TABLE 13

| Antibody | Conc, Log(Molar) | Conc, nM |
|---|---|---|
| P1X | −9.01 | 0.97 |
| P2X | −8.70 | 2.00 |
| P3X | −8.33 | 4.68 |

TABLE 14

| Conc, Log(Molar) | Conc, nM |
|---|---|
| −6.70 | 200 |
| −7.18 | 66.67 |
| −7.65 | 22.22 |
| −8.13 | 7.41 |
| −8.61 | 2.47 |
| −9.08 | 0.82 |
| −9.56 | 0.27 |
| −10.04 | 0.09 |
| −10.52 | 0.03 |
| −11.00 | 0.01 |
| −11.52 | 0.003 |

Figure 11:
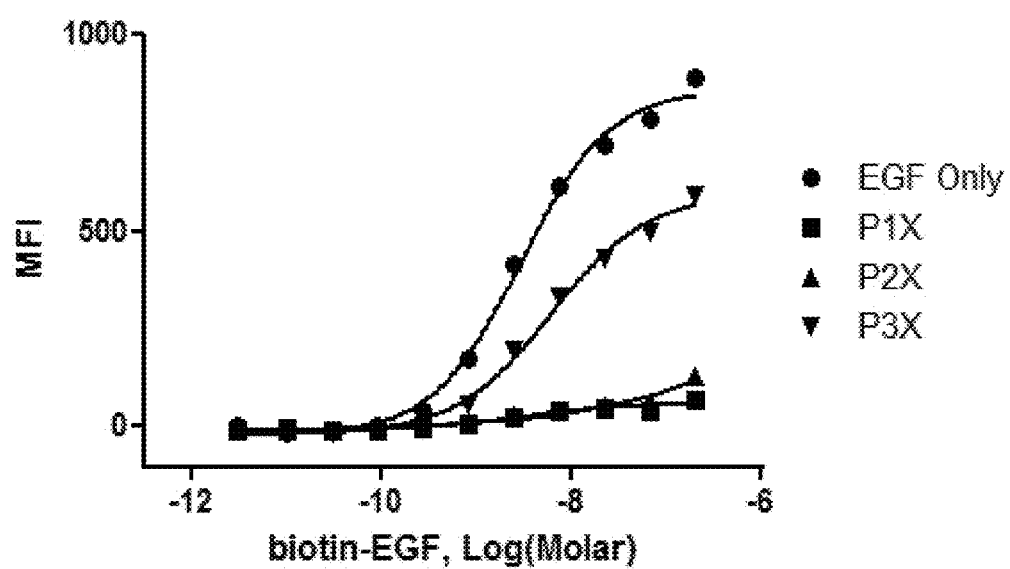
FIG. 11 is a graph showing the results of a ligand antagonism cell binding assay, demonstrating the EGF ligand blocking ability of P1X, P2X or P3X alone at low doses.

The results are shown in FIG. 11, which demonstrates that each of the single antibodies (P1X, P2X and P3X) alone are capable of antagonizing the interaction of EGF ligand and EGF receptor on A431 cells, with P1X and P2X exhibiting more potent inhibitory activity than P3X.

Example 12: Ligand Antagonism Cell Binding Assays with Single and Combinations of Antibodies or Fabs A cell binding assay was performed to determine the extent to which single antibodies and multiple antibody combinations of monoclonal antibodies P1X, P2X, and P3X and single and multiple combinations of monovalent Fab fragments P1X Fab, P2X Fab, and P3X Fab can antagonize the interaction of EGF ligand and EGF receptor on A431 cells. A431 cells were incubated with one dose of antibody or Fab for 1 hr followed by a dilution series of biotin-EGF ligand and the amount of bound biotin-EGF ligand measured by quantitative flow cytometry, as described in the methodology section above. The concentration of antibodies and Fab was 10 nM. The combinations of three antibodies (P1X+P2X+P3X) and three antibodies (P1X Fab+P2X Fab+P3X Fab) were formulated in a ratio of 2:2:1 and were dosed at a total concentration of 10 nM. The concentrations used in the dilution series for the biotin-EGF are shown above in Table 14. The ordinarily skilled artisan will understand that each specific concentration value in Table 14 is subject to some minor experimental variability, so that each specific concentration given indicates a value of about the indicated concentration (e.g., a concentration indicated in a table as 0.1 nM represents a value of about 0.1 nM).

Figure 12A:
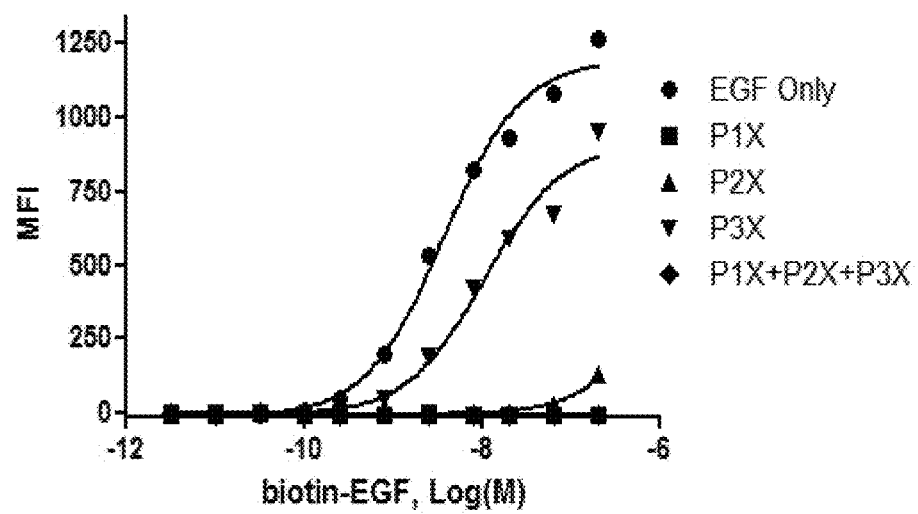
FIG. 12A is a graph showing the results of a ligand antagonism cell binding assay, demonstrating the EGF ligand blocking ability of P1X, P2X or P3X alone, or in triple combination, at high doses.
Figure 12B:
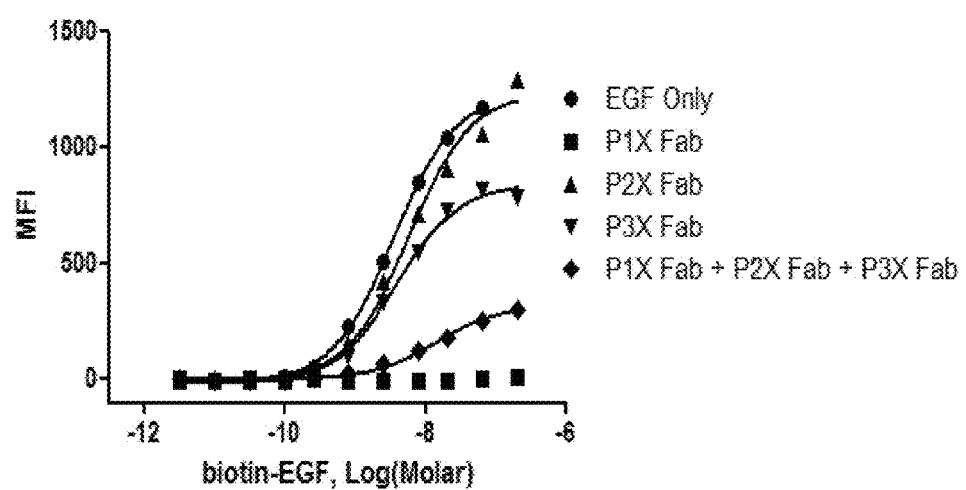
FIG. 12B is a graph showing the results of a ligand antagonism cell binding assay, demonstrating the EGF ligand blocking ability of P1X Fab, P2X Fab or P3X Fab alone, or in triple combination, at high doses.

The results are shown in FIG. 12A (single and combinations of monoclonal antibodies P1X, P2X, and P3X) and FIG. 12B (single and combinations of monovalent Fab fragments P1X Fab, P2X Fab, and P3X Fab). The results in FIG. 12A demonstrate that again all three antibodies alone were capable of antagonizing the interaction of EGF ligand and EGF receptor on A431 cells, with P1X and P2X exhibiting more potent inhibitory activity than P3X, and the triple combination of P1X+P2X+P3X also showed potent inhibitory activity. The results in FIG. 12B demonstrate that P1X Fab showed the strongest inhibitory activity alone, with P3X Fab alone showing intermediate inhibitory activity alone and P2X Fab showing only minimal inhibitory activity alone. The triple combination of P1X Fab+P2X Fab+P3X Fab also showed strong inhibitory activity, although less potent than P1X Fab alone.

Example 13: Phospho-EGFR and Phospho-ERK Signaling Inhibition by a 2:2:1 Molar Ratio Combination of P1X, P2X, and P3X Antibodies or Fabs A431 cells were treated with a dilution series of a 2:2:1 molar ratio combination of antibodies P1X, P2X, and P3X ("P1X+P2X+P3X") or Fabs P1X Fab, P2X Fab, P3X Fab (this combination at this molar ratio is referred to herein as "P1X Fab+P2X Fab+P3X Fab") and phospho-EGFR and phospho-ERK inhibition measured by ELISA. Experiments were performed with rhEGF (PeproTech) dosed at a concentration of 50 ng/mL or 500 ng/mL. The concentrations used in the dilution series for the antibodies and Fabs are shown below in Table 15. The ordinarily skilled artisan will understand that each specific concentration value in Table 15 is subject to some minor experimental variability, so that each specific concentration given indicates a value of about the indicated concentration (e.g., a concentration indicated in a table as 0.1 nM represents a value of about 0.1 nM).

TABLE 15

| Conc, Log(Molar) | Conc, nM |
|---|---|
| −5.70 | 2000.00 |
| −6.18 | 666.67 |
| −6.65 | 222.22 |
| −7.13 | 74.07 |
| −7.61 | 24.70 |
| −8.08 | 8.23 |
| −8.56 | 2.74 |
| −9.04 | 0.91 |
| −9.52 | 0.30 |
| −9.99 | 0.10 |

Figure 13A:
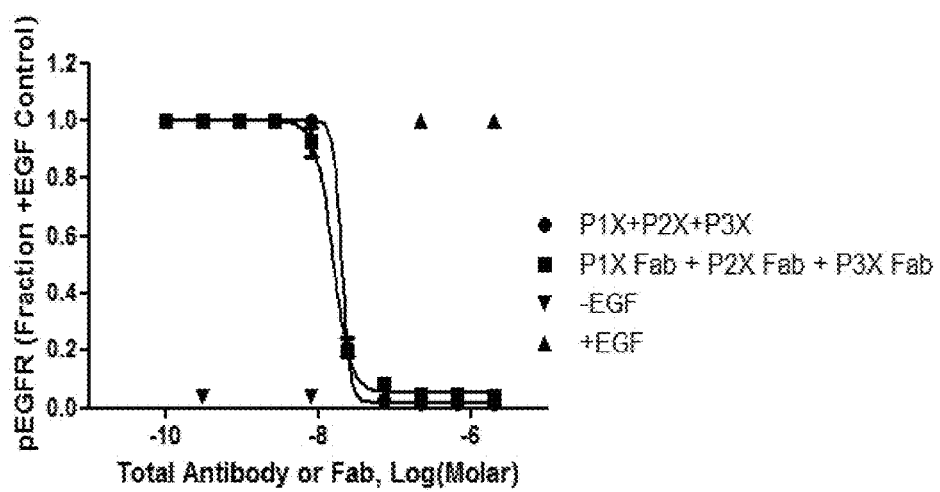
FIG. 13A is a graph showing the results of a phospho-EGFR inhibition assay, demonstrating the inhibitory ability of triple combinations of P1X+P2X+P3X or P1X Fab+P2X Fab+P3X Fab at low doses (50 ng/ml; 8 nM).
Figure 13B:
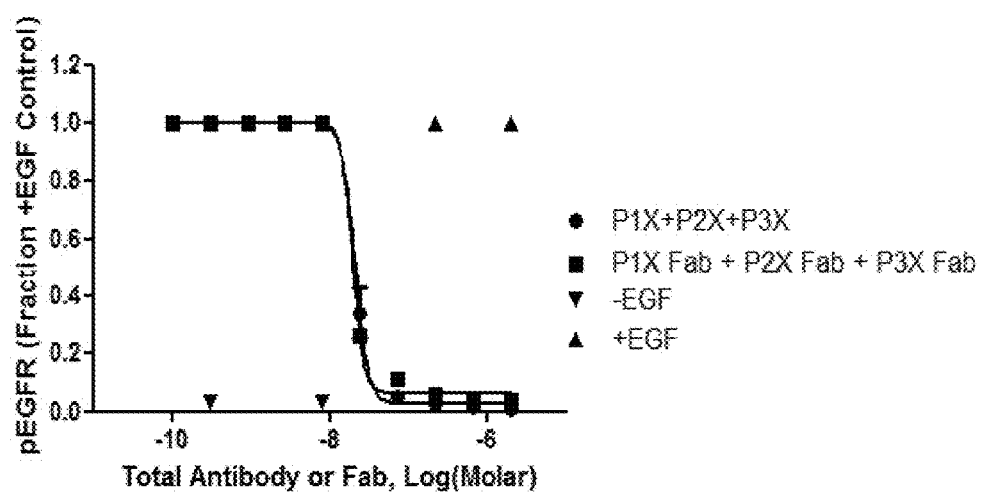
FIG. 13B is a graph showing the results of a phospho-EGFR inhibition assay, demonstrating the inhibitory ability of triple combinations of P1X+P2X+P3X or P1X Fab+P2X Fab+P3X Fab at high doses (500 ng/ml; 80 nM).
Figure 13C:
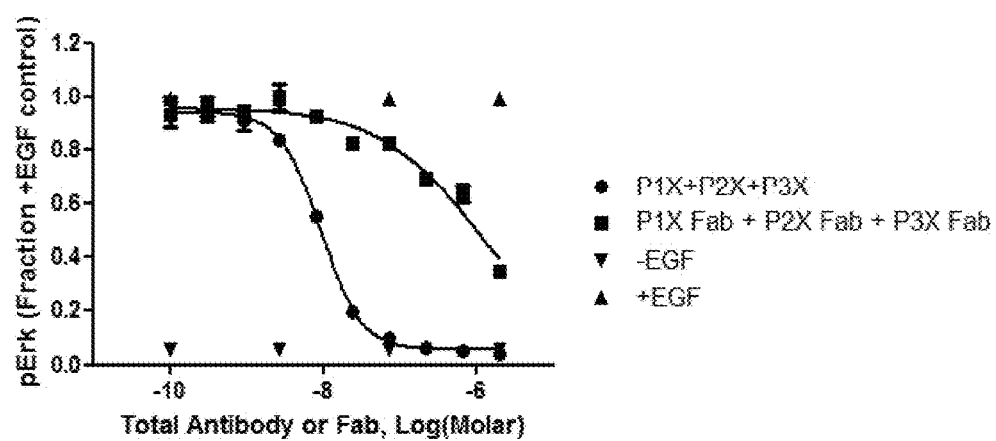
FIG. 13C is a graph showing the results of a phospho-ERK inhibition assay, demonstrating the inhibitory ability of triple combinations of P1X+P2X+P3X or P1X Fab+P2X Fab+P3X Fab at low doses (50 ng/ml; 8 nM).
Figure 13D:
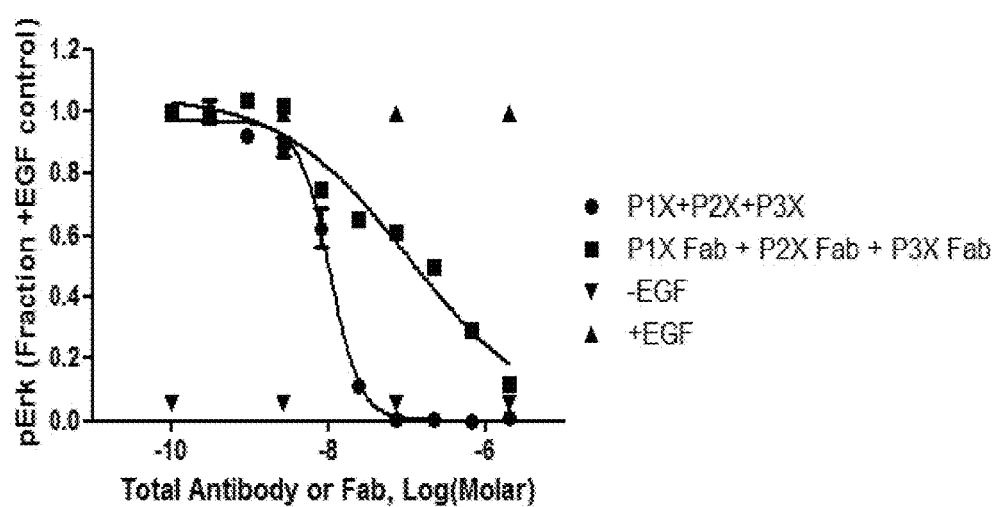
FIG. 13D is a graph showing the results of a phospho-ERK inhibition assay, demonstrating the inhibitory ability of triple combinations of P1X+P2X+P3X or P1X Fab+P2X Fab+P3X Fab at high doses (500 ng/ml; 80 nM).

The results are shown in FIGS. 13A-D, wherein FIGS. 13A and 13B show the results of the phospho-EGFR inhibition assay and FIGS. 13C and 13D show the results of the phosphor-ERK inhibition assay, with FIGS. 13A and 13C showing the results at low doses (50 ng/ml or 8 nM) and with FIGS. 13B and 13D showing the results at high doses (500 ng/ml or 80 nM).

With respect to inhibition of phospho-EGFR, the results in FIGS. 13A and 13B demonstrate that both triple combinations, P1X+P2X+P3X mAbs and P1X Fab+P2X Fab+P3X Fab fragments, exhibited strong inhibition at both the low dose and the high dose tested.

With respect to inhibition of phospho-ERK, the results in FIGS. 13C and 13D demonstrate that both triple combinations, P1X+P2X+P3X mAbs and P1X Fab+P2X Fab+P3X Fab fragments, exhibited inhibition at both the low dose and the high dose tested, with the P1X+P2X+P3X mAb combination exhibiting more potent inhibition that the P1X Fab+P2X Fab+P3X Fab fragment combination.

Figure 14:
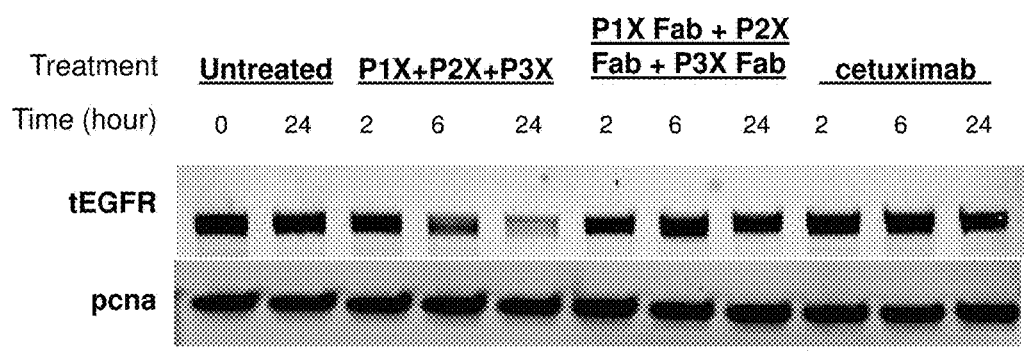
FIG. 14 is an immunoblot of an EGF-receptor downregulation assay in cells pre-treated with triple combinations of P1X+P2X+P3X or P1X Fab+P2X Fab+P3X Fab or with cetuximab. The housekeeping protein pcna was used as a control.

Example 14: EGF Receptor Down-Regulation in DU-145 Cells Following Treatment with P1X+P2X+P3X, P1X Fab+P2X Fab+P3X Fab, or Cetuximab Cells were pre-incubated for 2, 6, or 24 hours with of P1X+P2X+P3X, P1X Fab+P2X Fab+P3X Fab, or cetuximab equaling 50 nM, 100 nM, and 50 nM, respectively. The Fab combination is dosed at twice the concentration as P1X+P2X+P3X and cetuximab to account for a single binding moiety on a Fab molecule versus two binding moieties on and IgG molecule. Immunoblots of cell lysates were probed with antibodies against total EGFR (tEGFR) and the pcna housekeeping protein as a control, as described in the methodology section above. EGF receptor downregulation in response to treatment is shown in FIG. 14. The results demonstrate that treatment with P1X+P2X+P3X led to observable down-regulation of EGFR, in a time dependent manner, whereas treatment with P1X Fab+P2X Fab+ P3X Fab or cetuximab did not lead to observable down-regulation of EGFR on visual inspection of the immunoblots.

Figure 15:
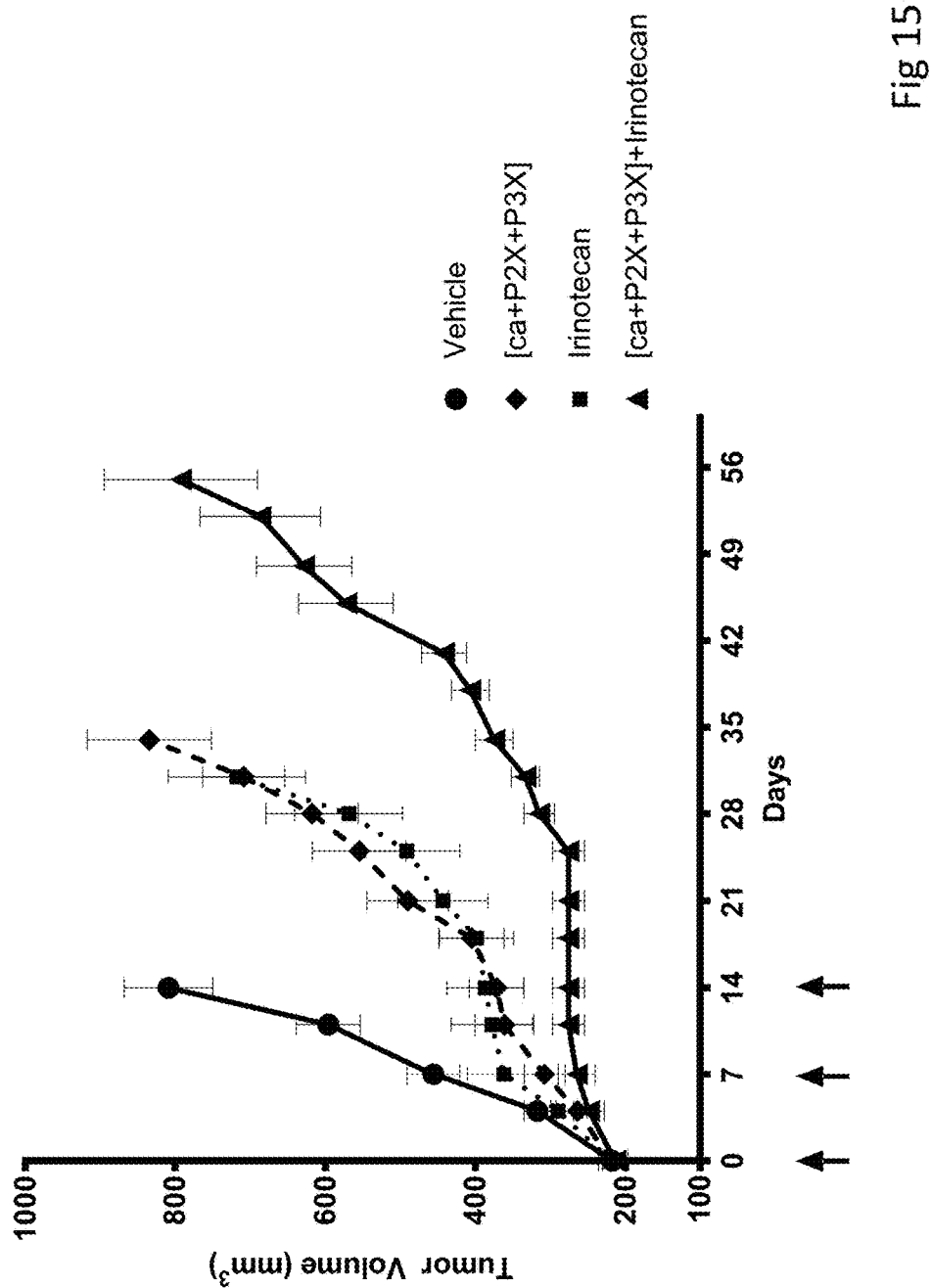
FIG. 15 is a graph showing the results of a patient derived colorectal cancer tumor xenograft murine mouse model experiment, demonstrating decreased tumor volume in vivo in mice treated with ca+P2X+P3X antibodies and irinotecan alone and in combination, as compared to PBS control.

Example 15: Inhibition of Tumor Growth and Cell Proliferation In Vivo in Combination with Irinotecan Efficacy of [ca+P2X+P3X], irinotecan and [ca+P2X+P3X]+irinotecan were assessed in vivo compared to vehicle control (PBS) in a patient-derived colorectal cancer tumor xenograft murine mouse model by the methods described above. Arrows indicate days on which irinotecan was administered. The results shown in FIG. 15 demonstrate the ability of [ca+P2X+P3X] and of the combination of [ca+P2X+P3X] and irinotecan to inhibit tumor cell proliferation in vivo, with respect to vehicle control. The results shown in FIG. 15 also demonstrate the ability of the combination of [ca+P2X+P3X] and irinotecan to inhibit tumor growth (and cell proliferation) in vivo to a greater extent than either [ca+P2X+P3X] or irinotecan alone.

Example 16: Inhibition of Tumor Cell Proliferation In Vitro by Combinations of [P1X+P2X+P3X] and MM-121

Inhibition of tumor cell proliferation in vitro was analyzed in the cell lines A549, BxPC-3, DU 145, NCI-H1355, NCI-H226, NCI-H322M, NCI-H358, NCI-H520, HCC827, HT-1197, RT-112, SCaBER, SK-MES-1 and SW 900 by the methods described above. Cells were treated with all 80 pairwise combinations of [P1X+P2X+P3X] and MM-121 antibody concentrations listed in Table 16.

TABLE 16

| P1X + P2X + P3X Conc, nM | MM-121 Conc, nM |
| --- | --- |
| 2000 | 2000 |
| 666.7 | 666.7 |
| 222.2 | 222.2 |
| 74.1 | 74.1 |
| 24.7 | 24.7 |
| 8.2 | 8.2 |
| 2.7 | 2.7 |
| 0.9 | 0 |
| 0.3 | |
| 0 | |

It is noted that the concentrations shown in Table 16 are total concentrations for P1X+P2X+P3X. The ratio used is 2:2:1, so the individual concentrations of P1X, P2X and P3X are 40%, 40% and 20% of the total concentration, respectively. The ordinarily skilled artisan will understand that each specific concentration value in Table 16 is subject to some minor experimental variability, so that each specific concentration given indicates a value of about the indicated concentration (e.g., a concentration indicated in a table as 2000 nM represents a value of about 2000 nM).

For each cell line, inhibition of cell proliferation was measured using the CellTiter-Glo® (CTG) Luminescent Cell Viability Assay (Promega Corporation) which measures the number of viable cells in culture based upon quantitation of ATP present, which is an indicator of metabolically active cells. For each dose combination used, percent inhibition with respect to EGF+HRG control is calculated and is given in the upper table of FIGS. 17A-N. An HSA score is also calculated for each dose combination, with "True" values (indicating that the activity of the combination is greater than both of the two therapeutics alone) denoted with bold font, and "False" values denoted with regular font. For each dose combination in which both drugs are present, a Bliss independence score is calculated and is given in the lower table of FIGS. 16A-N. Bliss independence scores less than zero, indicating synergy, are denoted with bold font, and Bliss independence scores greater than or equal to zero, indicating lack of synergy or additivity, are denoted with italic and underlined font.

The results shown in FIGS. 16A-N demonstrate that an HSA score of "True" is observed with some combinations of [P1X+P2X+P3X] and MM-121 in all cell lines and is observed with the majority of combinations of [P1X+P2X+P3X] and MM-121 in 12 out of the 14 cell lines assessed. The results shown in FIGS. 16A-N also demonstrate that synergy is observed with some combinations of [P1X+P2X+P3X] and MM-121 in all cell lines and that synergy is observed with the majority of combinations of [P1X+P2X+P3X] and MM-121 in 12 out of the 14 cell lines assessed.

Example 17: Inhibition of Tumor Cell Proliferation In Vitro by Combinations of [P1X+P2X+P3X] and DTX Inhibition of tumor cell proliferation in vitro was analyzed in the cell lines A549, NCI-H1975, NCI-H226, NCI-H322M, HCC827, HOP-62, SK-MES-1 and SW 900 by the methods described above. Cells were treated with all 80 pairwise combinations of [P1X+P2X+P3X] and DTX concentrations listed in Table 17.

TABLE 17

| P1X + P2X + P3X Conc, nM | DTX Conc, ng/mL |
| --- | --- |
| 2000 | 1000 |
| 666.7 | 333.3 |
| 222.2 | 111.1 |
| 74.1 | 37.0 |
| 24.7 | 12.3 |
| 8.2 | 4.1 |
| 2.7 | 1.4 |
| 0.9 | 0 |
| 0.3 | |
| 0 | |

It is noted that the concentrations shown in Table 17 are total concentrations for P1X+P2X+P3X. The ratio used is 2:2:1, so the individual concentrations of P1X, P2X and P3X are 40%, 40% and 20% of the total concentration, respectively. The ordinarily skilled artisan will understand that each specific concentration value in Table 17 is subject to some minor experimental variability, so that each specific concentration given indicates a value of about the indicated concentration (e.g., a concentration indicated in a table as 2000 nM represents a value of about 2000 nM).

For each cell line, inhibition of cell proliferation was measured as described in Example 16. For each dose combination used, percent inhibition with respect to EGF control is calculated and is given in the upper table of FIGS. 17A-H. An HSA score is also calculated for each dose combination as described in Example 16, with "True" values denoted with bold font, and "False" values denoted with regular font. A Bliss independence score is also calculated as described in Example 16 and is shown in the lower table of FIGS. 17A-H. Bliss independence scores less than zero, indicating synergy, are denoted with bold font, and Bliss independence scores greater than or equal to zero, indicating lack of synergy or additivity, are denoted with italic and underlined font.

The results shown in FIGS. 17A-H demonstrate that an HSA score of "True" is observed with some combinations of [P1X+P2X+P3X] and DTX in all cell lines and is observed with the majority of combinations of [P1X+P2X+P3X] and DTX in 7 out of the 8 cell lines assessed. The results shown in FIGS. 17A-H also demonstrate that synergy is observed with some combinations of [P1X+P2X+P3X] and DTX in all cell lines and that synergy is observed with the majority of combinations of [P1X+P2X+P3X] and DTX in 6 out of the 8 cell lines assessed.

Example 19: Inhibition of Tumor Cell Proliferation In Vitro by Combinations of [P1X+P2X+P3X] and SN-38

Inhibition of tumor cell proliferation in vitro was analyzed in the cell lines A549, HCT 116, HT-29 and LoVo by the methods described above. A549 and LoVo cells were treated with all 80 pairwise combinations of [P1X+P2X+P3X] and SN-38 concentrations listed in Table 18.

TABLE 18

| P1X + P2X + P3X Conc, nM | SN-38 Conc, nM |
|---|---|
| 1000 | 1000 |
| 250 | 250 |
| 62.5 | 62.5 |
| 15.6 | 15.6 |
| 3.9 | 3.9 |
| 0.98 | 0.98 |
| 0.24 | 0.24 |
| 0 | 00.06 |
|  | 0.02 |
|  | 0 |

HCT 116 and HT-29 cells were treated with all 48 pairwise combinations of [P1X+P2X+P3X] and SN-38 concentrations listed in Table 19.

TABLE 19

| P1X + P2X + P3X Conc, nM | SN-38 Conc, nM |
|---|---|
| 2000 | 1000 |
| 500 | 250 |

TABLE 19-continued

| P1X + P2X + P3X Conc, nM | SN-38 Conc, nM |
|---|---|
| 250 | 62.5 |
| 125 | 15 |
| 62.5 | 3.9 |
| 0 | 1 |
|  | 0.2 |
|  | 0 |

It is noted that the concentrations shown in Table 18 and 19 are total concentrations for P1X+P2X+P3X. The ratio used is 2:2:1, so the individual concentrations of P1X, P2X and P3X are 40%, 40% and 20% of the total concentration, respectively. The ordinarily skilled artisan will understand that each specific concentration value in Tables 18 and 19 is subject to some minor experimental variability, so that each specific concentration given indicates a value of about the indicated concentration (e.g., a concentration indicated in a table as 2000 nM represents a value of about 2000 nM).

For each cell line, inhibition of cell proliferation was measured as described in Example 16. For each dose combination used, percent inhibition with respect to EGF control is calculated and is given in the upper table of FIGS. 18A-D. An HSA score is also calculated for each dose combination as described in Example 16, with "True" values denoted with bold font, and "False" values denoted with regular font. A Bliss independence score is also calculated as described in Example 16 and is shown in the lower table of FIGS. 18A-D. Bliss independence scores less than zero, indicating synergy, are denoted with bold font, and Bliss independence scores greater than or equal to zero, indicating lack of synergy or additivity, are denoted with italic and underlined font.

The results shown in FIGS. 18A-D demonstrate that an HSA score of "True" is observed with the majority of combinations of [P1X+P2X+P3X] and SN-38 in all 4 cell lines assessed. The results also demonstrate that synergy is observed with some combinations of [P1X+P2X+P3X] and DTX in all cell lines and that synergy is observed with the majority of combinations of [P1X+P2X+P3X] and SN-38 in 2 out of the 4 cell lines assessed.

EQUIVALENTS

Those skilled in the art will recognize, or be able to ascertain using no more than routine experimentation, many equivalents of the specific embodiments described herein. Such equivalents are intended to be encompassed by the following claims. Any combination of the embodiments disclosed in the any plurality of the dependent claims is contemplated to be within the scope of the disclosure.

INCORPORATION BY REFERENCE

All, patents, pending patent applications and patent publications referred to hereinabove are hereby incorporated by reference in their entireties.

APPENDIX A

| ANTI-CANCER AGENTS | | |
|---|---|---|
| Anti-Cancer Agent | Comments | Examples |
| Antibodies | Antibodies which bind IGF-1R (insulin-like growth factor type 1 receptor), which is expressed on the cell | A12 (fully humanized mAb) 19D12 (fully humanized mAb) CP751-871 (fully humanized mAb) H7C10 (humanized mAb) alphaIR3 (mouse) |

APPENDIX A-continued

ANTI-CANCER AGENTS

| Anti-Cancer Agent | Comments | Examples |
| --- | --- | --- |
| | surface of must human cancers | scFV/FC (mouse/human chimera)<br>EM/164 (mouse)<br>AMG 479 (fully humanized mAb; Amgen)<br>IMCA 12 (fully humanized mAb; Imclone)<br>NSC-742460 (Dyax)<br>MR-0646, F50035 (Pierre Fabre Medicament, Merck) |
| | Antibodies which bind EGFR; Mutations affecting EGFR expression or activity can result in cancer | matuzumab (EMD72000)<br>Erbitux ®/cetuximab (Imclone)<br>Vectibix ®/panitumumab (Amgen)<br>mAb 806<br>nimotuzumab (TheraCIM ®)<br>INCB7839 (Incyte)<br>panitumumab (Vectibix ®; Amgen) |
| | Antibodies which bind cMET (mesenchymal epithelial transition factor); a member of the MET family of receptor tyrosine kinases) | AV299 (AVEO)<br>AMG102 (Amgen)<br>5D5 (OA-5D5) (Genentech) |
| | Anti-ErbB3 antibodies | MM-121 (Merrimack Pharmaceuticals)<br>Ab #14 described in WO 2008/100624<br>1B4C3; 2D1D12 (U3 Pharma AG)<br>U3-1287/AMG888 (U3 Pharma/Amgen) |
| | Anti-ErbB2 (HER2) antibodies | Herceptin ® (trastuzumab; Genentech/Roche); Omnitarg ® (pertuzumab; 2C4,R1273; Genentech/Roche) |
| Small Molecules Targeting IGF1R | IGF-1R (insulin-like growth factor type 1 receptor), which is expressed on the cell surface of must human cancers | NVP-AEW541-A<br>BMS-536,924 (1H-benzoimidazol-2-yl)-1H-pyridin-2-one)<br>BMS-554,417<br>Cycloligan<br>TAE226<br>PQ401 |
| Small Molecules Targeting EGFR | EGFR; Mutations affecting EGFR expression or activity can result in cancer | Iressa ®/gefitinib (AstraZeneca)<br>CI-1033 (PD 183805) (Pfizer)<br>TYVERB/lapatinib (GlaxoSmithKline)<br>Tykerb ®/lapatinib ditosylate (SmithKline Beecham)<br>Tarceva ®/Erlotinib HCL (OSI Pharma)<br>PKI-166 (Novartis)<br>PD-158780<br>EKB-569<br>Tyrphostin AG 1478(4-(3-Chloroanillino)-6,7-dimethoxyquinazoline) |
| Small Molecules Targeting ErbB2 | ErbB2, also known as HER2, a member of the ErbB family of receptors, which is expressed on certain cancer cells | HKI-272 (neratinib; Wyeth)<br>KOS-953 (tanespimycin; Kosan Biosciences) |
| Small Molecules Targeting cMET | cMET (Mesenchymal epithelial transition factor); a member of the MET family of receptor tyrosine kinases) | PHA665752<br>ARQ 197 (ArQule)<br>ARQ-650RP (ArQule) |
| Antimetabolites | An antimetabolite is a chemical with a similar structure to a substance (a metabolite) required for normal biochemical reactions, yet different enough to interfere with the normal functions of cells, including cell division. | flourouracil (5-FU)<br>capecitabine/XELODA ® (HLR Roche)<br>5-trifluoromethyl-2'-deoxyuridine<br>methotrexate sodium (Trexall) (Barr)<br>raltitrexed/Tomudex ® (AstraZaneca)<br>pemetrexed/Alimta ® (Lilly)<br>tegafur<br>cytosine arabinoside (Cytarabine, Ara-C)/tioguanine/Lanvis ® (GlaxoSmithKline)<br>5-azacytidine<br>6-mercaptopurine (Mercaptopurine, 6-MP)<br>azathioprine/Azasan ® (AAIPHARMA LLC)<br>6-thioguanine (6-TG)/Purinethol ® (TEVA) |

APPENDIX A-continued

ANTI-CANCER AGENTS

| Anti-Cancer Agent | Comments | Examples |
|---|---|---|
| Alkylating agents | An alkylating antineoplastic agent is an alkylating agent that attaches an alkyl group to DNA. Since cancer cells generally proliferate unrestrictively more than do healthy cells they are more sensitive to DNA damage, and alkylating agents are used clinically to treat a variety of tumors. | pentostatin/Nipent ® (Hospira Inc.) fludarabine phosphate/Fludara ® (Bayer Health Care) cladribine/Leustatin ® (2-CdA, 2-chlorodeoxyadenosine) (Ortho Biotech) floxuridine (5-fluoro-2'-deoxyuridine)/FUDR ® (Hospira, Inc,) Ribonucleotide Reductase Inhibitor (RNR) cyclophosphamide/Cytoxan ® (BMS)/Neosar ® (TEVA) ifosfamide/Mitoxana ® (ASTA Medica) ThioTEPA (Bedford, Abraxis, Teva) BCNU→ 1,3-bis(2-chloroethyl)-1-nitosourea CCNU→ 1,-(2-chloroethyl)-3-cyclohexyl-1-nitrosourea (methyl CCNU) hexamethylmelamine (altretamine, HMM)/Hexalen ® (MGI Pharma Inc.) busulfan/Myleran ® (GlaxoSmithKline) procarbazine HCL/Matulane ® (Sigma Tau) Dacarbazine (DTIC ®) chlorambucil/Leukaran ® (SmithKline Beecham) Melphalan/Alkeran ® (GlaxoSmithKline) cisplatin (Cisplatinum, CDDP)/Platinol (Bristol Myers) carboplatin/Paraplatin (BMS) oxaliplatin/Eloxitan ® (Sanofi-Aventis US) Bendamustine carboquone carmustine chloromethine dacarbazine (DTIC) fotemustine lomustine mannosulfan nedaplatin nimustine prednimustine ranimustine satraplatin semustine streptozocin temozolomide treosulfan triaziquone triethylene melamine triplatin tetranitrate trofosfamide uramustine |
| Topoisomerase inhibitors | Topoisomerase inhibitors are chemotherapy agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. | doxorubicin HCL/Doxil ® (Alza) daunorubicin citrate/Daunoxome ® (Gilead) mitoxantrone HCL/Novantrone (EMD Serono) actinomycin D etoposide/Vepesid ® (BMS)/Etopophos ® (Hospira, Bedford, Teva Parenteral, Etc.) topotecan HCL/Hycamtin ® (GlaxoSmithKline) teniposide (VM-26)/Vumon ® (BMS) irinotecan HCL(CPT-11)/camptosar ® (Pharmacia & Upjohn) camptothecin (CPT) belotecan rubitecan |
| Microtubule targeting agents | Microtubules are one of the components of the cytoskeleton. They have diameter of approximately 24 nm and length varying from | vincristine/Oncovin ® (Lilly) vinblastine sulfate/Velban ®(discontinued) (Lilly) vinorelbine tartrate/Navelbine ® (PierreFabre) vindesine sulphate/Eldisine ® (Lilly) |

APPENDIX A-continued

ANTI-CANCER AGENTS

| Anti-Cancer Agent | Comments | Examples |
|---|---|---|
| | several micrometers to possibly millimeters in axons of nerve cells. Microtubules serve as structural components within cells and are involved in many cellular processes including mitosis, cytokinesis, and vesicular transport. | paclitaxel/Taxol ® (BMS) docetaxel/Taxotere ® (Sanofi Aventis US) Nanoparticle paclitaxel (ABI-007)/ Abraxane ® (Abraxis BioScience, Inc.) ixabepilone/IXEMPRA ™ (BMS) larotaxel ortataxel tesetaxel vinflunine |
| Kinase inhibitors | Tyrosine kinases are enzymes within the cell that function to attach phosphate groups to the amino acid tyrosine. By blocking the ability of protein tyrosine kinases to function, these compounds provide a tool for controlling cancerous cell growth. | imatinib mesylate/Gleevec (Novartis) sunitinib malate/Sutent ® (Pfizer) sorafenib tosylate/Nexavar ® (Bayer) nilotinib hydrochloride monohydrate/ Tasigna ® (Novartis) AMG 386 (Amgen) axitinib (AG-013736; Pfizer, Inc.) bosutinib (SKI-606; Wyeth) brivanib alalinate (BMS-582664; BMS) cediranib (AZD2171; Recentin, AstraZeneca) dasatinib (BMS-354825: Sprycel ®; BMS) lestaurtinib (CEP-701; Cephalon) motesanib diphosphage (AMG-706; Amgen/Takeda) pazopanib HCL (GW786034; Armala, GSK) semaxanib (SU5416; Pharmacia) vandetanib (AZD647; Zactima; AstraZeneca) vatalanib (PTK-787; Novartis, Bayer Schering Pharma) XL184 (NSC718781; Exelixis, GSK) |
| Protein synthesis inhibitors | Induces cell apoptosis | L-asparaginase/Elspar ® (Merck & Co.) |
| Immunotherapeutic agents | Induces cancer patients to exhibit immune responsiveness | Alpha interferon Angiogenesis Inhibitor/Avastin ® (Genentech) IL-2→ Interleukin 2 (Aldesleukin)/ Proleukin ® (Chiron) IL-12→ Interleukin 12 |
| Hormonal therapies | Hormonal therapies associated with menopause and aging seek to increase the amount of certain hormones in the body to compensate for age- or disease-related hormonal declines. Hormonal therapy as a cancer treatment generally either reduces the level of one or more specific hormones, blocks a hormone from interacting with its cellular receptor or otherwise alters the cancer's ability to be stimulated by hormones to grow and spread. Such hormonal therapies thus include hormone antagonists and hormone synthesis inhibitors. In some instances hormone agonists may also be used as anticancer hormonal therapies. | Ttoremifene citrate/Fareston ® (GTX, Inc.) fulvestrant/Faslodex ® (AstraZeneca) raloxifene HCL/Evista ® (Lilly) anastrazole/Arimidex ® (AstraZeneca) letrozole/Femara ® (Novartis) fadrozole (CGS 16949A) exemestane/Aromasin ® (Pharmacia & Upjohn) leuprolide acetate/Eligard ® (QTL USA) Lupron ® (TAP Pharm.) goserelin acetate/Zoladex ® (AstraZeneca) triptorelin pamoate/Trelstar ® (Watson Labs) buserelin/Suprefact ® (Sanofi Aventis) nafarelin cetrorelix/Cetrotide ® (EMD Serono) bicalutamide/Casodex ® (AstraZeneca) nilutamide/Nilandron ® (Aventis Pharm.) megestrol acetate/Megace ® (BMS) somatostatin Analogs (e.g., Octreotide acetate/Sandostatin ® (Novartis)) abarelix (Plenaxis ™; Amgen) abiraterone acetate (CB7630; BTG plc) afimoxifene (TamoGel; Ascend Therapeutics, Inc.) aromatase inhibitor (Atamestane plus toremifene; Intarcia Therapeutics, Inc.) arzoxifene (Eli Lilly & Co) Asentar ™; DN-101 (Novacea; Oregon Health Sciences U) flutamide (Eulexin ®, Schering; Prostacur, Laboratorios Almirall, S.A) letrozole (CGS20267) (Femara ®, |

APPENDIX A-continued

ANTI-CANCER AGENTS

| Anti-Cancer Agent | Comments | Examples |
|---|---|---|
| | | Chugai; Estrochek ®, (Jagsonpal Pharmaceuticals Ltd;) Delestrogen ®, estradiol valerate (Jagsonpal) magestrol acetate/Megace ® medroxyprogesteone acetate (Veraplex ®; Combiphar) MT206 (Medisyn Technologies, Inc.) nandrolone decanoate (Zestabolin ®; Mankind Pharma Ltd) tamoxifen (Taxifen ®, Yung Shin Pharmaceutical; Tomifen ®, Alkem Laboratories Ltd.) tamoxifen citrate (Nolvadex, AstraZeneca; soltamox, EUSA Pharma Inc; tamoxifen citrate SOPHARMA, Sopharma JSCo.) |
| Glucocorticoids | Anti-inflammatory drugs used to reduce swelling that causes cancer pain. | predinsolone dexamethasone/Decadron ® (Wyeth) prednisone (Deltasone, Orasone, Liquid Pred, Sterapred ®) |
| Aromatase inhibitors | Includes imidazoles | ketoconazole |
| mTOR inhibitors | The mTOR signaling pathway was originally discovered during studies of the immunosuppressive agent rapamycin. This highly conserved pathway regulates cell proliferation and metabolism in response to environmental factors, linking cell growth factor receptor signaling via phosphoinositide-3-kinase (PI-3K) to cell growth, proliferation, and angiogenesis. | sirolimus (Rapamycin)/Rapamune ® (Wyeth) Temsirolimus (CCI-779)/Torisel ® (Wyeth) Deforolimus (AP23573) (Ariad Pharm.) Everolimus (RAD001)/Certican ® (Novartis) |
| Chemotherapeutic agents | | adriamycin, 5-fluorouracil, cytoxin, bleomycin, mitomycin C, daunomycin, carminomycin, aminopterin, dactinomycin, mitomycins, esperamicins, clofarabine, mercaptopurine, pentostatin, thioguanine, cytarabine, decitabine, floxuridine, gemcitabine (Gemzar), enocitabine, sapacitabine |
| Protein Kinase B (PKB) Inhibitors | | AKT Inhibitor Astex ® (Astex Therapeutics) AKT Inhibitors NERVIANO (Nerviano Medical Sciences) AKT Kinase Inhibitor TELIK (Telik Inc) AKT DECIPHERA (Deciphera Pharmaceuticals, EEC) perifosine (KRX0401, D-21266; Keryx Biopharmaceuticals Inc, AEterna Zentaris Inc) perifosine with Docetaxel (Keryx Biopharmaceuticals Inc, AEterna Zentaris Inc) perifosine with Gemcitabine (AEterna Zentaris Inc) perifosine with paclitaxel (AEterna Zentaris Inc) protein kinase-B inhibitor DEVELOGEN (DeveloGen AG) PX316 (Oncothyreon, Inc.) RX0183 (Rexahn Pharmaceuticals Inc) RX0201 (Rexahn Pharmaceuticals Inc) VQD002 (VioQuest Pharmaceuticals Inc) XL418 (Exelixis Inc) ZEN027 (AEterna Zentaris Inc) |

APPENDIX A-continued

ANTI-CANCER AGENTS

| Anti-Cancer Agent | Comments | Examples |
|---|---|---|
| Phosphatidylinositol 3-Kinase (PI3K) Inhibitors | | BEZ235 (Novartis AG)<br>BGT226 (Novartis AG)<br>CAL101 (Calistoga Pharmaceuticals, Inc.)<br>CHR4432 (Chroma Therapeutics Ltd)<br>Erk/PI3K Inhibitors ETERNA (AEterna Zentaris Inc)<br>GDC0941 (Genentech Inc/Piramed Limited/Roche Holdings Ltd)<br>enzastaurin HCL (LY317615; Enzastaurin; Eli Lilly)<br>LY294002/Wortmannin<br>PI3K Inhibitors SEMAFORE (Semafore Pharmaceuticals)<br>PX866 (Oncothyreon, Inc.)<br>SF1126 (Semafore Pharmaceuticals)<br>VMD-8000 (VM Discovery, Inc.)<br>XL147 (Exelixis Inc)<br>XL147 with XL647 (Exelixis Inc)<br>XL765 (Exelixis Inc)<br>PI-103 (Roche/Piramed) |
| Cyclin Dependent Kinase Inhibitors | | CYC200, R-roscovitine (Seliciclib; Cyclacel Pharma)<br>NSC-649890, L86-8275, HMR-1275 (alvocidib; NCI) |
| TLr9, CD289 | | IMOxine (Merck KGaA)<br>HYB2055 (Idera)<br>IMO-2055 (Isis Pharma)<br>1018 ISS (Dynavax Technologies/UCSF)<br>PF-3512676 (Pfizer) |
| Enzyme Inhibitor | | lonafarnib(SCH66336; Sarasar; SuperGen, U Arizona) |
| Anti-TRAIL | | AMG-655 (Aeterna Zentaris, Keryx Biopharma)<br>Apo2L/TRAIL, AMG951 (Genentech, Amgen)<br>APOMAB (fully humanized mAb; Genentech) |
| MEK Inhibitors | [Mitogen-Activated Protein Kinase Kinase 1 (MAP2K1); Mitogen-Activated Protein Kinase Kinase 2 (MAP2K2)] | ARRY162 (Array BioPharma Inc)<br>ARRY704 (Array BioPharma Inc)<br>ARRY886 (Array BioPharma Inc)<br>AS703026 (Merck Serono S.A)<br>AZD6244 (AstraZeneca Plc)<br>AZD8330 (AstraZeneca Plc)<br>RDEA119 (Ardea Biosciences, Inc.)<br>RDEA436 (Ardea Biosciences, Inc.)<br>XL518 (Exelixis Inc; Genentech Inc) |
| Miscellaneous Inhibitors | | Imprime PGG (Biothera)<br>CHR-2797 (AminopeptidaseM1 inhibitor; Chroma Therapeutics)<br>E7820, NSC 719239 (Integrin-alpha2 inhibitor, Eisai)<br>INCB007839 (ADAM 17, TACE Inhibitor; Incyte)<br>CNF2024,BIIB021 (Hsp90 Inhibitor; Biogen Idec)<br>MP470, HPK-56 (Kit/Mel/Ret Inhibitor; Schering-Plough)<br>SNDX-275/MS-275 (HDAC Inhibitor; Syndax)<br>Zarnestra ™,Tipifarnib, R115777 (Ras Inhibitor; Janssen Pharma)<br>volociximab; Eos 200-4,M200 (alpha581 integrin inhibitor; Biogen Idec; Eli Lilly/UCSF/PDL BioPharma)<br>apricoxib (TP2001; COX-2 Inhibitor, Daiichi Sankyo; Tragara Pharma) |

SEQUENCE LISTING SUMMARY

| | | |
|---|---|---|
| P1X $V_H$ CDR1 | SYAIS | SEQ ID NO: 1 |
| PIX $V_H$ CDR2 | IIPIFGTVNY | SEQ ID NO: 2 |

SEQUENCE LISTING SUMMARY

| | | |
|---|---|---|
| P1X V<sub>H</sub> CDR3 | DPSVNL | SEQ ID NO: 3 |
| P1X V<sub>L</sub> CDR1 | QSISSWWA | SEQ ID NO: 4 |
| P1X V<sub>L</sub> CDR2 | DASSL | SEQ ID NO: 5 |
| P1X V<sub>L</sub> CDR3 | QQYHAHP | SEQ ID NO: 6 |
| P2X V<sub>H</sub> CDR1 | SYAIS | SEQ ID NO: 7 |
| P2X V<sub>H</sub> CDR2 | IIPIFGAANP | SEQ ID NO: 8 |
| P2X V<sub>H</sub> CDR3 | MGRGKV | SEQ ID NO: 9 |
| P2X V<sub>L</sub> CDR1 | QSVLYSPNNKNYLA | SEQ ID NO: 10 |
| P2X V<sub>L</sub> CDR2 | WASTR | SEQ ID NO: 11 |
| P2X V<sub>L</sub> CDR3 | QQYYGSP | SEQ ID NO: 12 |
| P3X V<sub>H</sub> CDR1 | SYGIN | SEQ ID NO: 13 |
| P3X V<sub>H</sub> CDR2 | ISAYNGNTYY | SEQ ID NO: 14 |
| P3X V<sub>H</sub> CDR3 | DLGGYGSGS | SEQ ID NO: 15 |
| P3X V<sub>L</sub> CDR1 | QSVSSNLA | SEQ ID NO: 16 |
| P3X V<sub>L</sub> CDR2 | GASTR | SEQ ID NO: 17 |
| P3X V<sub>L</sub> CDR3 | QDYRTWPR | SEQ ID NO: 18 |
| P1X V<sub>H</sub> | MGFGLSWLFLVAILKGVQC QVQLVQSGAEVKKPGSSVKV SCKASGGTFSSYAISWVRQA PGQGLEWMGSIIPIFGTVNY AQKFQGRVTITADESTSTAY MELSSLRSEDTAVYYCARDP SVNLYWYFDLWGRGTLVTVSS | SEQ ID NO: 19 |
| P1X V<sub>L</sub> | MGTPAQLLFLLLLWLPDTTG DIQMTQSPSTLSASVGDRVT ITCRASQSISSWWAWYQQKP GKAPKLLIYDASSLESGVPS RFSGSGSGTEFTLTISSLQP DDFATYYCQQYHAHPTTFGG GTKVEIK | SEQ ID NO: 20 |
| P2X V<sub>H</sub> | MGFGLSWLFLVAILKGVQC QVQLVQSGAEVKKPGSSVKV SCKASGGTFGSYAISWVRQA PGQGLEWMGSIIPIFGAANP AQKSQGRVTITADESTSTAY MELSSLRSEDTAVYYCAKMG RGKVAFDIWGQGTMVTVSS | SEQ ID NO: 21 |
| P2X V<sub>L</sub> | MGTPAQLLFLLLLWLPDTTG DIVMTQSPDSLAVSLGERAT INCKSSQSVLYSPNNKNYLA WYQQKPGQPPKLLIYWASTR ESGVPDRFSGSGSGTDFTLT ISSLQAEDVAVYYCQQYYGS PITFGGGTKVEIK | SEQ ID NO: 22 |
| P3X V<sub>H</sub> | MGFGLSWLFLVAILKGVQC QVQLVQSGAEVKKPGASVKV SCKASGYAFTSYGINWVRQA PGQGLEWMGWISAYNGNTYY AQKLRGRVTMTTDTSTSTAY MELRSLRSDDTAVYYCARDL GGYGSGSVPFDPWGQGTLVTVSS | SEQ ID NO: 23 |
| P3X V<sub>L</sub> | MGTPAQLLFLLLLWLPDTTG EIVMTQSPATLSVSPGERAT LSCRASQSVSSNLAWYQQKP GQAPRLLIYGASTRATGIPA | SEQ ID NO: 24 |

| SEQUENCE LISTING SUMMARY | | |
|---|---|---|
| | RFSGSGSGTEFTLTISSLQS<br>EDFAVYYCQDYRTWPRRVFG<br>GGTKVEIK | |
| pMP10K_IgG1<br>Light Chain<br>Kappa-Constant | RTVAAPSVFIFPPSDEQLKS<br>GTASVVCLLNNFYPREAKVQ<br>WKVDNALQSGNSQESVTEQD<br>SKDSTYSLSSTLTLSKADYE<br>KHKVYACEVTHQGLSSPVTK<br>SFNRGEC | SEQ ID NO: 25 |
| pMP10K_IgG1<br>Heavy Chain<br>(EEM)_Constant | ASTKGPSVFPLAPSSKSTSG<br>GTAALGCLVKDYFPEPVTVS<br>WNSGALTSGVHTFPAVLQSS<br>GLYSLSSVVTVPSSSLGTQT<br>YICNVNHKPSNTKVDKKVEP<br>KSCDKTHTCPPCPAPELLGG<br>PSVFLFPPKPKDTLMISRTP<br>EVTCVVVDVSHEDPEVKFNW<br>YVDGVEVHNAKTKPREEQYN<br>STYRVVSVLTVLHQDWLNGK<br>EYKCKVSNKALPAPIEKTIS<br>KAKGQPREPQVYTLPPSREE<br>MTKNQVSLTCLVKGFYPSDI<br>AVEWESNGQPENNYKTTPPV<br>LDSDGSFFLYSKLTVDKSRW<br>QQGNVFSCSVMHEALHNHYT<br>QKSLSLSPGK | SEQ ID NO: 26 |
| ca/cd V$_H$ CDR2 | IIPIFGTANY | SEQ ID NO: 27 |
| ca V$_H$ CDR3 | DPSVDL | SEQ ID NO: 28 |
| ca V$_L$ CDR1 | QSISSWLA | SEQ ID NO: 29 |
| ca V$_L$ CDR3 | QQFAAHA | SEQ ID NO: 30 |
| cd V$_L$ CDR1 | QSVLYSSNNKNYLA | SEQ ID NO: 31 |
| ch V$_H$ CDR2 | ISAYNGNTNY | SEQ ID NO: 32 |

EGFR ECD (SEQ ID NO: 33)

```
  1 MRPSGTAGAA LLALLAALCP ASRALEEKKV CQGTSNKLTQ LGTFEDHFLS LQRMFNNCEV
 61 VLGNLEITYV QRNYDLSFLK TIQEVAGYVL IALNTVERIP LENLQIIRGN MYYENSYALA
121 VLSNYDANKT GLKELPMRNL QEILHGAVRF SNNPALCNVE SIQWRDIVSS DFLSNMSMDF
181 QNHLGSCQKC DPSCPNGSCW GAGEENCQKL TKIICAQQCS GRCRGKSPSD CCHNQCAAGC
241 TGPRESDCLV CRKFRDEATC KDTCPPLMLY NPTTYQMDVN PEGKYSFGAT CVKKCPRNYV
301 VTDHGSCVRA CGADSYEMEE DGVRKCKKCE GPCRKVCNGI GIGEFKDSLS INATNIKHFK
361 NCTSISGDLH ILPVAFRGDS FTHTPPLDPQ ELDILKTVKE ITGFLLIQAW PENRTDLHAF
421 ENLEIIRGRT KQHGQFSLAV VSLNITSLGL RSLKEISDGD VIISGNKNLC YANTINWKKL
481 FGTSGQKTKI ISNRGENSCK ATGQVCHALC SPEGCWGPEP RDCVSCRNVS RGRECVDKCN
541 LLEGEPREFV ENSECIQCHP ECLPQAMNIT CTGRGPDNCI QCAHYIDGPH CVKTCPAGVM
601 GENNTLVWKY ADAGHVCHLC HPNCTYGCTG PGLEGCPTNG PKIPSHHHHH H
```

What is claimed is:

1. A monoclonal antibody which binds EGFR extracellular domain and comprises heavy chain CDR1, CDR2, and CDR3 sequences as set forth in SEQ ID NOs: 1, 2, and 3, respectively, and light chain CDR1, CDR2, and CDR3 sequences as set forth in SEQ ID NOs: 4, 5 and 6, respectively.

2. A monoclonal antibody which binds EGFR extracellular domain and comprises a heavy chain variable region as set forth in SEQ ID NO: 19 and a light chain variable region as set forth in SEQ ID NO: 20.

3. The monoclonal antibody of claim 1, wherein the antibody binds EGFR extracellular domain with a $K_D$ of better than 1 nM.

4. The monoclonal antibody of claim 1, wherein the antibody is a human or humanized antibody.

5. The monoclonal antibody of claim 1, wherein the antibody is an IgG1.

6. The monoclonal antibody of claim 2, wherein the antibody is a human or humanized antibody.

7. The monoclonal antibody of claim 2, wherein the antibody is an IgG1.

8. The monoclonal antibody of claim 3, wherein the antibody is a human or humanized antibody.

9. The monoclonal antibody of claim 3, wherein the antibody is an IgG1.

10. A composition comprising the monoclonal antibody of claim 1 and a pharmaceutically acceptable carrier.

11. The composition according to claim 10, which is a sterile composition.

12. The composition according to claim 11, which is formulated for intravenous injection.

13. A composition comprising the monoclonal antibody of claim 2 and a pharmaceutically acceptable carrier.

14. The composition according to claim 13, which is a sterile composition.

15. The composition according to claim 14, which is formulated for intravenous injection.

16. A composition comprising the monoclonal antibody of claim 3 and a pharmaceutically acceptable carrier.

17. The composition according to claim 16, which is a sterile composition.

18. The composition according to claim 17, which is formulated for intravenous injection.

19. A composition comprising the monoclonal antibody of claim 5 and a pharmaceutically acceptable carrier.

20. A composition comprising the monoclonal antibody of claim 7 and a pharmaceutically acceptable carrier.

21. A composition comprising the monoclonal antibody of claim 9 and a pharmaceutically acceptable carrier.

* * * * *

SEQUENCE LISTING

<160> NUMBER OF SEQ ID NOS: 33

<210> SEQ ID NO 1
<211> LENGTH: 5
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 1

Ser Tyr Ala Ile Ser
1               5

<210> SEQ ID NO 2
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ile Ile Pro Ile Phe Gly Thr Val Asn Tyr
1               5                   10

<210> SEQ ID NO 3
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Asp Pro Ser Val Asn Leu
1               5

<210> SEQ ID NO 4
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gln Ser Ile Ser Ser Trp Trp Ala
1               5

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Asp Ala Ser Ser Leu
1               5

<210> SEQ ID NO 6
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 6

Gln Gln Tyr His Ala His Pro
1               5

<210> SEQ ID NO 7
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ser Tyr Ala Ile Ser
1               5

<210> SEQ ID NO 8
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ile Ile Pro Ile Phe Gly Ala Ala Asn Pro
1               5                   10

<210> SEQ ID NO 9
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Met Gly Arg Gly Lys Val
1               5

<210> SEQ ID NO 10
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gln Ser Val Leu Tyr Ser Pro Asn Asn Lys Asn Tyr Leu Ala
1               5                   10

<210> SEQ ID NO 11
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Trp Ala Ser Thr Arg
1               5
```

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gln Gln Tyr Tyr Gly Ser Pro
1               5

<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Tyr Gly Ile Asn
1               5

<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ile Ser Ala Tyr Asn Gly Asn Thr Tyr Tyr
1               5                   10

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Leu Gly Gly Tyr Gly Ser Gly Ser
1               5

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gln Ser Val Ser Ser Asn Leu Ala
1               5

<210> SEQ ID NO 17
<211> LENGTH: 5

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Ala Ser Thr Arg
1               5

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Gln Asp Tyr Arg Thr Trp Pro Arg
1               5

<210> SEQ ID NO 19
<211> LENGTH: 140
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

Glu Trp Met Gly Ser Ile Ile Pro Ile Phe Gly Thr Val Asn Tyr Ala
65                  70                  75                  80

Gln Lys Phe Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asp Pro Ser Val Asn Leu Tyr Trp Tyr Phe Asp
        115                 120                 125

Leu Trp Gly Arg Gly Thr Leu Val Thr Val Ser Ser
    130                 135                 140

<210> SEQ ID NO 20
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Gly Thr Pro Ala Gln Leu Leu Phe Leu Leu Leu Leu Trp Leu Pro

```
1               5                   10                  15
Asp Thr Thr Gly Asp Ile Gln Met Thr Gln Ser Pro Ser Thr Leu Ser
                20                  25                  30

Ala Ser Val Gly Asp Arg Val Thr Ile Thr Cys Arg Ala Ser Gln Ser
        35                  40                  45

Ile Ser Ser Trp Trp Ala Trp Tyr Gln Gln Lys Pro Gly Lys Ala Pro
    50                  55                  60

Lys Leu Leu Ile Tyr Asp Ala Ser Ser Leu Glu Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln Gln Tyr His
            100                 105                 110

Ala His Pro Thr Thr Phe Gly Gly Gly Thr Lys Val Glu Ile Lys
        115                 120                 125
```

<210> SEQ ID NO 21
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

```
Met Gly Phe Gly Leu Ser Trp Leu Phe Leu Val Ala Ile Leu Lys Gly
1               5                   10                  15

Val Gln Cys Gln Val Gln Leu Val Gln Ser Gly Ala Glu Val Lys Lys
                20                  25                  30

Pro Gly Ser Ser Val Lys Val Ser Cys Lys Ala Ser Gly Gly Thr Phe
            35                  40                  45

Gly Ser Tyr Ala Ile Ser Trp Val Arg Gln Ala Pro Gly Gln Gly Leu
        50                  55                  60

Glu Trp Met Gly Ser Ile Ile Pro Ile Phe Gly Ala Ala Asn Pro Ala
65                  70                  75                  80

Gln Lys Ser Gln Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Lys Met Gly Arg Gly Lys Val Ala Phe Asp Ile Trp
        115                 120                 125

Gly Gln Gly Thr Met Val Thr Val Ser Ser
    130                 135
```

<210> SEQ ID NO 22
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

```
Met Gly Thr Pro Ala Gln Leu Leu Phe Leu Leu Leu Leu Trp Leu Pro
1               5                   10                  15

Asp Thr Thr Gly Asp Ile Val Met Thr Gln Ser Pro Asp Ser Leu Ala
                20                  25                  30
```

```
Val Ser Leu Gly Glu Arg Ala Thr Ile Asn Cys Lys Ser Ser Gln Ser
        35                  40                  45
Val Leu Tyr Ser Pro Asn Asn Lys Asn Tyr Leu Ala Trp Tyr Gln Gln
 50                  55                  60
Lys Pro Gly Gln Pro Pro Lys Leu Leu Ile Tyr Trp Ala Ser Thr Arg
 65                  70                  75                  80
Glu Ser Gly Val Pro Asp Arg Phe Ser Gly Ser Gly Ser Gly Thr Asp
                85                  90                  95
Phe Thr Leu Thr Ile Ser Ser Leu Gln Ala Glu Asp Val Ala Val Tyr
                100                 105                 110
Tyr Cys Gln Gln Tyr Tyr Gly Ser Pro Ile Thr Phe Gly Gly Gly Thr
            115                 120                 125
Lys Val Glu Ile Lys
    130
```

<210> SEQ ID NO 23
<211> LENGTH: 142
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

```
Met Gly Phe Gly Leu Ser Trp Leu Phe Leu Val Ala Ile Leu Lys Gly
 1               5                  10                  15
Val Gln Cys Gln Val Gln Leu Val Gln Ser Gly Ala Glu Val Lys Lys
                20                  25                  30
Pro Gly Ala Ser Val Lys Val Ser Cys Lys Ala Ser Gly Tyr Ala Phe
            35                  40                  45
Thr Ser Tyr Gly Ile Asn Trp Val Arg Gln Ala Pro Gly Gln Gly Leu
 50                  55                  60
Glu Trp Met Gly Trp Ile Ser Ala Tyr Asn Gly Asn Thr Tyr Tyr Ala
 65                  70                  75                  80
Gln Lys Leu Arg Gly Arg Val Thr Met Thr Thr Asp Thr Ser Thr Ser
                85                  90                  95
Thr Ala Tyr Met Glu Leu Arg Ser Leu Arg Ser Asp Asp Thr Ala Val
                100                 105                 110
Tyr Tyr Cys Ala Arg Asp Leu Gly Gly Tyr Gly Ser Gly Ser Val Pro
            115                 120                 125
Phe Asp Pro Trp Gly Gln Gly Thr Leu Val Thr Val Ser Ser
    130                 135                 140
```

<210> SEQ ID NO 24
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

```
Met Gly Thr Pro Ala Gln Leu Leu Phe Leu Leu Leu Leu Trp Leu Pro
 1               5                  10                  15
Asp Thr Thr Gly Glu Ile Val Met Thr Gln Ser Pro Ala Thr Leu Ser
                20                  25                  30
```

Val Ser Pro Gly Glu Arg Ala Thr Leu Ser Cys Arg Ala Ser Gln Ser
         35                  40                  45

Val Ser Ser Asn Leu Ala Trp Tyr Gln Gln Lys Pro Gly Gln Ala Pro
 50                  55                  60

Arg Leu Leu Ile Tyr Gly Ala Ser Thr Arg Ala Thr Gly Ile Pro Ala
65                  70                  75                  80

Arg Phe Ser Gly Ser Gly Ser Gly Thr Glu Phe Thr Leu Thr Ile Ser
             85                  90                  95

Ser Leu Gln Ser Glu Asp Phe Ala Val Tyr Tyr Cys Gln Asp Tyr Arg
            100                 105                 110

Thr Trp Pro Arg Arg Val Phe Gly Gly Gly Thr Lys Val Glu Ile Lys
        115                 120                 125

<210> SEQ ID NO 25
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 26
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys

```
                    85                  90                  95
Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ile Ile Pro Ile Phe Gly Thr Ala Asn Tyr
1               5                   10

<210> SEQ ID NO 28
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Asp Pro Ser Val Asp Leu
1               5

<210> SEQ ID NO 29
```

```
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Gln Ser Ile Ser Ser Trp Leu Ala
1               5

<210> SEQ ID NO 30
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gln Gln Phe Ala Ala His Ala
1               5

<210> SEQ ID NO 31
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Gln Ser Val Leu Tyr Ser Ser Asn Asn Lys Asn Tyr Leu Ala
1               5                   10

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ile Ser Ala Tyr Asn Gly Asn Thr Asn Tyr
1               5                   10

<210> SEQ ID NO 33
<211> LENGTH: 651
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45
```

-continued

```
Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
```

-continued

```
465                 470                 475                 480
Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser His His His His His His
                645                 650
```